(12) United States Patent
Ruah et al.

(10) Patent No.: US 8,609,703 B2
(45) Date of Patent: Dec. 17, 2013

(54) MODULATORS OF ATP-BINDING CASSETTE TRANSPORTERS

(75) Inventors: Sara Hadida Ruah, La Jolla, CA (US); Anna Hazelwood, San Diego, CA (US); Peter Grootenhuis, San Diego, CA (US); Jinglan Zhou, San Diego, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 13/544,312

(22) Filed: Jul. 9, 2012

(65) Prior Publication Data

US 2013/0011923 A1   Jan. 10, 2013

Related U.S. Application Data

(62) Division of application No. 11/374,334, filed on Mar. 13, 2006, now Pat. No. 8,242,149.

(60) Provisional application No. 60/669,174, filed on Apr. 7, 2005, provisional application No. 60/661,310, filed on Mar. 11, 2005.

(51) Int. Cl.
| | | |
|---|---|---|
| *A01N 43/64* | (2006.01) |
| *A01N 43/36* | (2006.01) |
| *A01N 43/38* | (2006.01) |
| *A61K 31/41* | (2006.01) |
| *A61K 31/40* | (2006.01) |

(52) U.S. Cl.
USPC ............ 514/359; 514/408; 514/410; 514/412

(58) Field of Classification Search
USPC .................. 514/359, 408, 410, 412
See application file for complete search history.

*Primary Examiner* — Yong Chong
(74) *Attorney, Agent, or Firm* — Nancy K. Brennan

(57) ABSTRACT

The present invention relates to modulators of ATP-Binding Cassette ("ABC") transporters or fragments thereof, including Cystic Fibrosis Transmembrane Conductance Regulator ("CFTR"), compositions thereof, and methods therewith. The present invention also relates to methods of treating ABC transporter mediated diseases using such modulators.

26 Claims, 18 Drawing Sheets

1) 1H-Indole-3-acetamide, N-[3-[[[(2-chloro-4,5-difluorophenyl)amino]carbonyl]amino]-4-methoxyphenyl]-α-oxo- 2) 1H-Indole-3-acetamide, N-(5-cyclopropyl-1H-pyrazol-3-yl)-α-oxo- 3) 1,4-Benzenedicarboxamide, 2-[(1H-indol-3-yloxoacetyl)amino]-N,N'-bis(phenylmethyl)

4) 1H-Indole-3-acetamide, α-oxo-N-4-pyridinyl- 5) 1H-Indole-3-acetamide, α-oxo-N-3-pyridinyl- 6) 1H-Indole-3-acetamide, N-(4-nitrophenyl)-α-oxo- 7) 1H-Indole-3-acetamide, N-(4-fluorophenyl)-α-oxo- 8) 1H-Indole-3-acetamide, 6-nitro-α-oxo-N-4-pyridinyl- 9) 1H-Indole-3-acetamide, 5-nitro-α-oxo-N-4-pyridinyl- 10) 1H-Indole-3-acetamide, α-oxo-N-3-pyridinyl- 11) 1H-Indole-3-acetamide, α-oxo-N-4-pyridinyl- 12) 1H-Indole-3-acetamide, N-(4-nitrophenyl)-α-oxo- (9CI)

13) 1H-Indole-3-acetamide, N-(4-fluorophenyl)-α-oxo- 14) 1H-Indole-3-acetamide, α-oxo-N-[3-[1-(tetrahydro-2H-pyran-2-yl)-5-[1-(triphenylmethyl)-1H-1,2,4-triazol-3-yl]-1H-indazol-3-yl]phenyl]-

15) 1H-Indole-3-acetamide, α-oxo-N-[3-[5-(1H-1,2,4-triazol-3-yl)-1H-indazol-3-yl]phenyl]-

16) 1H-Indole-3-acetamide, N-[2-[[2-(dimethylamino)ethyl]methylamino]-4-methyl-6-quinolinyl]-α-oxo- 17) 1H-Indole-3-acetamide, N-[2-(4-ethyl-1-piperazinyl)-4-methyl-6-quinolinyl]-α-oxo- 18) 1H-Indole-3-acetamide, α-oxo-N-[3-[1-(tetrahydro-2H-pyran-2-yl)-5-[1-(triphenylmethyl)-1H-1,2,4-triazol-3-yl]-1H-indazol-3-yl]phenyl]-

19) 1H-Indole-3-acetamide, α-oxo-N-[3-[5-(1H-1,2,4-triazol-3-yl)-1H-indazol-3-yl]phenyl]-

20) 1H-Indole-3-acetamide, α-oxo-N-[3-[1-(tetrahydro-2H-pyran-2-yl)-5-[1-(triphenylmethyl)-1H-1,2,4-triazol-3-yl]-1H-indazol-3-yl]phenyl]-

21) 1H-Indole-3-acetamide, α-oxo-N-[3-[5-(1H-1,2,4-triazol-3-yl)-1H-indazol-3-yl]phenyl]-

22) Benzoic acid, 3-[(1H-indol-3-yloxoacetyl)amino]-, methyl ester 23) 1H-Indole-3-acetamide, α-oxo-N-4-pyridinyl- 24) 1H-Indole-3-acetamide, N-[3-[4'-amino-2'-[(3,4,5-trimethoxyphenyl)amino][2,5'-bithiazol]-4-yl]phenyl]-α-oxo- 25) 1H-Indole-3-acetamide, N-[5-(1-methylethyl)-2-thiazolyl]-α-oxo- 26) 1H-Indole-3-acetamide, 5-hydroxy-α-oxo-N-4-pyridinyl- 27) 1H-Indole-3-acetamide, N-[3-(1-methyl-4-piperidinyl)-1H-indol-5-yl]-α-oxo- 28) Benzoic acid, 3-[(1H-indol-3-yloxoacetyl)amino]-, methyl ester 29) 1H-Indole-3-acetamide, α-oxo-N-phenyl- 30) 1H-Indole-3-acetamide, 5-chloro-α-oxo-N-phenyl- 31) 1H-Indole-3-acetamide, 5-nitro-α-oxo-N-phenyl- 32) 1H-Indole-3-acetamide, N-(4-methoxyphenyl)-α-oxo- 33) 1H-Indole-3-acetamide, 5-chloro-N-(4-methoxyphenyl)-α-oxo- 34) 1H-Indole-3-acetamide, N-(4-methoxyphenyl)-5-nitro-α-oxo- 35) 1H-Indole-3-acetamide, N-(4-hydroxyphenyl)-α-oxo- (9CI)

36) 1H-Indole-3-acetamide, 5-chloro-N-(4-hydroxyphenyl)-α-oxo- 37) 1H-Indole-3-acetamide, N-(4-hydroxyphenyl)-5-nitro-α-oxo- 38) 1H-Indole-3-acetamide, α-oxo-N-3-pyridinyl- 39) 1H-Indole-3-acetamide, N-1H-imidazol-2-yl-α-oxo- 40) 1H-Indole-3-acetamide, N-1H-imidazol-2-yl-α-oxo-, monohydrochloride ● HCl 41) 1H-Indole-3-acetamide, N-(2,6-dichlorophenyl)-α-oxo- 42) 1H-Indole-3-acetamide, 5-chloro-N-(2,6-dichlorophenyl)-α-oxo- 43) 1H-Indole-3-acetamide, N-(2,6-dichlorophenyl)-5-methoxy-α-oxo- 44) 1H-Indole-3-acetamide, 5-bromo-N-(2,6-dichlorophenyl)-α-oxo- 45) 1H-Indole-3-acetamide, N-(2,6-dichlorophenyl)-5-nitro-α-oxo- 46) 1H-Indole-3-acetamide, α-oxo-N-(1,2,3,4-tetrahydro-2,4-dioxo-5-pyrimidinyl)-

47) 1H-Indole-3-acetamide, 5-bromo-α-oxo-N-(1,2,3,4-tetrahydro-2,4-dioxo-5-pyrimidinyl)-

48) 1H-Indole-3-acetamide, 5-nitro-α-oxo-N-(1,2,3,4-tetrahydro-2,4-dioxo-5-pyrimidinyl)-

49) 1H-Indole-3-acetamide, α-oxo-N-phenyl- 50) 1H-Indole-3-acetamide, 5-acetyl-α-oxo-N-phenyl- 51) Indole-3-glyoxylanilide, 5-methoxy- 52) Indole-3-glyoxylamide, 5-(benzyloxy)-N-(4-methyl-2-pyridyl)-

53) Indole-3-glyoxylamide, 5-(benzyloxy)-N-2-pyridyl-

54) Anthranilic acid, N-(indol-3-ylglyoxyloyl)-

55) Benzoic acid, p-(2-indol-3-ylglyoxylamido)-

56) Indole-3-glyoxylanilide, 4'-acetyl-

57) Benzoic acid, m-(2-indol-3-ylglyoxylamido)-

58) 1H-Indole-3-acetamide, α-oxo-N-phenyl- 59) 1H-Indole-3-acetamide, α-oxo-N-phenyl- 60) Indole-3-glyoxylamide, 5-(benzyloxy)-N-2-pyridyl- 61) Indole-3-glyoxylamide, 5-(benzyloxy)-N-3-pyridyl- 62) Indole-3-glyoxylamide, 5-(benzyloxy)-N-4-pyridyl- 63) Indole-3-glyoxylanilide, 5-(benzyloxy)-

64) 1H-Indole-3-acetamide, α-oxo-N-[3-[(1,3,3-trimethyl-6-azabicyclo[3.2.1]oct-6-yl)sulfonyl]phenyl]-

65) 1H-Indole-3-acetamide, α-oxo-N-(5,6,7,8-tetrahydro-1-naphthalenyl)- (9CI) (CA INDEX NAME)

66) 1H-Indole-3-acetamide, N-[2-[[(3-methylphenyl)amino]carbonyl]phenyl]-α-oxo- 67) 1H-Indole-3-acetamide, α-oxo-N-4H-1,2,4-triazol-4-yl- 68) 1H-Indole-3-acetamide, N-(2-methoxy-3-dibenzofuranyl)-α-oxo- 69) 1H-Indole-3-acetamide, α-oxo-N-(4,5,6,7-tetrahydro-2-benzothiazolyl)-

70) 1H-Indole-3-acetamide, α-oxo-N-[2-[[tricyclo[3.3.1.1 3,7]dec-1-ylamino]carbonyl]phenyl]-

71) 1H-Indole-3-acetamide, N-(1-cyclohexyl-1H-benzimidazol-5-yl)-α-oxo- 72) 1H-Indole-3-acetamide, N-(4-bromo-2,6-dimethylphenyl)-α-oxo- 73) 1H-Indole-3-acetamide, N-3-dibenzofuranyl-α-oxo-

FIGURE 1N

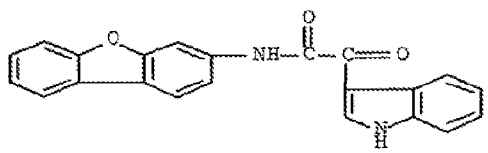

74) 1H-Indole-3-acetamide, N-[2-chloro-5-(trifluoromethyl)phenyl]-α-oxo-

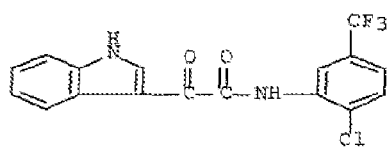

75) 1H-Indole-3-acetamide, N-(3-cyanobenzo[b]thien-2-yl)-α-oxo-

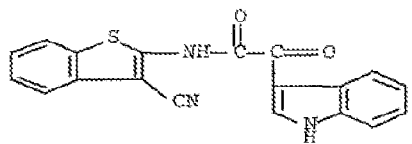

76) Benzo[b]thiophene-3-carboxylic acid, 2-[(1H-indol-3-yloxoacetyl)amino]-, ethyl ester

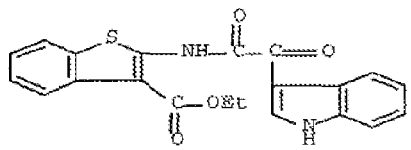

77) 1H-Indole-3-acetamide, α-oxo-N-[3-(trifluoromethyl)phenyl]-

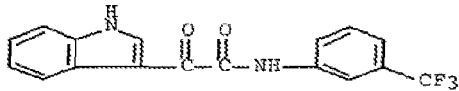

78) 1H-Indole-3-acetamide, N-(3-cyano-4,5,6,7-tetrahydrobenzo[b]thien-2-yl)-α-oxo-

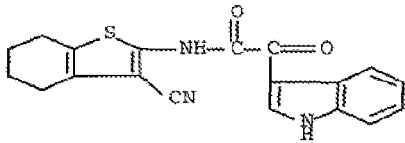

79) Benzo[b]thiophene-3-carboxylic acid, 4,5,6,7-tetrahydro-2-[(1H-indol-3-yloxoacetyl)amino]-, ethyl ester 80) 1H-Indole-3-acetamide, N-(2-methoxyphenyl)-α-oxo- 81) 1H-Indole-3-acetamide, N-1-naphthalenyl-α-oxo- 82) Benzoic acid, 4-[(1H-indol-3-yloxoacetyl)amino]-, methyl ester 83) 1H-Indole-3-acetamide, N-(4-methylphenyl)-α-oxo- 84) 1H-Indole-3-acetamide, N-(3,4-dimethylphenyl)-α-oxo- 85) 1H-Indole-3-acetamide, α-oxo-N-2-thiazolyl- 86) 1H-Indole-3-acetamide, N-naphtho[1,8-cd]-1,2-dithiol-5-yl-α-oxo- 87) 1H-Indole-3-acetamide, N-(4-iodophenyl)-α-oxo- 88) 1H-Indole-3-acetamide, N-(3-methylphenyl)-α-oxo- 89) 1H-Indole-3-acetamide, N-(2-methylphenyl)-α-oxo- 90) 1H-Indole-3-acetamide, N-(4-bromophenyl)-α-oxo- 91) 1H-Indole-3-acetamide, N-(3-chlorophenyl)-α-oxo- 92) 1H-Indole-3-acetamide, N-(4-ethoxyphenyl)-α-oxo- 93) 1H-Indole-3-acetamide, N-(2-ethylphenyl)-α-oxo- 94) 1H-Indole-3-acetamide, 5-bromo-N-(4-fluorophenyl)-α-oxo- 95) 2-indol-3-yl-2-oxo-N-p-tolyl-acetamide 96) 2-(5-bromo-1H-indol-3-yl)-N-(2,4-dioxo-1,2,3,4-tetrahydro-pyrimidin-5-yl)-2-oxo-acetamide 97) N-(2,4-dioxo-1,2,3,4-tetrahydro-pyrimidin-5-yl)-2-(5-nitro-1H-indol-3-yl)-2-oxo-acetamide

MODULATORS OF ATP-BINDING CASSETTE TRANSPORTERS

CROSS-REFERENCE TO RELATED APPLICATIONS

This application claims the benefit under 35 U.S.C. §119 to U.S. Provisional application Ser. No. 60/661,310, filed Mar. 11, 2005 and entitled "MODULATORS OF ATP-BINDING CASSETTE TRANSPORTERS", and U.S. Provisional application Ser. No. 60/669,174, filed on Apr. 7, 2005 and entitled "MODULATORS OF ATP-BINDING CASSETTE TRANSPORTERS". The entire contents of each of the above priority application are incorporated herein by reference.

TECHNICAL FIELD OF THE INVENTION

The present invention relates to modulators of ATP-Binding Cassette ("ABC") transporters or fragments thereof, including Cystic Fibrosis Transmembrane Conductance Regulator ("CFTR"), compositions thereof, and methods therewith. The present invention also relates to methods of treating ABC transporter mediated diseases using such modulators.

BACKGROUND OF THE INVENTION

ABC transporters are a family of membrane transporter proteins that regulate the transport of a wide variety of pharmacological agents, potentially toxic drugs, and xenobiotics, as well as anions. ABC transporters are homologous membrane proteins that bind and use cellular adenosine triphosphate (ATP) for their specific activities. Some of these transporters were discovered as multidrug resistance proteins (like the MDR1-P glycoprotein, or the multidrug resistance protein, MRP1), defending malignant cancer cells against chemotherapeutic agents. To date, 48 ABC Transporters have been identified and grouped into 7 families based on their sequence identity and function.

ABC transporters regulate a variety of important physiological roles within the body and provide defense against harmful environmental compounds. Because of this, they represent important potential drug targets for the treatment of diseases associated with defects in the transporter, prevention of drug transport out of the target cell, and intervention in other diseases in which modulation of ABC transporter activity may be beneficial.

One member of the ABC transporter family commonly associated with disease is the cAMP/ATP-mediated anion channel, CFTR. CFTR is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeate of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in Cystic Fibrosis ("CF"), the most common fatal genetic disease in humans. Cystic Fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia leads to reduced apical anion secretion causing an imbalance in ion and fluid transport. The resulting decrease in anion transport contributes to enhance mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, >1000 disease causing mutations in the CF gene have been identified (http://www.genet.sickkids.on.ca/cftr/). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease.

The deletion of residue 508 in ? F508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ? F508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ? F508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$—$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and Cl– channels expressed on the basolateral surface of the cell. Secondary active transport of chloride from the luminal side leads to the accumulation of intracellular chloride, which can then passively leave the cell via Cl⁻ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

In addition to Cystic Fibrosis, modulation of CFTR activity may be beneficial for other diseases not directly caused by mutations in CFTR, such as secretory diseases and other protein folding diseases mediated by CFTR. These include, but are not limited to, chronic obstructive pulmonary disease (COPD), dry eye disease, and Sjögren's Syndrome.

COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimized periciliary fluid viscosity. This would lead to enhanced mucociliary clearance and a reduction in the symptoms associated with COPD. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as Cystic Fibrosis and Sjögrens's syndrome. Increasing anion secretion via CFTR would enhance fluid transport from the corneal endothelial cells and secretory glands surrounding the eye to increase corneal hydration. This would help to alleviate the symptoms associated with dry eye disease. Sjögrens's syndrome is an autoimmune disease in which the immune system attacks moisture-producing glands throughout the body, including the eye, mouth, skin, respiratory tissue, liver, vagina, and gut. Symptoms, include, dry eye, mouth, and vagina, as well as lung disease. The disease is also associated with rheumatoid arthritis, systemic lupus, systemic sclerosis, and polymypositis/dermatomyositis. Defective protein trafficking is believed to cause the disease, for which treatment options are limited. Modulators of CFTR activity may hydrate the various organs afflicted by the disease and help to elevate the associated symptoms.

As discussed above, it is believed that the deletion of residue 508 in ? F508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery, has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)]. The diseases associated with the first class of ER malfunction are Cystic fibrosis (due to misfolded ΔF508-CFTR as discussed above), Hereditary emphysema (due to a1-antitrypsin; non Piz variants), Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses (due to Lysosomal processing enzymes), Sandhof/Tay-Sachs (due to β-Hexosaminidase), Crigler-Najjar type II (due to UDP-glucuronyl-sialyc-transferase), Polyendocrinopathy/Hyperinsulemia, Diabetes mellitus (due to Insulin receptor), Laron dwarfism (due to Growth hormone receptor), Myleoperoxidase deficiency, Primary hypoparathyroidism (due to Preproparathyroid hormone), Melanoma (due to Tyrosinase). The diseases associated with the latter class of ER malfunction are Glycanosis CDG type 1, Hereditary emphysema (due to a1-Antitrypsin (PiZ variant), Congenital hyperthyroidism, Osteogenesis imperfecta (due to Type I, II, IV procollagen), Hereditary hypofibrinogenemia (due to Fibrinogen), ACT deficiency (due to a1-Antichymotrypsin), Diabetes insipidus (DI), Neurophyseal DI (due to Vasopvessin hormone/V2-receptor), Neprogenic DI (due to Aquaporin II), Charcot-Marie Tooth syndrome (due to Peripheral myelin protein 22), Perlizaeus-Merzbacher disease, neurodegenerative diseases such as Alzheimer's disease (due to βAPP and presenilins), Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease (due to lysosomal α-galactosidase A) and Straussler-Scheinker syndrome (due to Prp processing defect).

In addition to up-regulation of CFTR activity, reducing anion secretion by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Although there are numerous causes of diarrhea, the major consequences of diarrheal diseases, resulting from excessive chloride transport are common to all, and include dehydration, acidosis, impaired growth and death.

Acute and chronic diarrheas represent a major medical problem in many areas of the world. Diarrhea is both a significant factor in malnutrition and the leading cause of death (5,000,000 deaths/year) in children less than five years old.

Secretory diarrheas are also a dangerous condition in patients of acquired immunodeficiency syndrome (AIDS) and chronic inflammatory bowel disease (IBD). 16 million travelers to developing countries from industrialized nations every year develop diarrhea, with the severity and number of cases of diarrhea varying depending on the country and area of travel.

Diarrhea in barn animals and pets such as cows, pigs and horses, sheep, goats, cats and dogs, also known as scours, is a major cause of death in these animals. Diarrhea can result from any major transition, such as weaning or physical movement, as well as in response to a variety of bacterial or viral infections and generally occurs within the first few hours of the animal's life.

The most common diarrheal causing bacteria is enterotoxogenic *E-coli* (ETEC) having the K99 pilus antigen. Common viral causes of diarrhea include rotavirus and coronavirus. Other infectious agents include *cryptosporidium, giardia lamblia*, and *salmonella*, among others.

Symptoms of rotaviral infection include excretion of watery feces, dehydration and weakness. Coronavirus causes a more severe illness in the newborn animals, and has a higher mortality rate than rotaviral infection. Often, however, a young animal may be infected with more than one virus or with a combination of viral and bacterial microorganisms at one time. This dramatically increases the severity of the disease.

Accordingly, there is a need for modulators of an ABC transporter activity, and compositions thereof, that can be used to modulate the activity of the ABC transporter in the cell membrane of a mammal.

There is a need for methods of treating ABC transporter mediated diseases using such modulators of ABC transporter activity.

There is a need for methods of modulating an ABC transporter activity in an ex vivo cell membrane of a mammal.

There is a need for modulators of CFTR activity that can be used to modulate the activity of CFTR in the cell membrane of a mammal.

There is a need for methods of treating CFTR-mediated diseases using such modulators of CFTR activity.

There is a need for methods of modulating CFTR activity in an ex vivo cell membrane of a mammal.

SUMMARY OF THE INVENTION

It has now been found that compounds of this invention, and pharmaceutically acceptable compositions thereof, are useful as modulators of ABC transporter activity. These compounds have the general formula I:

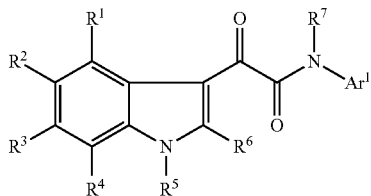

or a pharmaceutically acceptable salt thereof, wherein $R^1$, $R^2$, $R^3$, $R^4$, $R^5$, $R^6$, $R^7$, and $Ar^1$ are described generally and in classes and subclasses below.

These compounds and pharmaceutically acceptable compositions are useful for treating or lessening the severity of a variety of diseases, disorders, or conditions, including, but not limited to, Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker syndrome, COPD, dry-eye disease, and Sjogren's disease.

DETAILED DESCRIPTION OF THE INVENTION

Figure 1:
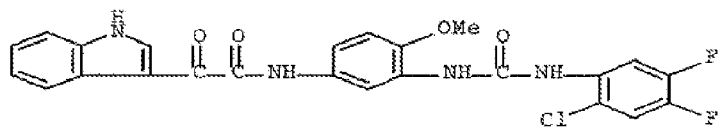
FIG. 1 is a list of compounds that are excluded by the present invention.
Figure 1:
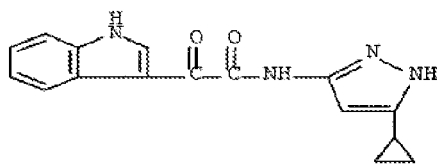
Figure 1:
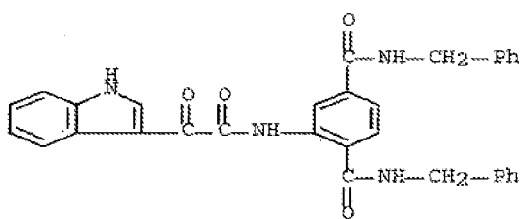
Figure 1:
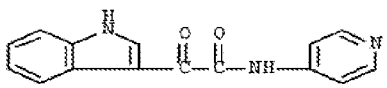
Figure 1A:
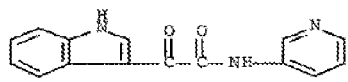
Figure 1A:
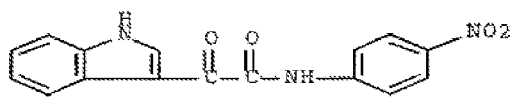
Figure 1A:
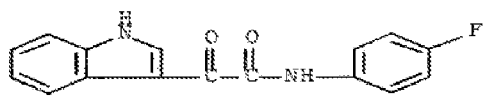
Figure 1A:
Figure 1A:
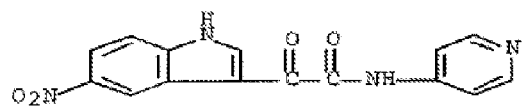
Figure 1A:
Figure 1B:
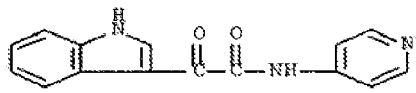
Figure 1B:
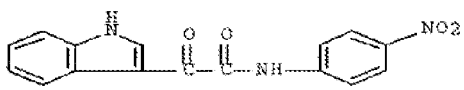
Figure 1B:
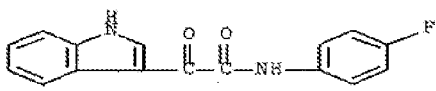
Figure 1B:
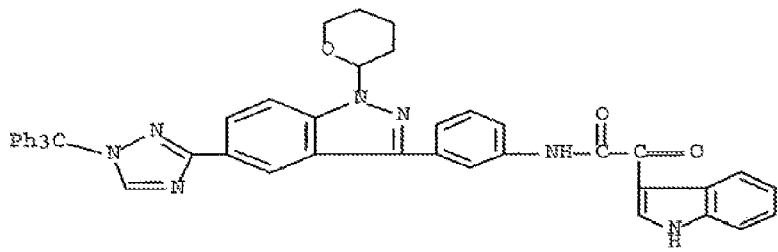
Figure 1B:
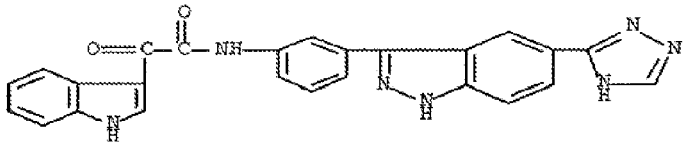
Figure 1C:
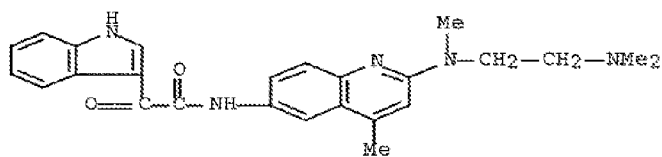
Figure 1C:
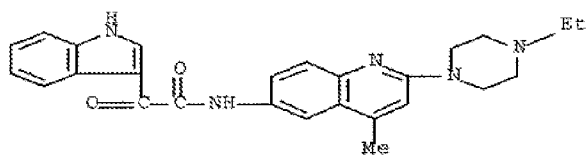
Figure 1C:
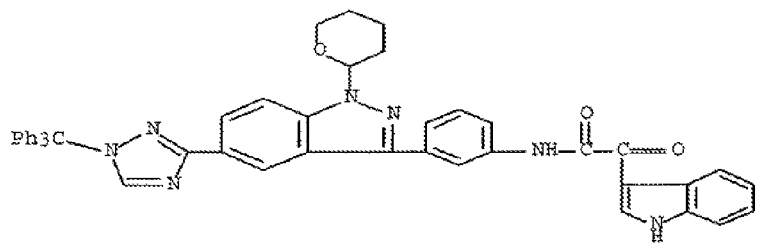
Figure 1C:
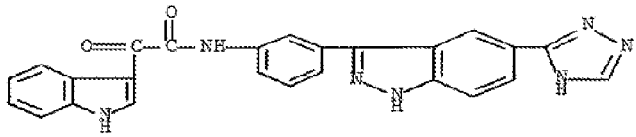
Figure 1D:
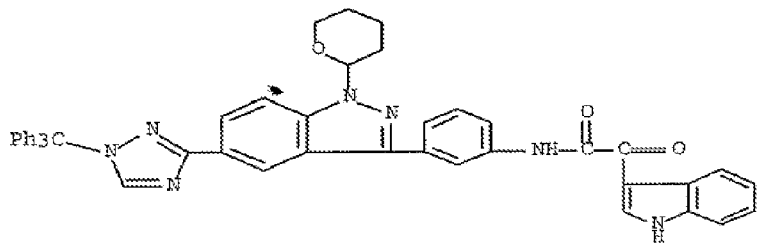
Figure 1D:
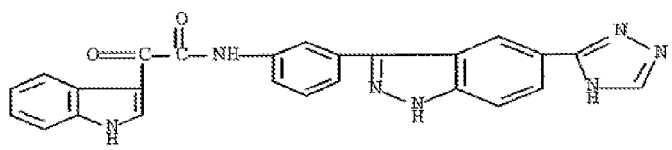
Figure 1D:
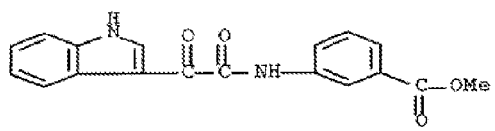
Figure 1D:
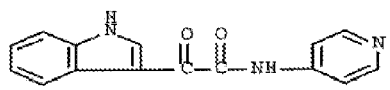
Figure 1E:
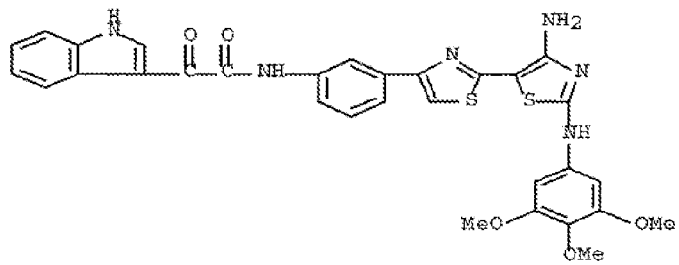
Figure 1E:
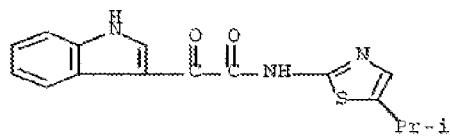
Figure 1E:
Figure 1E:
Figure 1E:
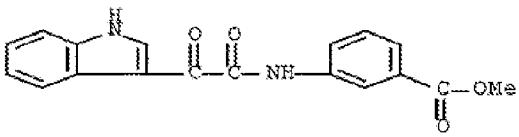
Figure 1F:
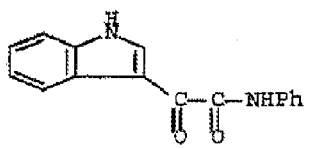
Figure 1F:
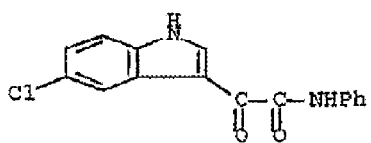
Figure 1F:
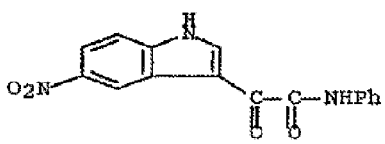
Figure 1F:
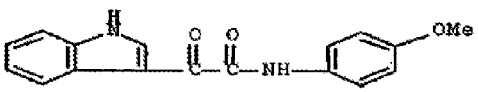
Figure 1F:
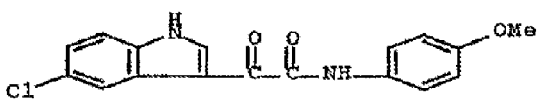
Figure 1F:
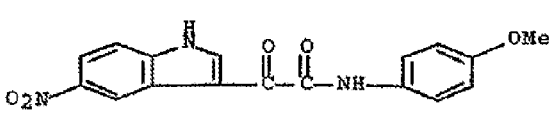
Figure 1G:
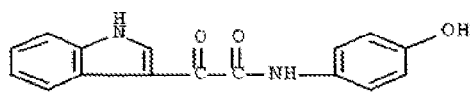
Figure 1G:
Figure 1G:
Figure 1G:
Figure 1G:
Figure 1H:
Figure 1H:
Figure 1H:
Figure 1H:
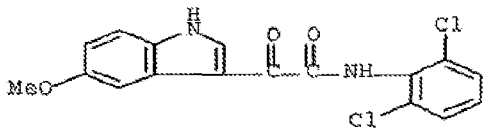
Figure 1H:
Figure 1I:
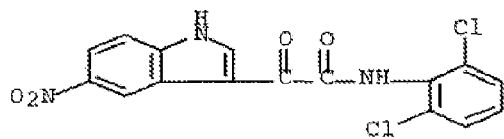
Figure 1I:
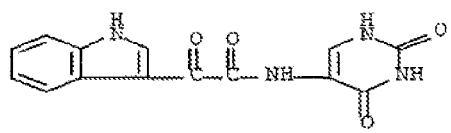
Figure 1I:
Figure 1I:
Figure 1I:
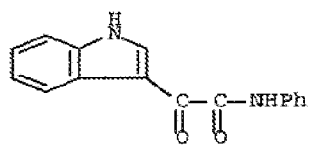
Figure 1J:
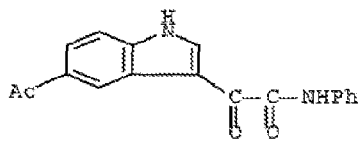
Figure 1J:
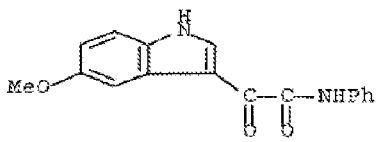
Figure 1J:
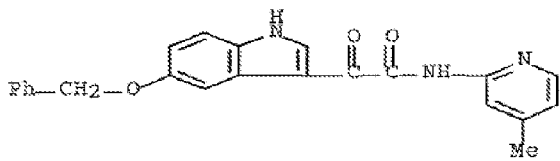
Figure 1J:
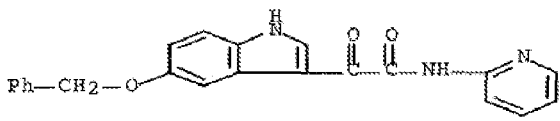
Figure 1J:
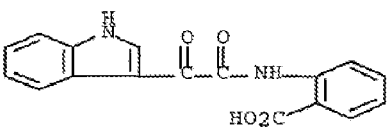
Figure 1J:
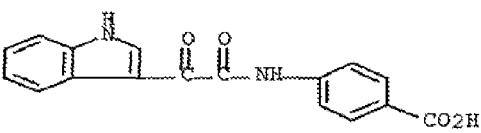
Figure 1K:
Figure 1K:
Figure 1K:
Figure 1K:
Figure 1K:
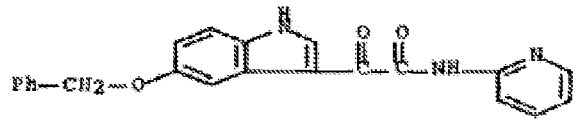
Figure 1K:
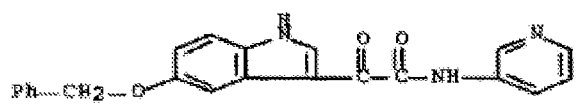
Figure 1L:
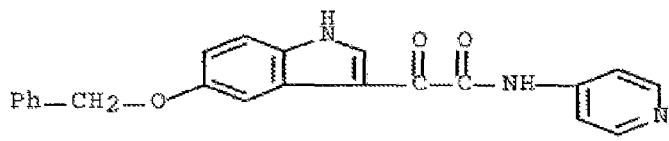
Figure 1L:
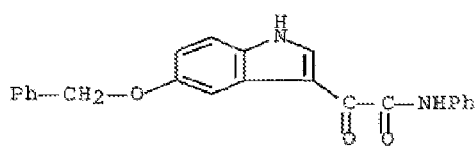
Figure 1L:
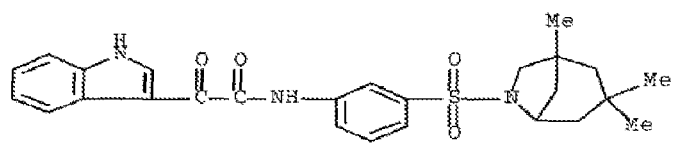
Figure 1L:
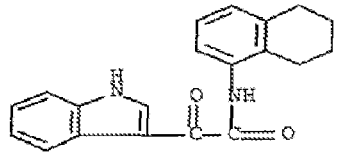
Figure 1L:
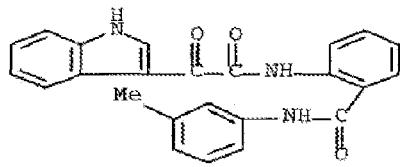
Figure 1L:
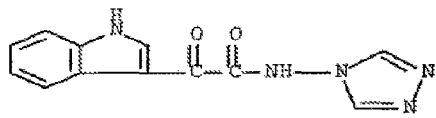
Figure 1M:
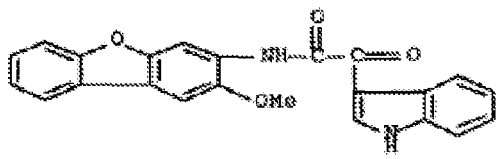
Figure 1M:
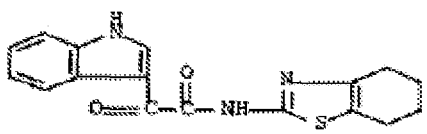
Figure 1M:
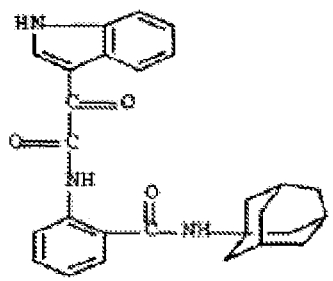
Figure 1M:
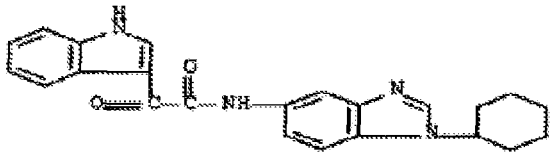
Figure 1M:
Figure 1O:
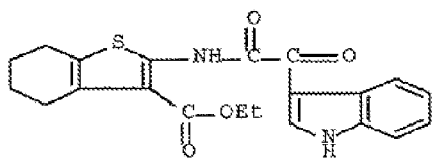
Figure 1O:
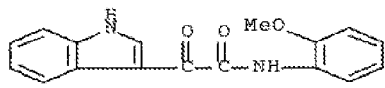
Figure 1O:
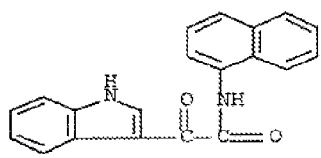
Figure 1O:
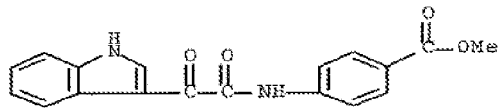
Figure 1O:
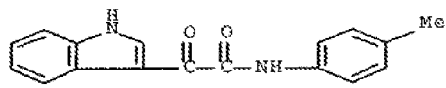
Figure 1O:
Figure 1O:
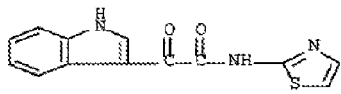
Figure 1P:
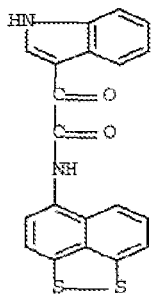
Figure 1P:
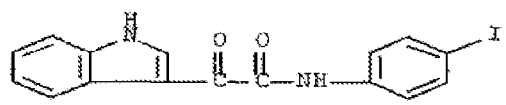
Figure 1P:
Figure 1P:
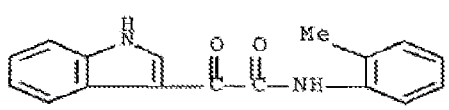
Figure 1P:
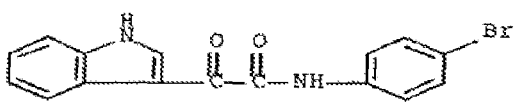
Figure 1P:
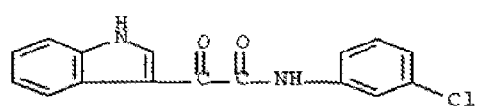
Figure 1Q:
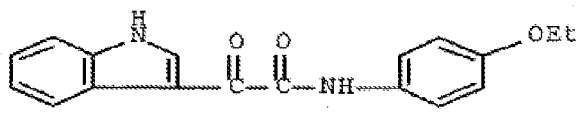
Figure 1Q:
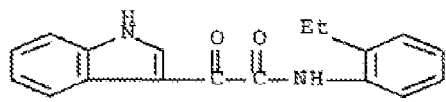
Figure 1Q:
Figure 1Q:
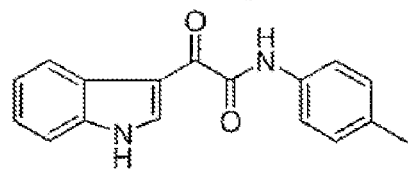
Figure 1Q:
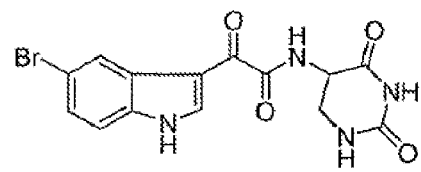
Figure 1Q:
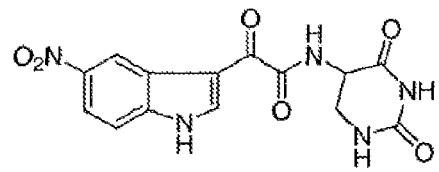

I. General Description of Compounds of the Invention:

The present invention relates to compounds of formula I useful as modulators of ABC transporter activity:

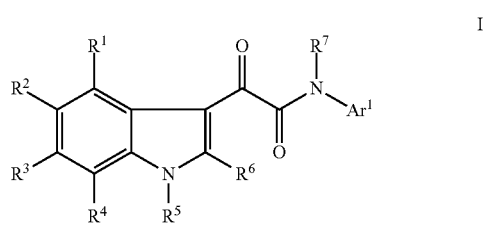

or a pharmaceutically acceptable salt thereof, wherein:

$Ar^1$ is a 5-6 membered aromatic monocyclic ring having 0-4 heteroatoms independently selected from nitrogen, oxygen, or sulfur, wherein said ring is optionally fused to a 5-12 membered monocyclic or bicyclic, aromatic, partially unsaturated, or saturated ring, wherein each ring contains 0-4 heteroatoms independently selected from nitrogen, oxygen, or sulfur, wherein $Ar^1$ has m substituents, each independently selected from —$WR^W$;

W is a bond or is an optionally substituted $C_1$-$C_6$ alkylidene chain wherein up to two methylene units of W are optionally and independently replaced by —CO—, —CS—, —COCO—, —CONR'—, —CONR'NR'—, —$CO_2$—, —OCO—, —NR'$CO_2$—, —O—, —NR'CONR'—, —OCONR'—, —NR'NR'—, —NR'NR'CO—, —NR'CO—, —S—, —SO, —$SO_2$—, —NR'—, —$SO_2$NR'—, NR'$SO_2$—, or —NR'$SO_2$NR'—;

$R^W$ is independently R', halo, $NO_2$, CN, $CF_3$, or $OCF_3$;

m is 0-5;

each of $R^1$, $R^2$, $R^3$, $R^4$, and $R^5$ is independently —X—$R^X$;

X is a bond or is an optionally substituted $C_1$-$C_6$ alkylidene chain wherein up to two methylene units of X are optionally and independently replaced by —CO—, —CS—, —COCO—, —CONR'—, —CONR'NR'—, —$CO_2$—, —OCO—, —NR'$CO_2$—, —O—, —NR'CONR'—, —OCONR'—, —NR'NR'—, —NR'NR'CO—, —NR'CO—, —S—, —SO, —SO$_2$—, —NR'—, —SO$_2$NR'—, NR'SO$_2$—, or —NR'SO$_2$NR'—;

R$^X$ is independently R', halo, NO$_2$, CN, CF$_3$, or OCF$_3$;

R$^6$ is hydrogen, CF$_3$, —OR', —SR', or an optionally substituted C$_{1-6}$ aliphatic group;

R$^7$ is hydrogen or a C$_{1-6}$ aliphatic group optionally substituted with —X—R$^X$;

R' is independently selected from hydrogen or an optionally substituted group selected from a C$_1$-C$_8$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

In certain other embodiments, compounds of formula I are provided:

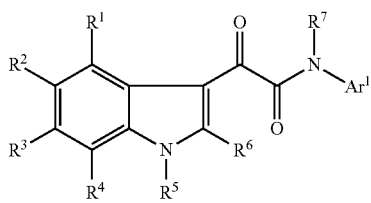

I or a pharmaceutically acceptable salt thereof, wherein:

Ar$^1$ is a 5-6 membered aromatic monocyclic ring having 0-4 heteroatoms independently selected from nitrogen, oxygen, or sulfur, wherein said ring is optionally fused to a 5-12 membered monocyclic or bicyclic, aromatic, partially unsaturated, or saturated ring, wherein each ring contains 0-4 heteroatoms independently selected from nitrogen, oxygen, or sulfur, wherein Ar$^1$ has m substituents each independently selected from —WR$^W$;

W is a bond or is an optionally substituted C$_1$-C$_6$ alkylidene chain wherein up to two methylene units of W are optionally and independently replaced by —CO—, —CS—, —COCO—, —CONR'—, —CONR'NR'—, —CO$_2$—, —OCO—, —NR'CO$_2$—, —O—, —NR'CONR'—, —OCONR'—, —NR'NR', —NR'NR'CO—, —NR'CO—, —S—, —SO, —SO$_2$—, —NR'—, —SO$_2$NR'—, NR'SO$_2$—, or —NR'SO$_2$NR'—;

R$^W$ is independently R', halo, NO$_2$, CN, CF$_3$, or OCF$_3$;

m is 0-5;

each of R$^1$, R$^2$, R$^3$, R$^4$, and R$^5$ is independently —X—R$^X$;

X is a bond or is an optionally substituted C$_1$-C$_6$ alkylidene chain wherein up to two methylene units of X are optionally and independently replaced by —CO—, —CS—, —COCO—, —CONR'—, —CONR'NR'—, —CO$_2$—, —OCO—, —NR'CO$_2$—, —O—, —NR'CONR'—, —OCONR'—, —NR'NR', —NR'NR'CO—, —NR'CO—, —S—, —SO, —SO$_2$—, —NR'—, —SO$_2$NR'—, NR'SO$_2$—, or —NR'SO$_2$NR'—;

R$^X$ is independently R', halo, NO$_2$, CN, CF$_3$, or OCF$_3$;

R$^6$ is hydrogen, CF$_3$, —OR', —SR', or an optionally substituted C$_{1-6}$ aliphatic group;

R$^7$ is hydrogen or a C$_{1-6}$ aliphatic group optionally substituted with —X—R$^X$;

R' is independently selected from hydrogen or an optionally substituted group selected from a C$_1$-C$_8$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur;

provided that the compounds of FIG. 1 are excluded.

2. Compounds and Definitions:

Compounds of this invention include those described generally above, and are further illustrated by the classes, subclasses, and species disclosed herein. As used herein, the following definitions shall apply unless otherwise indicated.

The term "ABC-transporter" as used herein means an ABC-transporter protein or a fragment thereof comprising at least one binding domain, wherein said protein or fragment thereof is present in vivo or in vitro. The term "binding domain" as used herein means a domain on the ABC-transporter that can bind to a modulator. See, e.g., Hwang, T. C. et al., J. Gen. Physiol. (1998): 111(3), 477-90.

The term "CFTR" as used herein means cystic fibrosis transmembrane conductance regulator or a mutation thereof capable of regulator activity, including, but not limited to, ? F508 CFTR and G551D CFTR (see, e.g., http://www.genet.sickkids.on.ca/cftr/, for CFTR mutations).

The term "modulating" as used herein means increasing or decreasing by a measurable amount.

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic or tricyclic $C_8$-$C_{14}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl. Suitable cycloaliphatic groups include cycloalkyl, bicyclic cycloalkyl (e.g., decalin), bridged bicycloalkyl such as norbornyl or [2.2.2]bicyclo-octyl, or bridged tricyclic such as adamantyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members is an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloaliphatic" and "haloalkoxy" means aliphatic or alkoxy, as the case may be, substituted with one or more halo atoms. The term "halogen" or "halo" means F, Cl, Br, or I. Examples of haloaliphatic include —$CHF_2$, —$CH_2F$, —$CF_3$, —$CF_2$—, or perhaloalkyl, such as, —$CF_2CF_3$.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halo; —$R^o$; —$OR^o$; —$SR^o$; 1,2-methylene-dioxy; 1,2-ethylenedioxy; phenyl (Ph) optionally substituted with $R^o$; —O(Ph) optionally substituted with $R^o$; —$(CH_2)_{1-2}$(Ph), optionally substituted with $R^o$; —CH=CH(Ph), optionally substituted with $R^o$; —$NO_2$; —CN; —$N(R^o)_2$; —$NR^oC(O)R^o$; —$NR^oC(O)N(R^o)_2$; —$NR^oCO_2R^o$; —$NR^oNR^oC(O)R^o$; —$NR^oNR^oC(O)N(R^o)_2$; —$NR^oNR^oCO_2R^o$; —C(O)C(O)$R^o$; —C(O)$CH_2$C(O)$R^o$; —$CO_2R^o$; —C(O)$R^o$; —C(O)N($R^o)_2$; —OC(O)N($R^o)_2$; —S(O)$_2R^o$; —$SO_2N(R^o)_2$; —S(O)$R^o$; —$NR^oSO_2N(R^o)_2$; —$NR^oSO_2R^o$; —C(=S)N($R^o)_2$; —C(=NH)—N($R^o)_2$; or —$(CH_2)_{0-2}NHC(O)R^o$ wherein each independent occurrence of $R^o$ is selected from hydrogen, optionally substituted $C_{1-6}$ aliphatic, an unsubstituted 5-6 membered heteroaryl or heterocyclic ring, phenyl, —O(Ph), or —$CH_2$(Ph), or, notwithstanding the definition above, two independent occurrences of $R^o$, on the same substituent or different substituents, taken together with the atom(s) to which each $R^o$ group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group of $R^o$ are selected from $NH_2$, NH($C_{1-4}$aliphatic), N($C_{1-4}$aliphatic)$_2$, halo, $C_{1-4}$aliphatic, OH, O($C_{1-4}$aliphatic), $NO_2$, CN, $CO_2H$, $CO_2(C_{1-4}$aliphatic), O(halo$C_{1-4}$ aliphatic), or halo$C_{1-4}$aliphatic, wherein each of the foregoing $C_{1-4}$aliphatic groups of $R^o$ is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted $C_{1-6}$ aliphatic. Optional substituents on the aliphatic group of R* are selected from $NH_2$, NH($C_{1-4}$ aliphatic), N($C_{1-4}$ aliphatic)$_2$, halo, $C_{1-4}$ aliphatic, OH, O($C_{1-4}$ aliphatic), $NO_2$, CN, $CO_2H$, $CO_2(C_{1-4}$ aliphatic), O(halo $C_{1-4}$ aliphatic), or halo($C_{1-4}$ aliphatic), wherein each of the foregoing $C_{1-4}$aliphatic groups of R* is unsubstituted.

Optional substituents on the nitrogen of a non-aromatic heterocyclic ring are selected from —R⁺, —N(R⁺)₂, —C(O)R⁺, —CO₂R⁺, —C(O)C(O)R⁺, —C(O)CH₂C(O)R⁺, —SO₂R⁺, —SO₂N(R⁺)₂, —C(=S)N(R⁺)₂, —C(=NH)—N(R⁺)₂, or —NR⁺SO₂R⁺; wherein R⁺ is hydrogen, an optionally substituted $C_{1-6}$ aliphatic, optionally substituted phenyl, optionally substituted —O(Ph), optionally substituted —CH₂(Ph), optionally substituted —(CH₂)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R⁺, on the same substituent or different substituents, taken together with the atom(s) to which each R⁺ group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group or the phenyl ring of R⁺ are selected from NH₂, NH($C_{1-4}$ aliphatic), N($C_{1-4}$ aliphatic)₂, halo, $C_{1-4}$ aliphatic, OH, O($C_{1-4}$ aliphatic), NO₂, CN, CO₂H, CO₂($C_{1-4}$ aliphatic), O(halo $C_{1-4}$ aliphatic), or halo($C_{1-4}$ aliphatic), wherein each of the foregoing $C_{1-4}$ aliphatic groups of R⁺ is unsubstituted.

The term "alkylidene chain" refers to a straight or branched carbon chain that may be fully saturated or have one or more units of unsaturation and has two points of attachment to the rest of the molecule. The term "spirocycloalkylidene" refers to a carbocyclic ring that may be fully saturated or have one or more units of unsaturation and has two points of attachment from the same ring carbon atom to the rest of the molecule.

As detailed above, in some embodiments, two independent occurrences of R° (or R⁺, or any other variable similarly defined herein), are taken together with the atom(s) to which each variable is bound to form a 3-8-membered cycloalkyl, heterocyclyl, aryl, or heteroaryl ring having 0-3 heteroatoms independently selected from nitrogen, oxygen, or sulfur. Exemplary rings that are formed when two independent occurrences of R° (or R⁺, or any other variable similarly defined herein) are taken together with the atom(s) to which each variable is bound include, but are not limited to the following: a) two independent occurrences of R° (or R⁺, or any other variable similarly defined herein) that are bound to the same atom and are taken together with that atom to form a ring, for example, N(R°)₂, where both occurrences of R° are taken together with the nitrogen atom to form a piperidin-1-yl, piperazin-1-yl, or morpholin-4-yl group; and b) two independent occurrences of R° (or R⁺, or any other variable similarly defined herein) that are bound to different atoms and are taken together with both of those atoms to form a ring, for example where a phenyl group is substituted with two occurrences of OR°

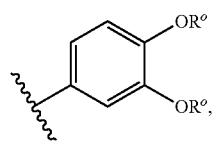

these two occurrences of R° are taken together with the oxygen atoms to which they are bound to form a fused 6-membered oxygen containing ring:

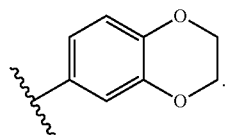

It will be appreciated that a variety of other rings can be formed when two independent occurrences of R° (or R⁺, or any other variable similarly defined herein) are taken together with the atom(s) to which each variable is bound and that the examples detailed above are not intended to be limiting.

A substituent bond in, e.g., a bicyclic ring system, as shown below, means that the substituent can be attached to any substitutable ring atom on either ring of the bicyclic ring system:

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a ¹³C- or ¹⁴C-enriched carbon are within the scope of this invention. Such compounds are useful, for example, as analytical tools or probes in biological assays.

3. Description of Exemplary Compounds:

In some embodiments of the present invention, Ar¹ is selected from:

a-i a-ii wherein ring $A_1$ 5-6 membered aromatic monocyclic ring having 0-4 heteroatoms independently selected from nitrogen, oxygen, or sulfur; or $A_1$ and $A_2$, together, is an 8-14 membered aromatic, bicyclic or tricyclic ring, wherein each ring contains 0-4 heteroatoms independently selected from nitrogen, oxygen, or sulfur.

In some embodiments, $A_1$ is an optionally substituted 6 membered aromatic ring having 0-4 heteroatoms, wherein said heteroatom is nitrogen. In some embodiments, $A_1$ is an optionally substituted phenyl. Or, $A_1$ is an optionally substituted pyridyl, pyrimidinyl, pyrazinyl or triazinyl.

In some embodiments, $A_1$ is an optionally substituted 5-membered aromatic ring having 0-3 heteroatoms, wherein said heteroatom is nitrogen, oxygen, or sulfur. In some embodiments, $A_1$ is an optionally substituted 5-membered aromatic ring having 1-2 nitrogen atoms.

In some embodiments, $A_2$ is an optionally substituted 6 membered aromatic ring having 0-4 heteroatoms, wherein said heteroatom is nitrogen. In some embodiments, $A_2$ is an optionally substituted phenyl. Or, $A_2$ is an optionally substituted pyridyl, pyrimidinyl, pyrazinyl, or triazinyl.

In some embodiments, $A_2$ is an optionally substituted 5-membered aromatic ring having 0-3 heteroatoms, wherein said heteroatom is nitrogen, oxygen, or sulfur. In some embodiments, $A_2$ is an optionally substituted 5-membered aromatic ring having 1-2 nitrogen atoms. In certain embodiments, $A_2$ is an optionally substituted pyrollyl In some embodiments, ring $A_2$ is selected from:

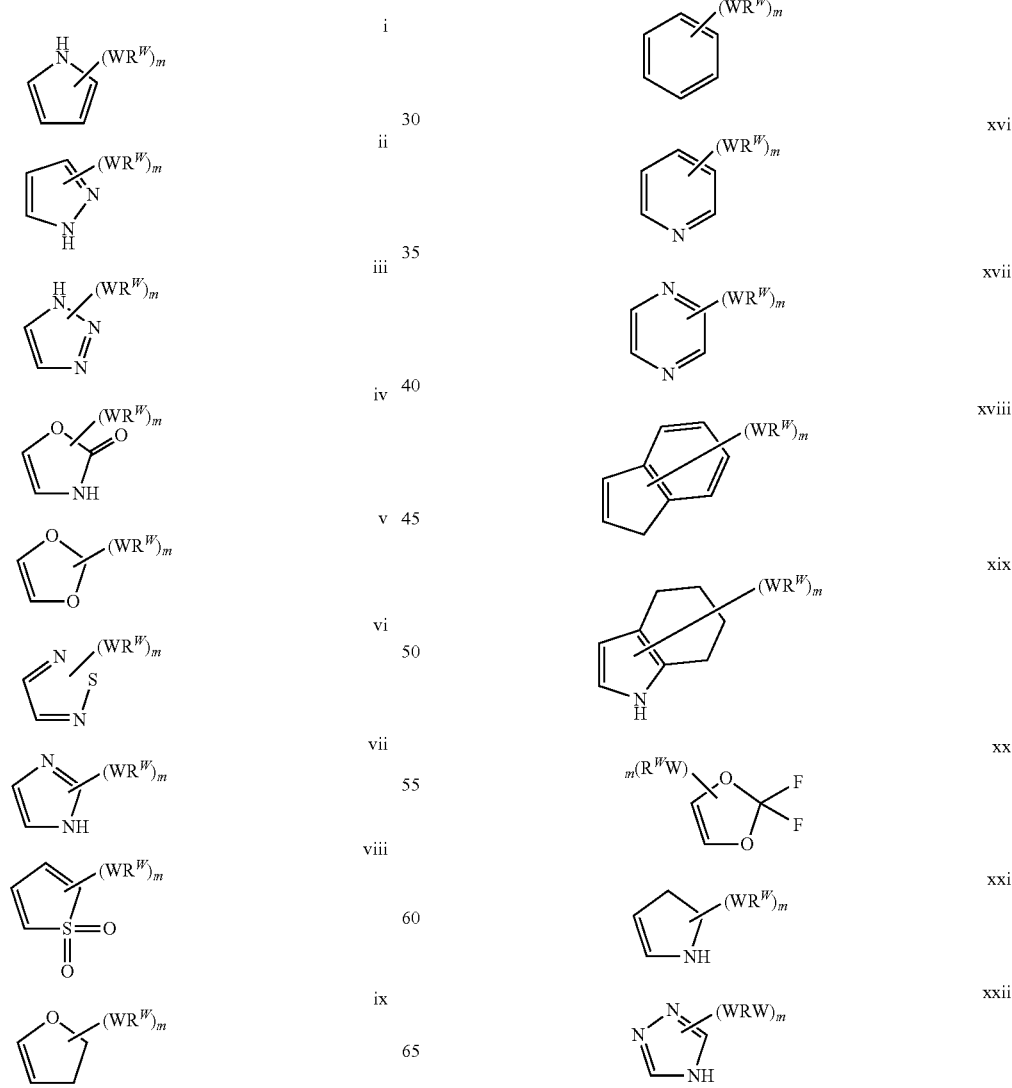

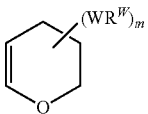

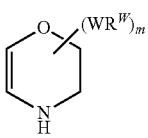

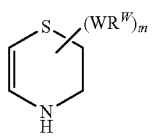

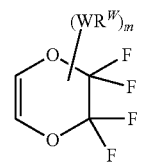

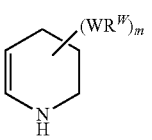

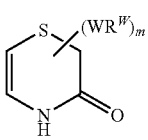

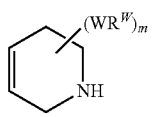

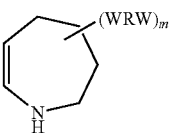

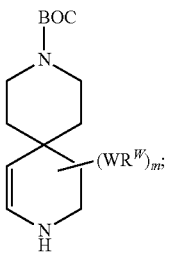

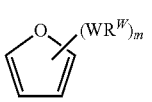

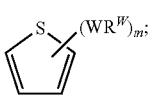

wherein ring $A_2$ is fused to ring $A_1$ through two adjacent carbon ring atoms.

In other embodiments, W is a bond or is an optionally substituted $C_{1-6}$ alkylidene chain wherein one or two non-adjacent methylene units are optionally and independently replaced by O, NR', S, SO, $SO_2$, or COO, CO, $SO_2NR'$, NR'$SO_2$, C(O)NR', NR'C(O), OC(O), OC(O)NR' and $R^W$ is R' or halo. In still other embodiments, each occurrence of $WR^W$ is independently —$C_{1-3}$alkyl, —$C_{1-3}$ perhaloalkyl, —O($C_{1-3}$alkyl), —$CF_3$, —$OCF_3$, —$SCF_3$, —F, —Cl, —Br, or —COOR', —COR', —O($CH_2$)$_2$N(R')(R'), —O($CH_2$)N (R')(R'), —CON(R')(R'), —($CH_2$)$_2$OR', —($CH_2$)OR', optionally substituted monocyclic or bicyclic aromatic ring, optionally substituted arylsulfone, optionally substituted 5-membered heteroaryl ring, —N(R')(R'), —($CH_2$)$_2$N(R') (R'), or —($CH_2$)N(R')(R').

In some embodiments, m is 0. Or, m is 1. Or, m is 2. In some embodiments, m is 3. In yet other embodiments, m is 4.

In one embodiment, $R^5$ is X—$R^X$. In some embodiments, $R^5$ is hydrogen. Or, $R^5$ is an optionally substituted $C_{1-8}$ aliphatic group. In some embodiments, $R^5$ is optionally substituted $C_{1-4}$ aliphatic. Or $R^5$ is methyl.

In one embodiment of the present invention, $R^1$, $R^2$, $R^3$, and $R^4$ are simultaneously hydrogen. In another embodiment, $R^5$ and $R^6$ are both simultaneously hydrogen. In yet another embodiment, $R^5$, $R^6$, and $R^7$ are simultaneously hydrogen.

In another embodiment of the present invention, $R^1$, $R^2$, $R^3$, $R^4$, and $R^5$ are simultaneously hydrogen. In another embodiment of the present invention, $R^1$, $R^2$, $R^3$, $R^4$, $R^5$ and $R^6$ are simultaneously hydrogen In another embodiment of the present invention, $R^2$ is X—$R^X$, wherein X is —$SO_2NR'$—, and $R^X$ is R'.

In some embodiments, X is a bond or is an optionally substituted $C_{1-6}$ alkylidene chain wherein one or two non-adjacent methylene units are optionally and independently replaced by O, NR', S, $SO_2$, COO, or CO, and $R^X$ is R' or halo. In still other embodiments, each occurrence of $XR^X$ is independently —$C_{1-3}$alkyl, —O($C_{1-3}$alkyl), —$CF_3$, —$OCF_3$, —$SCF_3$, —F, —Cl, —Br, —OH, —COOR', —COR', —O($CH_2$)$_2$N(R')(R'), —O($CH_2$)N(R')(R'), —CON(R')(R'), —($CH_2$)$_2$OR', —($CH_2$)OR', optionally substituted phenyl, —N(R')(R'), —($CH_2$)$_2$N(R')(R'), or —($CH_2$)N(R')(R').

In some embodiments, $R^7$ is hydrogen. In certain other embodiment, $R^7$ is $C_{1-4}$ straight or branched aliphatic.

In some embodiments, $R^W$ is selected from halo, cyano, $CF_3$, $CHF_2$, $OCHF_2$, Me, Et, CH(Me)$_2$, CHMeEt, n-propyl, t-butyl, n-butyl, isoprenyl, OMe, OEt, OPh, O-fluorophenyl, O-difluorophenyl, O-2-methoxyphenyl, 2,4-dichlorophenyloxy, O-tolyl, O-benzyl, SMe, $SCF_3$, $SCHF_2$, SEt, $CH_2CN$, $NH_2$, NHMe, N(Me)$_2$, NHEt, N(Et)$_2$, C(O)$CH_3$, C(O)Ph, C(O)$NH_2$, SPh, $SO_2$—NHpyridyl, $SO_2NH_2$, $SO_2$Ph, $SO_2$NHPh, $SO_2$—N-morpholino, $SO_2$—N-pyrrolidyl, N-pyrrolyl, N-morpholino, 1-piperidyl, phenyl, benzyl, (cyclohexyl-methylamino)methyl, 4-Methyl-2,4-dihydro-pyrazol-3-one-2-yl, benzimidazol-2yl, furan-2-yl, 4-Methyl-4H-[1,2,4]triazol-3-yl, 3-(4'-chlorophenyl)-[1,2,4]oxadiazol-5-yl, NHC(O)Me, NHC(O)Et, NHC(O)Ph, $NHSO_2$Me, 2-indolyl, 5-indolyl, —$CH_2CH_2$OH, —$OCF_3$, O-(2,3-dimethylphenyl), 5-methylfuryl, —$SO_2$—N-piperidyl, 2-tolyl, 3-tolyl, 4-tolyl, O-butyl, $NHCO_2$C(Me)$_3$, $CO_2$C(Me)$_3$, isopropenyl, n-butyl, O-(2,4-dichlorophenyl), $NHSO_2$PhMe, O-(3-chloro-5-trifluoromethyl-2-pyridyl), phenylhydroxymethyl, 2,5-dimethylpyrrolyl, $NHCOCH_2$C(Me)$_3$, O-(2-tert-butyl)phenyl, 2,3-dimethylphenyl, 3,4-dimethylphenyl, 4-hydroxymethyl phenyl, 4-dimethylaminophenyl, 2-trifluoromethylphenyl, 3-trifluoromethylphenyl, 4-trifluoromethylphenyl, 4-cyanomethylphenyl, 4-isobutylphenyl, 3-pyridyl, 4-pyridyl, 4-isopropylphenyl, 3-isopropylphenyl, 2-methoxyphenyl, 3-methoxyphenyl, 4-methoxyphenyl, 3,4- methylenedioxyphenyl, 2-ethoxyphenyl, 3-ethoxyphenyl, 4-ethoxyphenyl, 2-methylthiophenyl, 4-methylthiophenyl, 2,4-dimethoxyphenyl, 2,5-dimethoxyphenyl, 2,6-dimethoxyphenyl, 3,4-dimethoxyphenyl, 5-chloro-2-methoxyphenyl, 2-OCF$_3$-phenyl, 3-trifluoromethoxy-phenyl, 4-trifluoromethoxyphenyl, 2-phenoxyphenyl, 4-phenoxyphenyl, 2-fluoro-3-methoxy-phenyl, 2,4-dimethoxy-5-pyrimidyl, 5-isopropyl-2-methoxyphenyl, 2-fluorophenyl, 3-fluorophenyl, 4-fluorophenyl, 3-cyanophenyl, 3-chlorophenyl, 4-chlorophenyl, 2,3-difluorophenyl, 2,4-difluorophenyl, 2,5-difluorophenyl, 3,4-difluorophenyl, 3,5-difluorophenyl, 3-chloro-4-fluoro-phenyl, 3,5-dichlorophenyl, 2,5-dichlorophenyl, 2,3-dichlorophenyl, 3,4-dichlorophenyl, 2,4-dichlorophenyl, 3-methoxycarbonylphenyl, 4-methoxycarbonyl phenyl, 3-isopropyloxycarbonylphenyl, 3-acetamidophenyl, 4-fluoro-3-methylphenyl, 4-methanesulfinyl-phenyl, 4-methanesulfonyl-phenyl, 4-N-(2-N,N-dimethylaminoethyl)carbamoylphenyl, 5-acetyl-2-thienyl, 2-benzothienyl, 3-benzothienyl, furan-3-yl, 4-methyl-2-thienyl, 5-cyano-2-thienyl, N'-phenylcarbonyl-N-piperazinyl, —NHCO$_2$Et, —NHCO$_2$Me, N-pyrrolidinyl, —NHSO$_2$(CH$_2$)$_2$ N-piperidine, —NHSO$_2$(CH$_2$)$_2$ N-morpholine, —NHSO$_2$(CH$_2$)$_2$N (Me)$_2$, COCH$_2$N(Me)COCH$_2$NHMe, —CO$_2$Et, O-propyl, —CH$_2$CH$_2$NHCO$_2$C(Me)$_3$, hydroxy, aminomethyl, pentyl, adamantyl, cyclopentyl, ethoxyethyl, C(Me)$_2$CH$_2$OH, C(Me)$_2$CO$_2$Et, —CHOHMe, CH$_2$CO$_2$Et, —C(Me)$_2$CH$_2$NHCO$_2$C(Me)$_3$, O(CH$_2$)$_2$OEt, O(CH$_2$)$_2$OH, CO$_2$Me, hydroxymethyl, 1-methyl-1-cyclohexyl, 1-methyl-1-cyclooctyl, 1-methyl-1-cycloheptyl, C(Et)$_2$C(Me)$_3$, C(Et)$_3$, CONHCH$_2$CH(Me)$_2$, 2-aminomethyl-phenyl, ethenyl, 1-piperidinylcarbonyl, ethynyl, cyclohexyl, 4-methylpiperidinyl, —OCO$_2$Me, —C(Me)$_2$CH$_2$NHCO$_2$CH$_2$CH(Me)$_2$, —C(Me)$_2$CH$_2$NHCO$_2$CH$_2$CH$_2$CH$_3$, —C(Me)$_2$CH$_2$NHCO$_2$Et, —C(Me)$_2$CH$_2$NHCO$_2$Me, —C(Me)$_2$CH$_2$NHCO$_2$CH$_2$C(Me)$_3$, —CH$_2$NHCOCF$_3$, —CH$_2$NHCO$_2$C (Me)$_3$, —C(Me)$_2$CH$_2$NHCO$_2$(CH$_2$)$_3$CH$_3$, C(Me)$_2$CH$_2$NHCO$_2$(CH$_2$)$_2$OMe, C(OH)(CF$_3$)$_2$, —C(Me)$_2$CH$_2$NHCO$_2$CH$_2$-tetrahydrofurane-3-yl, C(Me)$_2$CH$_2$O(CH$_2$)$_2$OMe, or 3-ethyl-2,6-dioxopiperidin-3-yl.

In one embodiment, R' is hydrogen.

In one embodiment, R' is a C1-C8 aliphatic group, optionally substituted with up to 3 substituents selected from halo, CN, CF$_3$, CHF$_2$, OCF$_3$, or OCHF$_2$, wherein up to two methylene units of said C1-C8 aliphatic is optionally replaced with —CO—, —CONH(C1-C4 alkyl)-, —CO$_2$—, —OCO—, —N(C1-C4 alkyl)CO$_2$—, —O—, —N(C1-C4 alkyl)CON (C1-C4 alkyl)-, —OCON(C1-C4 alkyl)-, —N(C1-C4 alkyl) CO—, —S—, —N(C1-C4 alkyl)-, —SO$_2$N(C1-C4 alkyl)-, N(C1-C4 alkyl)SO$_2$—, or —N(C1-C4 alkyl)SO$_2$N(C1-C4 alkyl)-.

In one embodiment, R' is a 3-8 membered saturated, partially unsaturated, or fully unsaturated monocyclic ring having 0-3 heteroatoms independently selected from nitrogen, oxygen, or sulfur, wherein R' is optionally substituted with up to 3 substituents selected from halo, CN, CF$_3$, CHF$_2$, OCF$_3$, OCHF$_2$, or C1-C6 alkyl, wherein up to two methylene units of said C1-C6 alkyl is optionally replaced with —CO—, —CONH(C1-C4 alkyl)-, —CO$_2$—, —OCO—, —N(C1-C4 alkyl)CO$_2$—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —SO$_2$N(C1-C4 alkyl)-, N(C1-C4 alkyl) SO$_2$—, or —N(C1-C4 alkyl)SO$_2$N(C1-C4 alkyl)-.

In one embodiment, R' is an 8-12 membered saturated, partially unsaturated, or fully unsaturated bicyclic ring system having 0-5 heteroatoms independently selected from nitrogen, oxygen, or sulfur; wherein R' is optionally substituted with up to 3 substituents selected from halo, CN, CF$_3$, CHF$_2$, OCF$_3$, OCHF$_2$, or C1-C6 alkyl, wherein up to two methylene units of said C1-C6 alkyl is optionally replaced with —CO—, —CONH(C1-C4 alkyl)-, —CO$_2$—, —OCO—, —N(C1-C4 alkyl)CO$_2$—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —SO$_2$N(C1-C4 alkyl)-, N(C1-C4 alkyl)SO$_2$—, or —N(C1-C4 alkyl)SO$_2$N(C1-C4 alkyl)-.

In one embodiment, two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein R' is optionally substituted with up to 3 substituents selected from halo, CN, CF$_3$, CHF$_2$, OCF$_3$, OCHF$_2$, or C1-C6 alkyl, wherein up to two methylene units of said C1-C6 alkyl is optionally replaced with —CO—, —CONH(C1-C4 alkyl)-, —CO$_2$—, —OCO—, —N(C1-C4 alkyl)CO$_2$—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —SO$_2$N(C1-C4 alkyl)-, N(C1-C4 alkyl) SO$_2$—, or —N(C1-C4 alkyl)SO$_2$N(C1-C4 alkyl)-.

According to one embodiment, the present invention provides compounds of formula IIA or formula IIB:

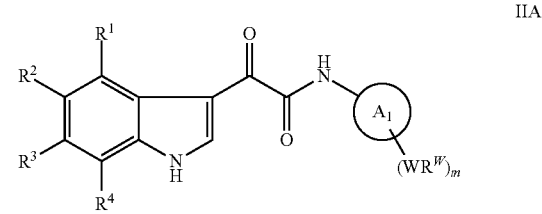

IIA

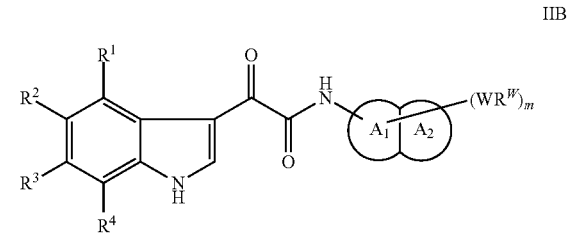

IIB

According to another embodiment, the present invention provides compounds of formula IIIA, formula IIIB, formula IIIC, formula IIID, or formula IIIE:

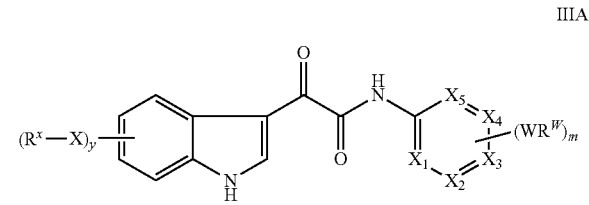

IIIA

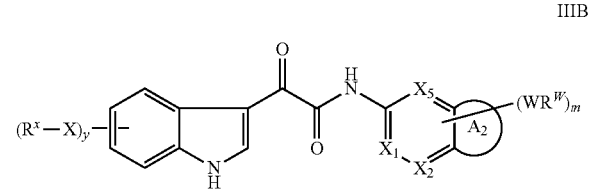

IIIB

-continued

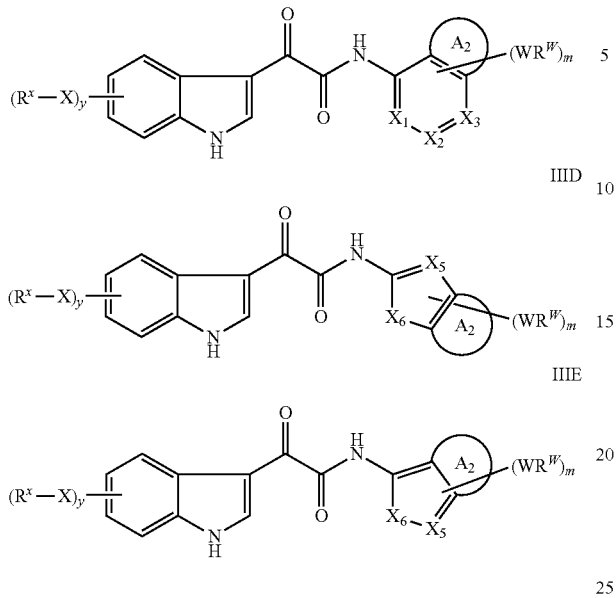

wherein each of $X_1$, $X_2$, $X_3$, $X_4$, and $X_5$ is independently selected from CH or N; and $X_6$ is O, S, or NR'.

In one embodiment, compounds of formula IIIA, formula IIIB, formula IIIC, formula IIID, or formula IIIE have y occurrences of substituent X—$R^X$, wherein y is 0-4. Or, y is 1. Or, y is 2.

In some embodiments of formula IIIA, $X_1$, $X_2$, $X_3$, $X_4$, and $X_5$ taken together with $WR^W$ and m is optionally substituted phenyl.

In some embodiments of formula IIIA, $X_1$, $X_2$, $X_3$, $X_4$, and $X_5$ taken together is an optionally substituted ring selected from:

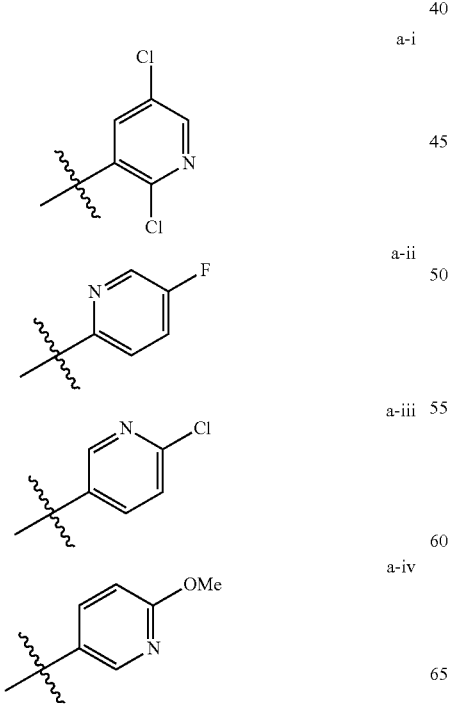

-continued

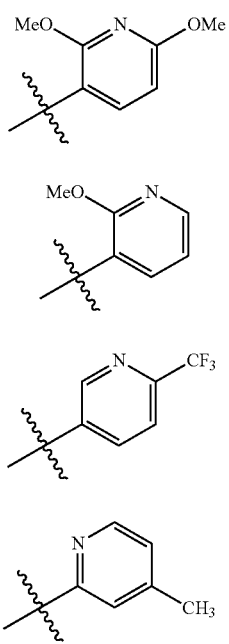

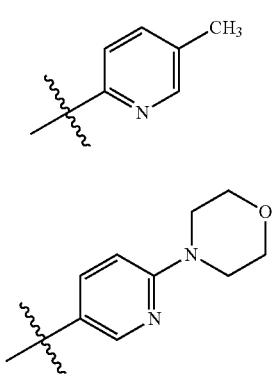

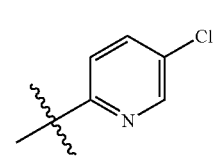

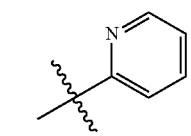

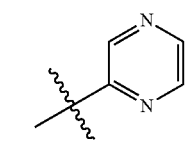

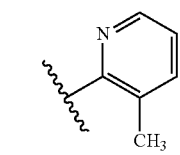

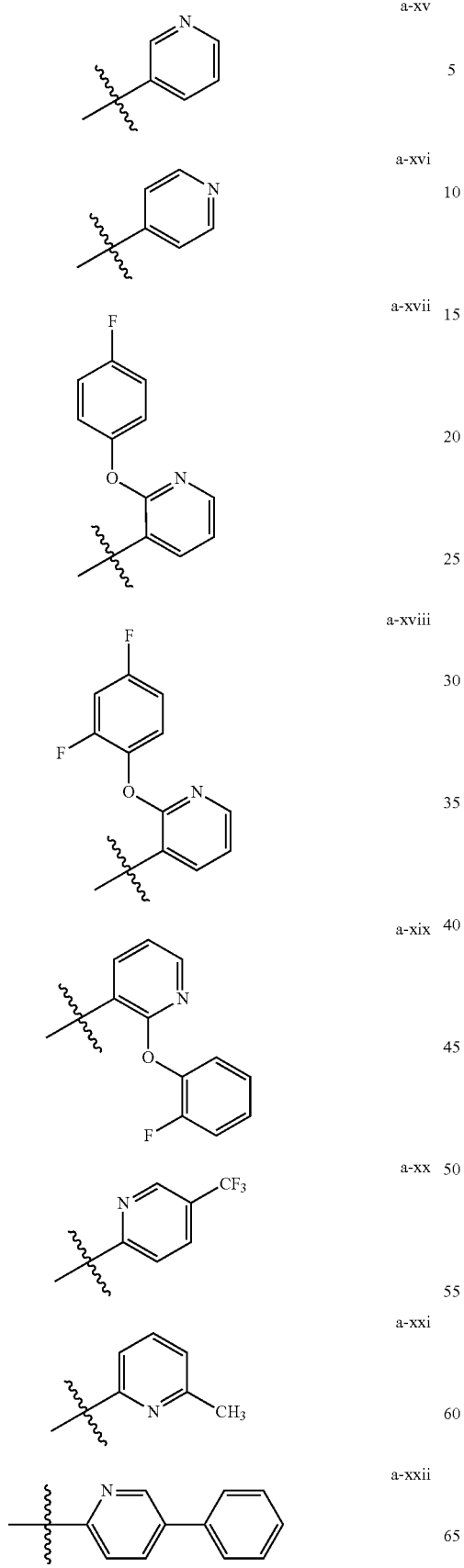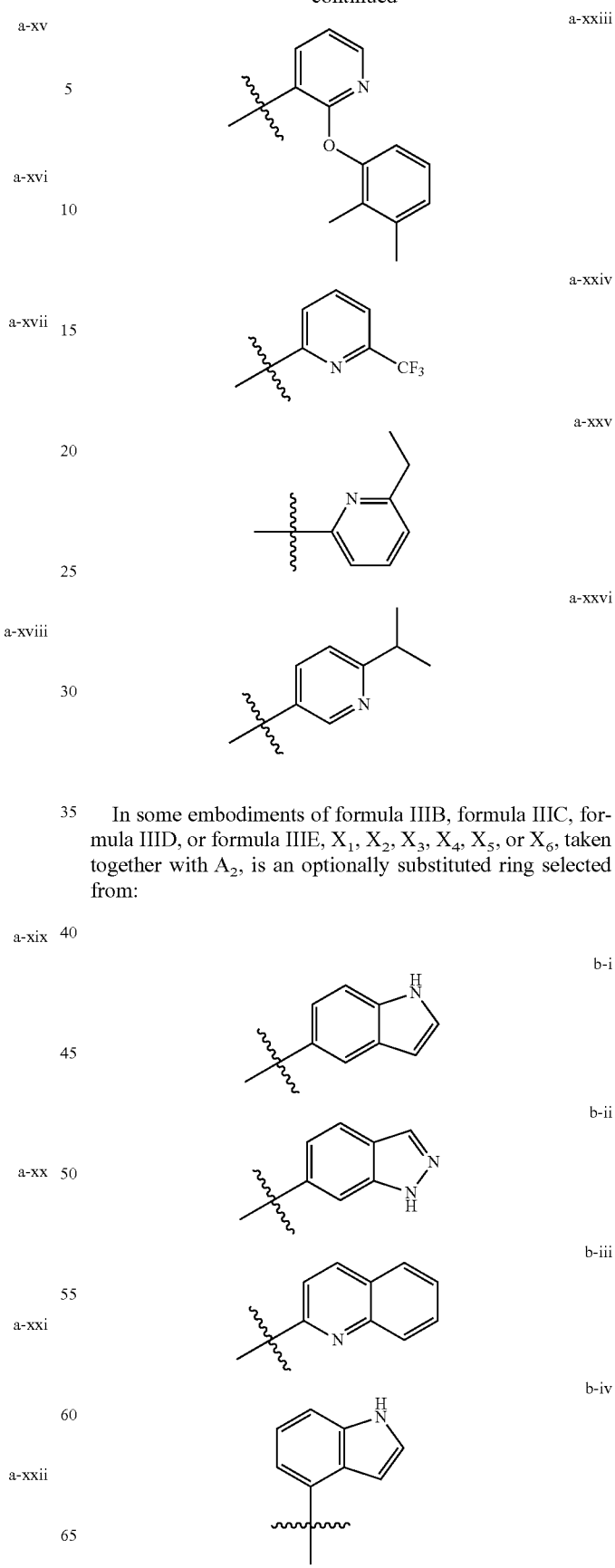
In some embodiments of formula IIIB, formula IIIC, formula IIID, or formula IIIE, $X_1$, $X_2$, $X_3$, $X_4$, $X_5$, or $X_6$, taken together with $A_2$, is an optionally substituted ring selected from:

-continued
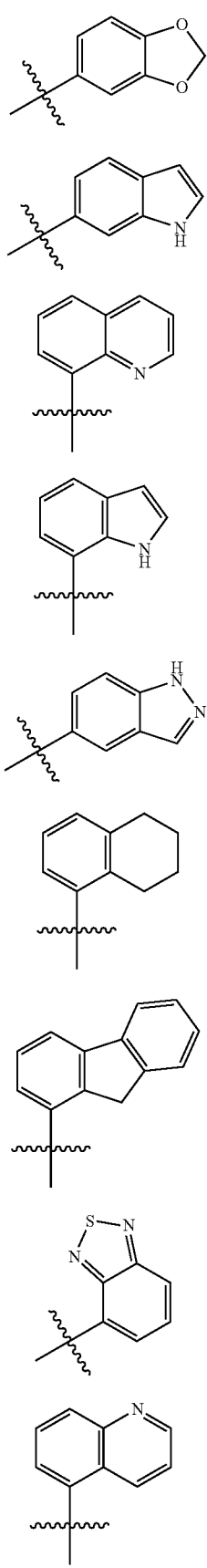
b-v
b-vi
b-vii
b-viii
b-ix
b-x
b-xi
b-xii
b-xiii
-continued
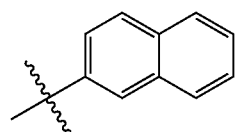
b-xiv
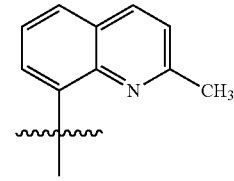
b-xv
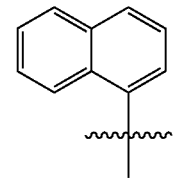
b-xvi
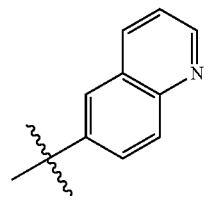
b-xvii
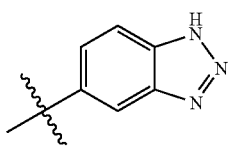
b-xviii
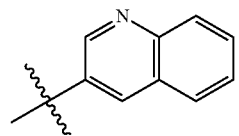
b-xix
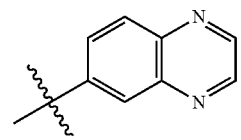
b-xx
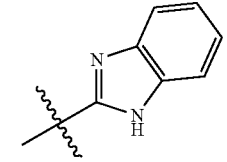
b-xxi
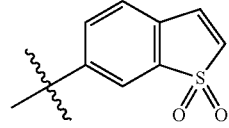
b-xxii

| | |
|---|---|
| b-xxiii 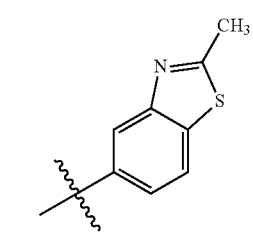 | b-xxxi 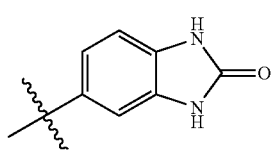 |
| b-xxiv 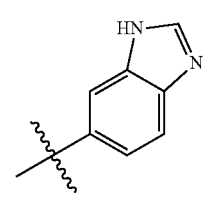 | b-xxxii 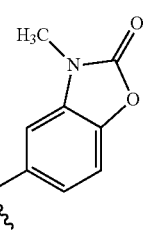 |
| b-xxv 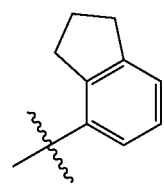 | b-xxxiii 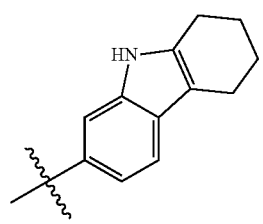 |
| b-xxvi 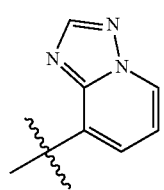 | b-xxxiv 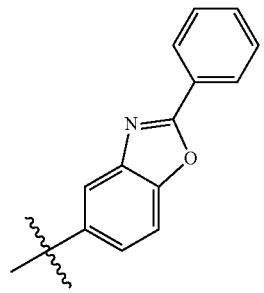 |
| b-xxvii 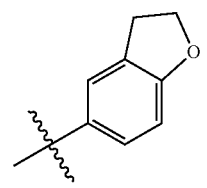 | |
| b-xxviii 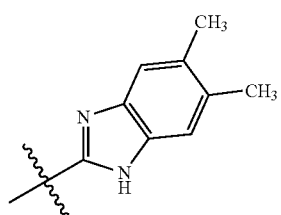 | b-xxxv 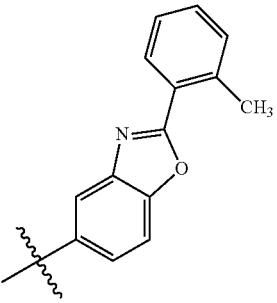 |
| b-xxix 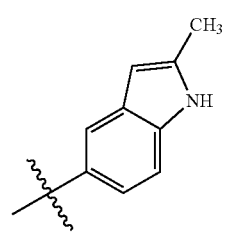 | |
| b-xxx 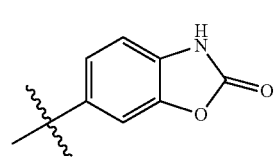 | b-xxxvi 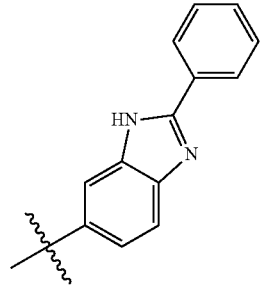 |

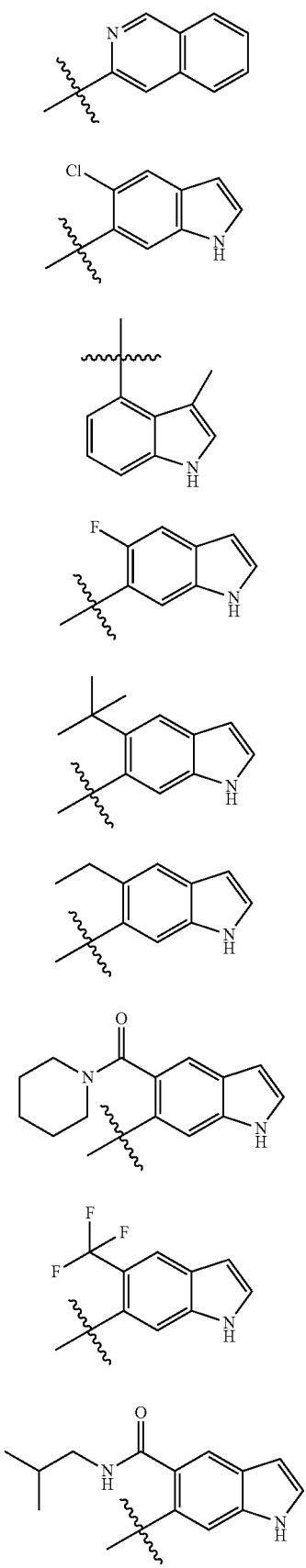
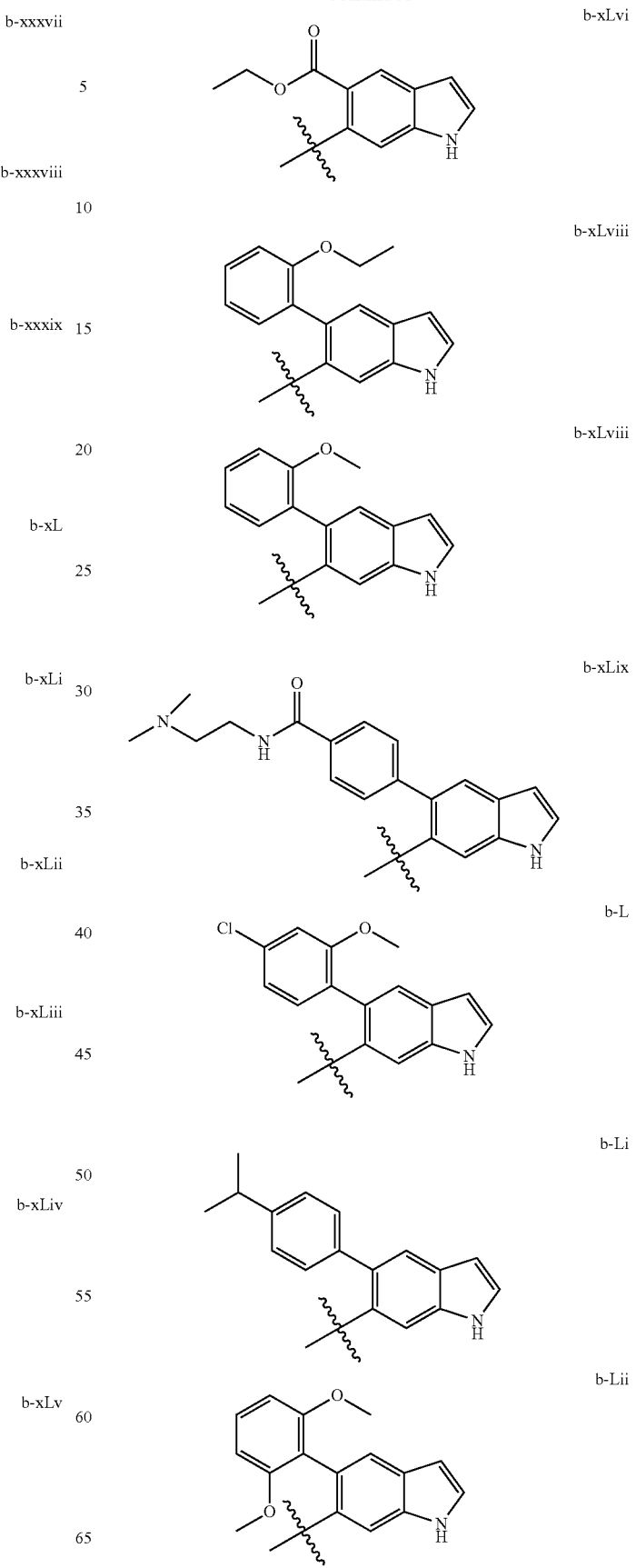

b-Liii
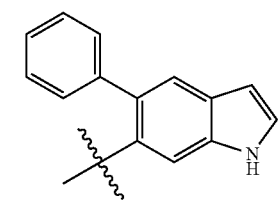
b-Liv
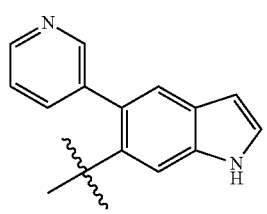
b-Lv
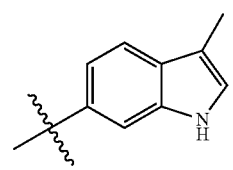
b-Lvi
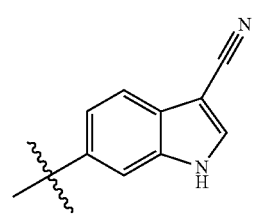
b-Lvii
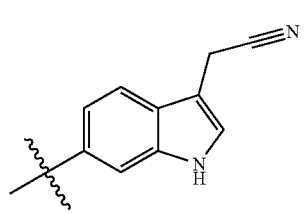
b-Lviii
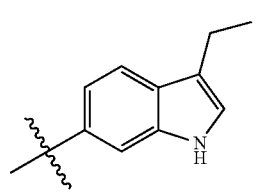
b-Lix
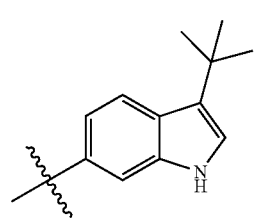
b-Lx
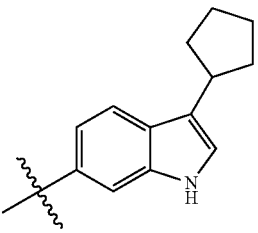
b-Lxi
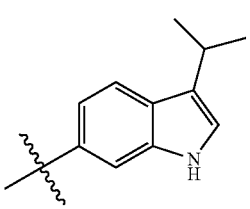
b-Lxii
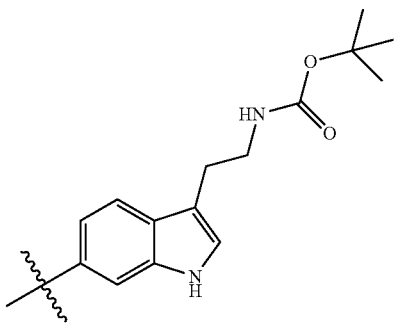
b-Lxiii
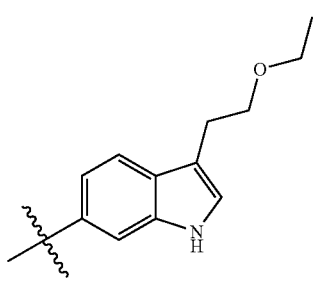
b-Lxiv
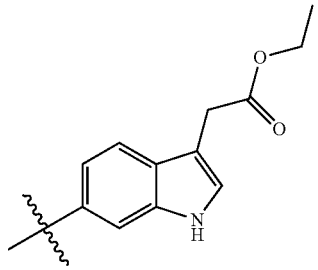
b-Lxv
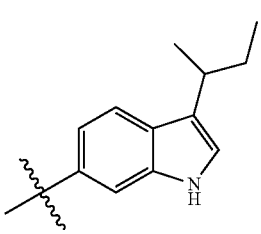

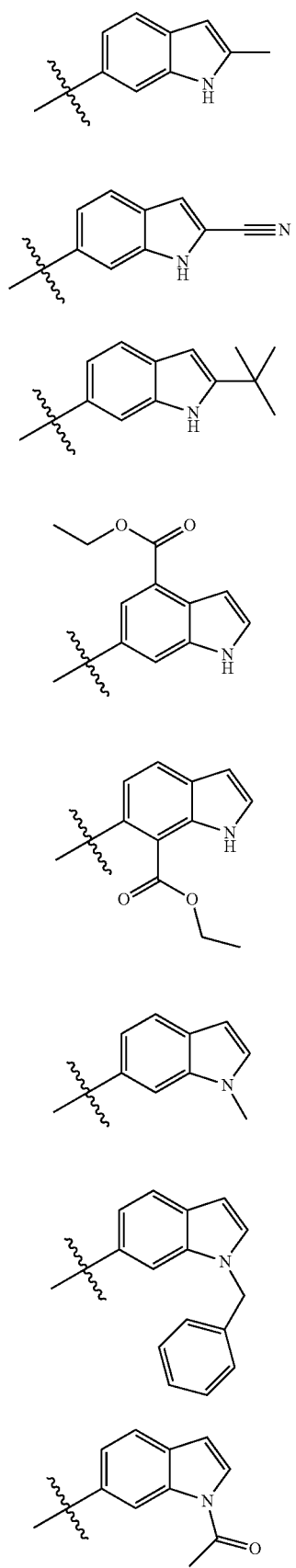
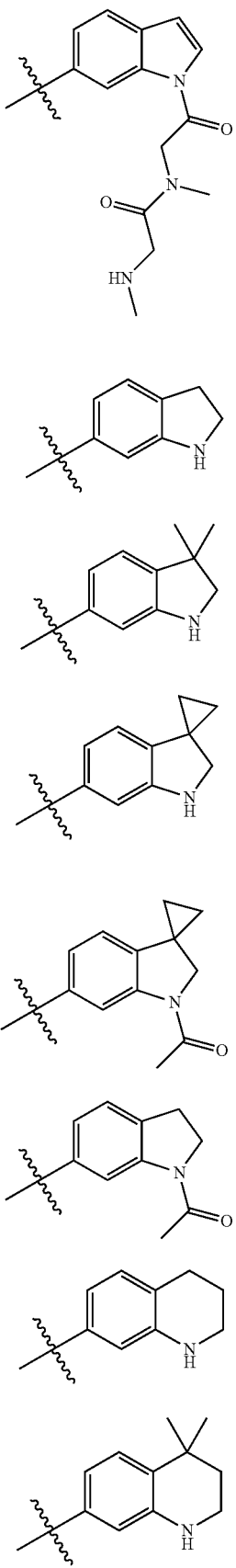

| 33 | 34 |
|---|---|
| -continued | -continued | b-Lxxxii b-Lxxxiii b-Lxxxiv b-Lxxxv b-Lxxxvi b-Lxxxviii b-Lxxxix b-xC b-xCi b-xCi b-xCii b-xCiii b-xCiv -continued

| | |
|---|---|
| 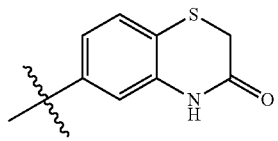 | b-xCv |
| 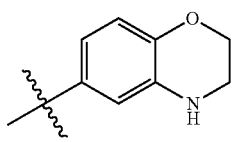 | b-xCvi |
| 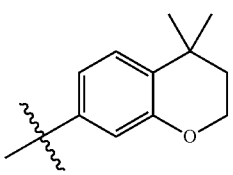 | b-xCvii |
| 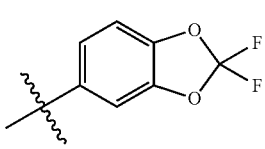 | b-xCviii |
| 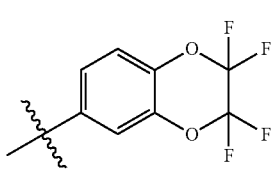 | b-xCix |
| 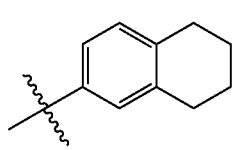 | b-C |
| 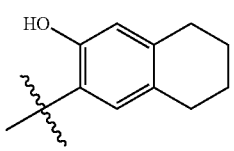 | b-Ci |
| 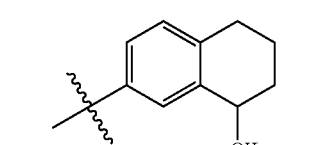 | b-Cii |
| 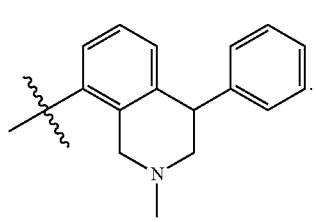 | b-Ciii |

In some embodiments, W and $R^w$, taken together is selected from halo, cyano, $CF_3$, $CHF_2$, $OCHF_2$, Me, Et, $CH(Me)_2$, CHMeEt, n-propyl, t-butyl, n-butyl, isoprenyl, OMe, OEt, OPh, O-fluorophenyl, O-difluorophenyl, O-2-methoxyphenyl, 2,4-dichlorophenyloxy, O-tolyl, O-benzyl, SMe, $SCF_3$, $SCHF_2$, SEt, $CH_2CN$, $NH_2$, NHMe, $N(Me)_2$, NHEt, $N(Et)_2$, $C(O)CH_3$, C(O)Ph, $C(O)NH_2$, SPh, $SO_2$-(amino-pyridyl), $SO_2NH_2$, $SO_2Ph$, $SO_2NHPh$, $SO_2$—N-morpholino, $SO_2$—N-pyrrolidyl, N-pyrrolyl, N-morpholino, 1-piperidyl, phenyl, benzyl, (cyclohexyl-methylamino)methyl, 4-Methyl-2,4-dihydro-pyrazol-3-one-2-yl, benzimidazol-2-yl, furan-2-yl, 4-Methyl-4H-[1,2,4]triazol-3-yl, 3-(4'-chlorophenyl)-[1,2,4]oxadiazol-5-yl, NHC(O)Me, NHC(O)Et, NHC(O)Ph, or $NHSO_2Me$.

In some embodiments, X and $R^X$, taken together, is Me, Et, halo, CN, or $CF_3$, OH, OMe, OEt, $SO_2N(Me)$(fluorophenyl), $SO_2$-(4-methyl)-piperidinyl, or $SO_2$—N-pyrrolidinyl.

According to another embodiment, the present invention provides compounds of formula IVA, formula IVB, or formula IVC:

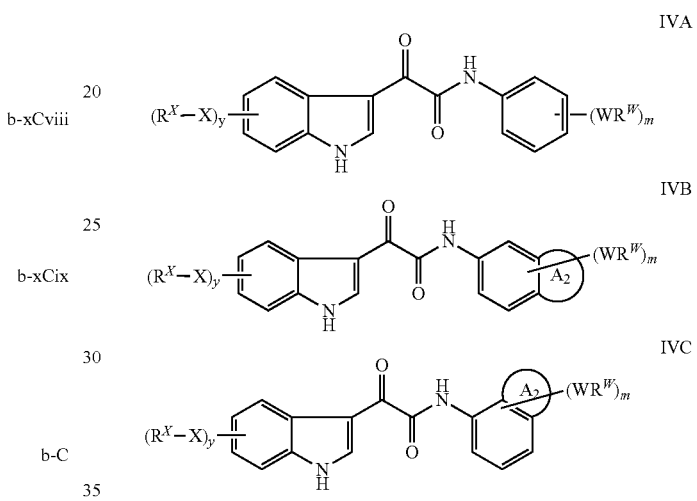

In one embodiment compounds of formula IVA, formula IVB, and formula IVC have y occurrences of substituent X—$R^X$, wherein y is 0-4. Or, y is 1. Or, y is 2.

In one embodiment, the present invention provides compounds of formula IVA, IVB, and IVC, wherein X is a bond and $R^X$ is hydrogen.

In one embodiment, the present invention provides compounds of formula IVB, and formula IVC, wherein ring $A_2$ is an optionally substituted, saturated, unsaturated, or aromatic seven membered ring with 0-3 heteroatoms selected from O, S, or N. Exemplary rings include azepanyl, 5,5-dimethyl azepanyl, etc.

In one embodiment, the present invention provides compounds of formula IVB and IVC, wherein ring $A_2$ is an optionally substituted, saturated, unsaturated, or aromatic six membered ring with 0-3 heteroatoms selected from O, S, or N. Exemplary rings include piperidinyl, 4,4-dimethylpiperidinyl, etc.

In one embodiment, the present invention provides compounds of formula IVB and IVC, wherein ring $A_2$ is an optionally substituted, saturated, unsaturated, or aromatic five membered ring with 0-3 heteroatoms selected from O, S, or N.

In one embodiment, the present invention provides compounds of formula IVB and IVC, wherein ring $A_2$ is an optionally substituted five membered ring with one nitrogen atom, e.g., pyrrolyl or pyrrolidinyl.

According to one embodiment of formula IVA, the following compound of formula VA-1 is provided:

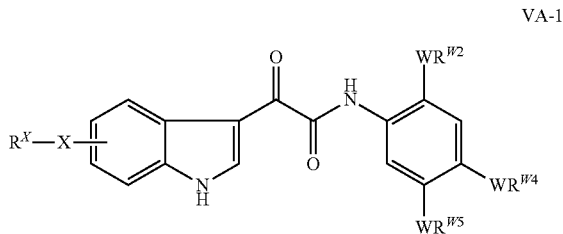

VA-1 wherein each of WR$^{W2}$ and WR$^{W4}$ is independently selected from hydrogen, CF$_3$, halo, C1-C6 straight or branched alkyl, 3-12 membered cycloaliphatic, phenyl, or C5-C10 heteroaryl or C3-C7 heterocyclic wherein said heteroaryl or heterocyclic has up to 3 heteroatoms selected from O, S or N, wherein said WR$^{W2}$ and WR$^{W4}$ is independently and optionally substituted with up to three substituents selected from —OR', —CF$_3$, —OCF$_3$, —SR', —S(O)R', —S(O)$_2$R', —SCF$_3$, halo, —COOR', —COR', —O(CH$_2$)$_2$N(R')(R'), —O(CH$_2$)N(R')(R'), —CON(R')(R'), —(CH$_2$)$_2$OR', —(CH$_2$)OR', optionally substituted phenyl, —N(R')(R'), —NC(O)OR', —NC(O)R', —(CH$_2$)$_2$N(R')(R'), or —(CH$_2$)N(R')(R'); and WR$^{W5}$ is selected from hydrogen, —OH, NH$_2$, CN, CHF$_2$, NHR', N(R')$_2$, —NHC(O)R', —NHC(O)OR', NHSO$_2$R', —OR', CH$_2$OH, CH$_2$N(R')$_2$, C(O)OR', SO$_2$NHR', SO$_2$N(R')$_2$, CH$_2$NHC(O)OR', or CH$_2$NHC(O)O-(t-butyl);

or WR$^{W4}$ and WR$^{W5}$ taken together form a 5-7 membered ring containing 0-3 heteroatoms selected from N, O, or S, wherein said ring is optionally substituted with up to three WR$^W$ substituents.

In one embodiment, the present invention provides compounds of formula VA-1, wherein X is a bond and R$^X$ is hydrogen.

In one embodiment, the present invention provides compounds of formula VA-1, wherein:
each of WR$^{W2}$ and WR$^{W4}$ is independently selected from hydrogen, CN, CF$_3$, halo, C1-C6 straight or branched alkyl, 3-12 membered cycloaliphatic, or phenyl, wherein said WR$^{W2}$ and WR$^{W4}$ is independently and optionally substituted with up to three substituents selected from —OR', —CF$_3$, —OCF$_3$, —SCF$_3$, halo, —COOR', —COR', —O(CH$_2$)$_2$N(R')(R'), —O(CH$_2$)N(R')(R'), —CON(R')(R'), —(CH$_2$)$_2$OR', —(CH$_2$)OR', optionally substituted phenyl, —N(R')(R'), —NC(O)OR', —NC(O)R', —(CH$_2$)$_2$N(R')(R'), or —(CH$_2$)N(R')(R'); and
WR$^{W5}$ is selected from hydrogen, —OH, NH$_2$, CN, NHR', N(R')$_2$, —NHC(O)R', —NHC(O)OR', NHSO$_2$R', —OR', CH$_2$OH, C(O)OR', SO$_2$NHR', CH$_2$NHC(O)O—(R'), or CH$_2$NHC(O)O-(t-butyl).

In one embodiment, the present invention provides compounds of formula VA-1, wherein:
WR$^{W2}$ is a phenyl ring optionally substituted with up to three substituents selected from —OR', —CF$_3$, —OCF$_3$, SR', S(O)R', SO$_2$R', —SCF$_3$, halo, CN, —COOR', —COR', —O(CH$_2$)$_2$N(R')(R'), —O(CH$_2$)N(R')(R'), —CON(R')(R'), —(CH$_2$)$_2$OR', —(CH$_2$)OR', CH$_2$CN, optionally substituted phenyl or phenoxyl, —N(R')(R'), —NR'C(O)OR', —NR'C(O)R', —(CH$_2$)$_2$N(R')(R'), or —(CH$_2$)N(R')(R');
WR$^{W4}$ is C1-C6 straight or branched alkyl; and
WR$^{W5}$ is OH.

In one embodiment, each of WR$^{W2}$ and WR$^{W4}$ is independently selected from CF$_3$ or halo. In one embodiment, each of WR$^{W2}$ and WR$^{W4}$ is independently selected from optionally substituted hydrogen, C1-C6 straight or branched alkyl. In certain embodiments, each of WR$^{W2}$ and WR$^{W4}$ is independently selected from optionally substituted n-propyl, isopropyl, n-butyl, sec-butyl, t-butyl, 1,1-dimethyl-2-hydroxyethyl, 1,1-dimethyl-2-(ethoxycarbonyl)-ethyl, 1,1-dimethyl-3-(t-butoxycarbonyl-amino) propyl, or n-pentyl.

In one embodiment, each of WR$^{W2}$ and WR$^{W4}$ is independently selected from optionally substituted 3-12 membered cycloaliphatic. Exemplary embodiments of such cycloaliphatic include cyclopentyl, cyclohexyl, cycloheptyl, norbornyl, adamantyl, [2.2.2.]bicyclo-octyl, [2.3.1.]bicyclo-octyl, or [3.3.1]bicyclo-nonyl.

In certain embodiments WR$^{W2}$ is hydrogen and WR$^{W4}$ is C1-C6 straight or branched alkyl. In certain embodiments, WR$^{W4}$ is selected from methyl, ethyl, propyl, n-butyl, sec-butyl, or t-butyl.

In certain embodiments WR$^{W4}$ is hydrogen and WR$^{W2}$ is C1-C6 straight or branched alkyl. In certain embodiments, WR$^{W2}$ is selected from methyl, ethyl, propyl, n-butyl, sec-butyl, t-butyl, or n-pentyl.

In certain embodiments each of WR$^{W2}$ and WR$^{W4}$ is C1-C6 straight or branched alkyl. In certain embodiments, each of WR$^{W2}$ and WR$^{W4}$ is selected from methyl, ethyl, propyl, n-butyl, sec-butyl, t-butyl, or pentyl.

In one embodiment, WR$^{W5}$ is selected from hydrogen, CHF$_2$, NH$_2$, CN, NHR', N(R')$_2$, —NHC(O)R', —NHC(O)OR', —OR', C(O)OR', or SO$_2$NHR'. Or WR$^{W5}$ is —OR', e.g., OH.

In certain embodiments, WR$^{W5}$ is selected from hydrogen, NH$_2$, CN, CHF$_2$, NH(C1-C6 alkyl), N(C1-C6 alkyl)$_2$, —NHC(O)(C1-C6 alkyl), —CH$_2$NHC(O)O(C1-C6 alkyl), —NHC(O)O(C1-C6 alkyl), —OH, —O(C1-C6 alkyl), C(O)O(C1-C6 alkyl), CH$_2$O(C1-C6 alkyl), or SO$_2$NH$_2$. In another embodiment, WR$^{W5}$ is selected from —OH, OMe, NH$_2$, —NHMe, —N(Me)$_2$, —CH$_2$NH$_2$, CH$_2$OH, NHC(O)OMe, NHC(O)OEt, CN, CHF$_2$, —CH$_2$NHC(O)O(t-butyl), —O-(ethoxyethyl), —O-(hydroxyethyl), —C(O)OMe, or —SO$_2$NH$_2$.

In one embodiment, compound of formula VA-1 has one, preferably more, or more preferably all, of the following features:
i) WR$^{W2}$ is hydrogen;
ii) WR$^{W4}$ is C1-C6 straight or branched alkyl or monocyclic or bicyclic aliphatic; and
iii) WR$^{W5}$ is selected from hydrogen, CN, NH(C1-C6 alkyl), N(C1-C6 alkyl)$_2$, —NHC(O)(C1-C6 alkyl), —NHC(O)O(C1-C6 alkyl), —OH, —O(C1-C6 alkyl), C(O)O(C1-C6 alkyl), or SO$_2$NH$_2$.

In one embodiment, compound of formula VA-1 has one, preferably more, or more preferably all, of the following features:
a. WR$^{W2}$ is halo, C1-C6 alkyl, CF$_3$, CN, or phenyl optionally substituted with up to 3 substituents selected from C1-C4 alkyl, —O(C1-C4 alkyl), or halo;
b. WR$^{W4}$ is CF$_3$, halo, C1-C6 alkyl, or C6-C10 cycloaliphatic; and
c. WR$^{W5}$ is OH, NH$_2$, NH(C1-C6 alkyl), or N(C1-C6 alkyl).

In one embodiment, X—R$^X$ is at the 6-position of the quinolinyl ring. In certain embodiments, X—R$^X$ taken together is C1-C6 alkyl, —O—(C1-C6 alkyl), or halo.

In one embodiment, X—R$^X$ is at the 5-position of the quinolinyl ring. In certain embodiments, X—R$^X$ taken together is —OH.

In another embodiment, the present invention provides compounds of formula VA-1, wherein WR$^{W4}$ and WR$^{W5}$ taken together form a 5-7 membered ring containing 0-3 heteroatoms selected from N, O, or S, wherein said ring is optionally substituted with up to three WR$^W$ substituents.

In certain embodiments, WR$^{W4}$ and WR$^{W5}$ taken together form an optionally substituted 5-7 membered saturated, unsaturated, or aromatic ring containing 0 heteroatoms. In other embodiments, WR$^{W4}$ and WR$^{W5}$ taken together form an optionally substituted 5-7 membered ring containing 1-3 heteroatoms selected from N, O, or S. In certain other embodiments, WR$^{W4}$ and WR$^{W5}$ taken together form an optionally substituted saturated, unsaturated, or aromatic 5-7 membered ring containing 1 nitrogen heteroatom. In certain other embodiments, WR$^{W4}$ and WR$^{W5}$ taken together form an optionally substituted 5-7 membered ring containing 1 oxygen heteroatom.

In another embodiment, the present invention provides compounds of formula V-A-2:

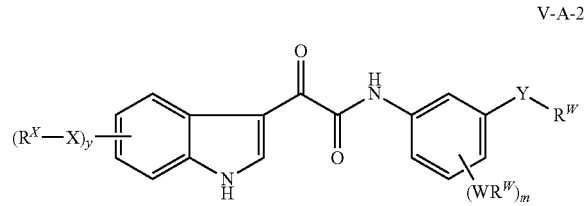

V-A-2 wherein:
Y is CH$_2$, C(O)O, C(O), or S(O)$_2$;
m is 0-4; and
X, R$^X$, W, and R$^W$ are as defined above.

In one embodiment, compounds of formula VA-2 have y occurrences of X—R$^X$, wherein y is 0-4. In one embodiment, y is 0. Or, y is 1. Or, y is 2.

In one embodiment, Y is C(O). In another embodiment, Y is C(O)O. Or, Y is S(O)$_2$. Or, Y is CH$_2$.

In one embodiment, m is 1 or 2. Or, m is 1. Or, m is 0.

In one embodiment, W is a bond.

In another embodiment, R$^W$ is C1-C6 aliphatic, halo, CF$_3$, or phenyl optionally substituted with C1-C6 alkyl, halo, cyano, or CF$_3$, wherein up to two methylene units of said C1-C6 aliphatic or C1-C6 alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is C1-C4 alkyl. Exemplary embodiments of WR$^W$ include methyl, ethyl, propyl, tert-butyl, or 2-ethoxyphenyl.

In another embodiment, R$^W$ in Y—R$^W$ is C1-C6 aliphatic optionally substituted with N(R'')$_2$, wherein R'' is hydrogen, C1-C6 alkyl, or two R'' taken together form a 5-7 membered heterocyclic ring with up to 2 additional heteroatoms selected from O, S, or NR'. Exemplary such heterocyclic rings include pyrrolidinyl, piperidyl, morpholinyl, or thiomorpholinyl.

In another embodiment, the present invention provides compounds of formula V-A-3:

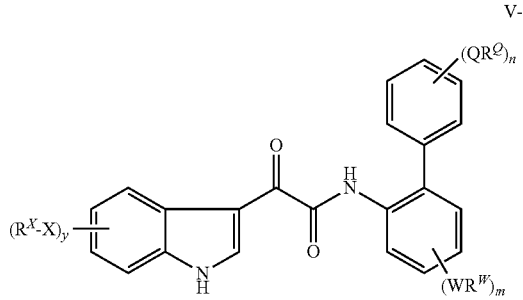

V-A-3 wherein:
Q is W;
R$^Q$ is R$^W$;
m is 0-4;
n is 0-4; and
X, R$^X$, W, and R$^W$ are as defined above.

In one embodiment, compounds of formula VA-3 have y occurrences of X—R$^X$, wherein y is 0-4. In one embodiment, y is 0. Or, y is 1. Or, y is 2.

In one embodiment, n is 0-2.

In another embodiment, m is 0-2. In one embodiment, m is 0. In one embodiment, m is 1. Or, m is 2.

In one embodiment, QR$^Q$ taken together is halo, CF$_3$, OCF$_3$, CHF$_2$, OCHF$_2$, CN, C1-C6 aliphatic, O—C1-C6 aliphatic, O-phenyl, NH(C1-C6 aliphatic), or N(C1-C6 aliphatic)$_2$, wherein said aliphatic and phenyl are optionally substituted with up to three substituents selected from C1-C6 alkyl, O—C1-C6 alkyl, halo, cyano, OH, or CF$_3$, wherein up to two methylene units of said C1-C6 aliphatic or C1-C6 alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, SOR', SO$_2$R', —SO$_2$NR'—, NR'SO$_2$—, or —NR'SO$_2$NR'—. In another embodiment, R' above is C1-C4 alkyl.

Exemplary QR$^Q$ include methyl, isopropyl, sec-butyl, hydroxymethyl, CF$_3$, NMe$_2$, CN, CH$_2$CN, fluoro, chloro, OEt, OMe, SMe, OCF$_3$, OPh, C(O)OMe, C(O)O-iPr, S(O)Me, NHC(O)Me, or S(O)$_2$Me.

In another embodiment, the present invention provides compounds of formula V-A-4:

V-A-4

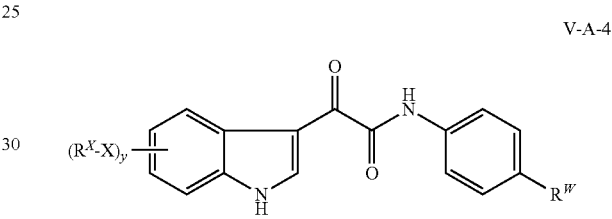

wherein X, R$^X$, and R$^W$ are as defined above.

In one embodiment, compounds of formula VA-4 have y occurrences of X—R$^X$, wherein y is 0-4. In one embodiment, y is 0. Or, y is 1. Or, y is 2.

In one embodiment, R$^W$ is C1-C12 aliphatic, C5-C10 cycloaliphatic, or C5-C7 heterocyclic ring, wherein said aliphatic, cycloaliphatic, or heterocyclic ring is optionally substituted with up to three substituents selected from C1-C6 alkyl, halo, cyano, oxo, OH, or CF$_3$, wherein up to two methylene units of said C1-C6 aliphatic or C1-C6 alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is C1-C4 alkyl.

Exemplary R$^W$ includes methyl, ethyl, n-propyl, isopropyl, n-butyl, sec-butyl, t-butyl, n-pentyl, vinyl, cyanomethyl, hydroxymethyl, hydroxyethyl, hydroxybutyl, cyclohexyl, adamantyl, or —C(CH$_3$)$_2$—NHC(O)O-T, wherein T is C1-C4 alkyl, methoxyethyl, or tetrahydrofuranylmethyl.

In another embodiment, the present invention provides compounds of formula V-A-5:

V-A-5

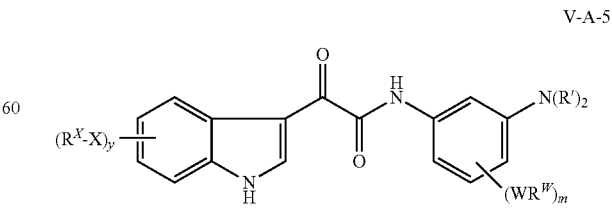

wherein:
m is 0-4; and
X, R$^X$, W, R$^W$, and R' are as defined above.

In one embodiment, compounds of formula VA-5 have y occurrences of X—R$^X$, wherein y is 0-4. In one embodiment, y is 0. Or, y is 1. Or, y is 2.

In one embodiment, m is 0-2. Or, m is 1. Or, m is 2.

In another embodiment, both R' are hydrogen. Or, one R' is hydrogen and the other R' is C1-C4 alkyl, e.g., methyl. Or, both R' are C1-C4 alkyl, e.g., methyl.

In another embodiment, m is 1 or 2, and R" is halo, CF$_3$, OCF$_3$, CHF$_2$, OCHF$_2$, CN, C1-C6 aliphatic, O—C1-C6 aliphatic, or phenyl, wherein said aliphatic and phenyl are optionally substituted with up to three substituents selected from C1-C6 alkyl, O—C1-C6 alkyl, halo, cyano, OH, or CF$_3$, wherein up to two methylene units of said C1-C6 aliphatic or C1-C6 alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is C1-C4 alkyl.

Exemplary embodiments of R$^W$ include chloro, CF$_3$, OCF$_3$, CHF$_2$, OCHF$_2$, methyl, ethyl, n-propyl, isopropyl, n-butyl, t-butyl, methoxy, ethoxy, propyloxy, or 2-ethoxyphenyl.

In another embodiment, the present invention provides compounds of formula V-A-6:

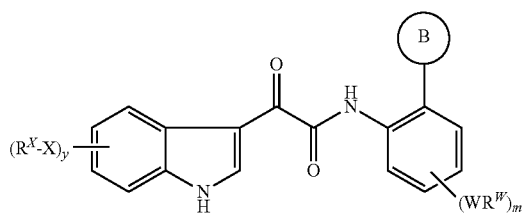

V-A-6 wherein:
ring B is a 5-7 membered monocyclic or bicyclic, heterocyclic or heteroaryl ring optionally substituted with up to n occurrences of -Q-R$^Q$, wherein n is 0-4, and Q and R$^Q$ are as defined above; and Q, R$^Q$, X, R$^X$, W, and R$^W$ are as defined above.

In one embodiment, compounds of formula VA-6 have y occurrences of X—R$^X$, wherein y is 0-4. In one embodiment, y is 0. Or, y is 1. Or, y is 2.

In one embodiment, m is 0-2. Or, m is 0. Or m is 1.

In one embodiment, n is 0-2. Or, n is 0. Or, n is 1.

In another embodiment, ring B is a 5-7 membered monocyclic, heterocyclic ring having up to 2 heteroatoms selected from O, S, or N, optionally substituted with up to n occurrences of -Q-R$^Q$. Exemplary heterocyclic rings include N-morpholinyl, N-piperidinyl, 4-benzoyl-piperazin-1-yl, pyrrolidin-1-yl, or 4-methyl-piperidin-1-yl.

In another embodiment, ring B is a 5-6 membered monocyclic, heteroaryl ring having up to 2 heteroatoms selected from O, S, or N, optionally substituted with up to n occurrences of -Q-R$^Q$. Exemplary such rings include benzimidazol-2-yl, 5-methyl-furan-2-yl, 2,5-dimethyl-pyrrol-1-yl, pyridine-4-yl, indol-5-yl, indol-2-yl, 2,4-dimethoxy-pyrimidin-5-yl, furan-2-yl, furan-3-yl, 2-acyl-thien-2-yl, benzothiophen-2-yl, 4-methyl-thien-2-yl, 5-cyano-thien-2-yl, 3-chloro-5-trifluoromethyl-pyridin-2-yl.

In another embodiment, the present invention provides compounds of formula V-B-1:

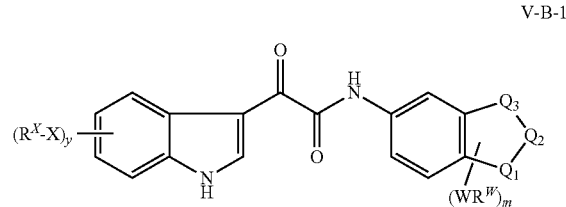

V-B-1 wherein:
one of Q$_1$ and Q$_3$ is N(WR$^W$) and the other of Q$_1$ and Q$_3$ is selected from O, S, or N(WR$^W$);
Q$_2$ is C(O), CH$_2$—C(O), C(O)—CH$_2$, CH$_2$, CH$_2$—CH$_2$, CF$_2$, or CF$_2$—CF$_2$;
m is 0-3; and
X, W, R$^X$, and R$^W$ are as defined above.

In one embodiment, compounds of formula V-B-1 have y occurrences of X—R$^X$, wherein y is 0-4. In one embodiment, y is 0. Or, y is 1. Or, y is 2.

In one embodiment, Q$_3$ is N(WR$^W$); exemplary WR$^W$ include hydrogen, C1-C6 aliphatic, C(O)C1-C6 aliphatic, or C(O)OC1-C6 aliphatic.

In another embodiment, Q$_3$ is N(WR$^W$), Q$_2$ is C(O), CH$_2$, CH$_2$—CH$_2$, and Q$_1$ is O.

In another embodiment, the present invention provides compounds of formula V-B-2:

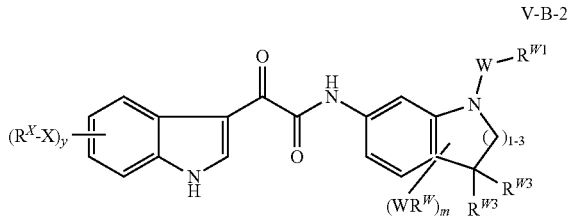

V-B-2 wherein:
R$^{W1}$ is hydrogen or C1-C6 aliphatic;
each of R$^{W3}$ is hydrogen or C1-C6 aliphatic; or
both R$^{W3}$ taken together form a C3-C6 cycloalkyl or heterocyclic ring having up to two heteroatoms selected from O, S, or NR', wherein said ring is optionally substituted with up to two WR$^W$ substituents;
m is 0-4; and
X, R$^X$, W, and R$^W$ are as defined above.

In one embodiment, compounds of formula V-B-2 have y occurrences of X—R$^X$, wherein y is 0-4. In one embodiment, y is 0. Or, y is 1. Or, y is 2.

In one embodiment, WR$^{W1}$ is hydrogen, C1-C6 aliphatic, C(O)C1-C6 aliphatic, or C(O)OC1-C6 aliphatic.

In another embodiment, each R$^{W3}$ is hydrogen, C1-C4 alkyl. Or, both R$^{W3}$ taken together form a C3-C6 cycloaliphatic ring or 5-7 membered heterocyclic ring having up to two heteroatoms selected from O, S, or N, wherein said cycloaliphatic or heterocyclic ring is optionally substituted with up to three substituents selected from WR$^{W1}$. Exemplary such rings include cyclopropyl, cyclopentyl, optionally substituted piperidyl, etc.

In another embodiment, the present invention provides compounds of formula V-B-3:

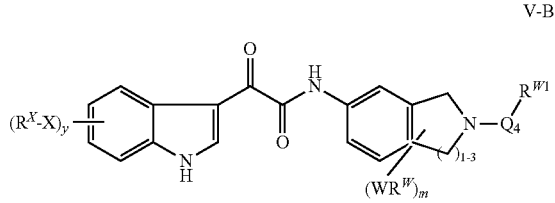

V-B-3 wherein:
Q$_4$ is a bond, C(O), C(O)O, or S(O)$_2$;
R$^{W1}$ is hydrogen or C1-C6 aliphatic;
m is 0-4; and
X, W, R$^W$, and R$^X$ are as defined above.

In one embodiment, compounds of formula V-B-3 have y occurrences of X—R$^X$, wherein y is 0-4. In one embodiment, y is 0.

In one embodiment, Q$_4$ is C(O). Or Q$_4$ is C(O)O. In another embodiment, R$^{W1}$ is C1-C6 alkyl. Exemplary R$^{W1}$ include methyl, ethyl, or t-butyl.

In another embodiment, the present invention provides compounds of formula V-B-4:

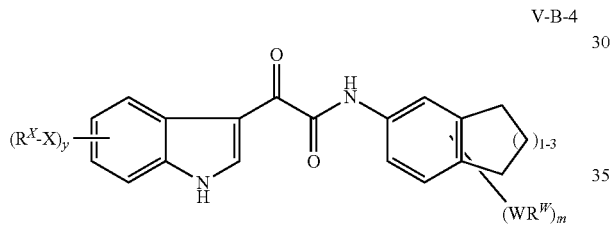

V-B-4 wherein:
m is 0-4; and
X, R$^X$, W, and R$^W$ are as defined above.

In one embodiment, compounds of formula V-B-4 have y occurrences of X—R$^X$, wherein y is 0-4. In one embodiment, y is 0. Or, y is 1. Or, y is 2.

In one embodiment, m is 0-2. Or, m is 0. Or, m is 1.

In another embodiment, said cycloaliphatic ring is a 5-membered ring. Or, said ring is a six-membered ring.

In another embodiment, the present invention provides compounds of formula V-B-5:

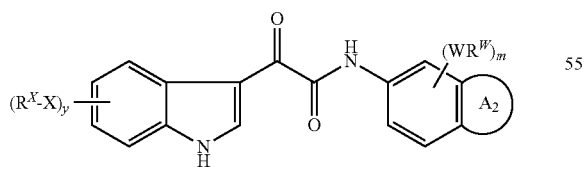

V-B-5 wherein:
ring A$_2$ is a phenyl or a 5-6 membered heteroaryl ring, wherein ring A$_2$ and the phenyl ring fused thereto together have up 4 substituents independently selected from WR$^W$;
m is 0-4; and
X, W, R$^W$ and R$^X$ are as defined above.

In one embodiment, compounds of formula V-B-5 have y occurrences of X—R$^X$, wherein y is 0-4. In one embodiment, y is 0. Or, y is I. Or, y is 2.

In one embodiment, ring A$_2$ is an optionally substituted 5-membered ring selected from pyrrolyl, furanyl, thienyl, pyrazolyl, imidazolyl, thiazolyl, oxazolyl, thiadiazolyl, oxadiazolyl, or triazolyl.

In one embodiment, ring A$_2$ is an optionally substituted 5-membered ring selected from pyrrolyl, pyrazolyl, thiadiazolyl, imidazolyl, oxazolyl, or triazolyl. Exemplary such rings include:

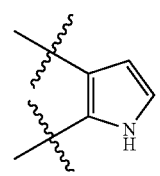

aa

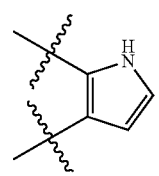

bb

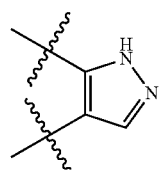

cc

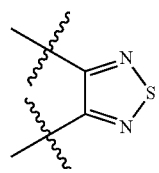

dd

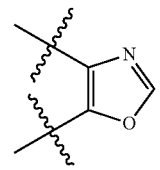

ee

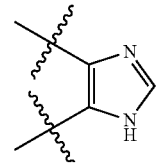

ff

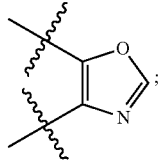

gg wherein said ring is optionally substituted as set forth above.

In another embodiment, ring $A_2$ is an optionally substituted 6-membered ring. Exemplary such rings include pyridyl, pyrazinyl, or triazinyl. In another embodiment, said ring is an optionally pyridyl.

In one embodiment, ring $A_2$ is phenyl.

In another embodiment, ring $A_2$ is pyrrolyl, pyrazolyl, pyridyl, or thiadiazolyl.

Exemplary W in formula V-B-5 includes a bond, C(O), C(O)O or C1-C6 alkylene.

Exemplary $R^W$ in formula V-B-5 include cyano, halo, C1-C6 aliphatic, C3-C6 cycloaliphatic, aryl, 5-7 membered heterocyclic ring having up to two heteroatoms selected from O, S, or N, wherein said aliphatic, phenyl, and heterocyclic are independently and optionally substituted with up to three substituents selected from C1-C6 alkyl, O—C1-C6 alkyl, halo, cyano, OH, or $CF_3$, wherein up to two methylene units of said C1-C6 aliphatic or C1-C6 alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is C1-C4 alkyl.

In one embodiment, the present invention provides compounds of formula V-B-5-a:

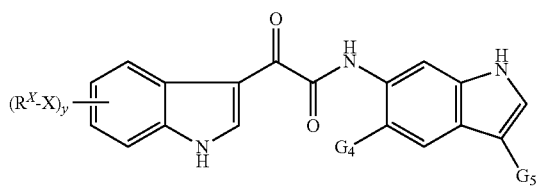

V-B-5-a wherein:
  $G_4$ is hydrogen, halo, CN, $CF_3$, $CHF_2$, $CH_2F$, optionally substituted C1-C6 aliphatic, aryl-C1-C6 alkyl, or a phenyl, wherein $G_4$ is optionally substituted with up to 4 $WR^W$ substituents; wherein up to two methylene units of said C1-C6 aliphatic or C1-C6 alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—;
  $G_5$ is hydrogen or an optionally substituted C1-C6 aliphatic;
wherein said indole ring system is further optionally substituted with up to 3 substituents independently selected from $WR^W$.

In one embodiment, compounds of formula V-B-5-a have y occurrences of X—$R^X$, wherein y is 0-4. In one embodiment, y is 0. Or, y is 1. Or, y is 2.

In one embodiment, $G_4$ is hydrogen. Or, $G_5$ is hydrogen.

In another embodiment, $G_4$ is hydrogen, and $G_5$ is C1-C6 aliphatic, wherein said aliphatic is optionally substituted with C1-C6 alkyl, halo, cyano, or $CF_3$, and wherein up to two methylene units of said C1-C6 aliphatic or C1-C6 alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is C1-C4 alkyl.

In another embodiment, $G_4$ is hydrogen, and $G_5$ is cyano, methyl, ethyl, propyl, isopropyl, butyl, sec-butyl, t-butyl, cyanomethyl, methoxyethyl, $CH_2C(O)OMe$, $(CH_2)_2$—NHC(O)O-tert-butyl, or cyclopentyl.

In another embodiment, $G_5$ is hydrogen, and $G_4$ is halo, C1-C6 aliphatic or phenyl, wherein said aliphatic or phenyl is optionally substituted with C1-C6 alkyl, halo, cyano, or $CF_3$, wherein up to two methylene units of said C1-C6 aliphatic or C1-C6 alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is C1-C4 alkyl.

In another embodiment, $G_5$ is hydrogen, and $G_4$ is halo, $CF_3$, ethoxycarbonyl, t-butyl, 2-methoxyphenyl, 2-ethoxyphenyl, (4-C(O)NH(CH$_2$)$_2$—NMe$_2$)-phenyl, 2-methoxy-4-chloro-phenyl, pyridine-3-yl, 4-isopropylphenyl, 2,6-dimethoxyphenyl, sec-butylaminocarbonyl, ethyl, t-butyl, or piperidin-1-ylcarbonyl.

In another embodiment, $G_4$ and $G_5$ are both hydrogen, and the nitrogen ring atom of said indole ring is substituted with C1-C6 aliphatic, C(O)(C1-C6 aliphatic), or benzyl, wherein said aliphatic or benzyl is optionally substituted with C1-C6 alkyl, halo, cyano, or $CF_3$, wherein up to two methylene units of said C1-C6 aliphatic or C1-C6 alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is C1-C4 alkyl.

In another embodiment, $G_4$ and $G_5$ are both hydrogen, and the nitrogen ring atom of said indole ring is substituted with acyl, benzyl, C(O)CH$_2$N(Me)C(O)CH$_2$NHMe, or ethoxycarbonyl.

Representative compounds of the present invention are set forth below in Table 1 below.

TABLE 1

| Cmpd # | Compound |
| --- | --- |
| 1 | ![structure] |
| 2 | ![structure] |

TABLE 1-continued

| Cmpd # | Compound |
|---|---|
| 3 | 2-(1H-indol-3-yl)-N-(2-ethylphenyl)-2-oxoacetamide |
| 4 | 2-(1H-indol-3-yl)-N-(1H-indol-6-yl)-2-oxoacetamide |
| 5 | 2-(1H-indol-3-yl)-2-oxo-N-(2-propylphenyl)acetamide |
| 6 | 2-(1H-indol-3-yl)-N-(2-isopropylphenyl)-2-oxoacetamide |
| 7 | 2-(1H-indol-3-yl)-N-(4-tert-butylphenyl)-2-oxoacetamide |
| 8 | N-(biphenyl-2-yl)-2-(1H-indol-3-yl)-2-oxoacetamide |
| 9 | 2-(1H-indol-3-yl)-2-oxo-N-phenylacetamide |
| 10 | 2-(1H-indol-3-yl)-2-oxo-N-(6-(trifluoromethyl)pyridin-2-yl)acetamide |
| 11 | 2-(1H-indol-3-yl)-N-(2-(2-methylphenoxy)phenyl)-2-oxoacetamide |
| 12 | 2-(1H-indol-3-yl)-2-oxo-N-(2-(prop-1-en-2-yl)phenyl)acetamide |

TABLE 1-continued

| Cmpd # | Compound |
|---|---|
| 13 | |
| 14 | |
| 15 | |
| 16 | |
| 17 | |
| 18 | |
| 19 | |
| 20 | |

TABLE 1-continued

| Cmpd # | Compound |
|---|---|
| 21 | |
| 22 | |
| 23 | |
| 24 | |
| 25 | |
| 26 | |

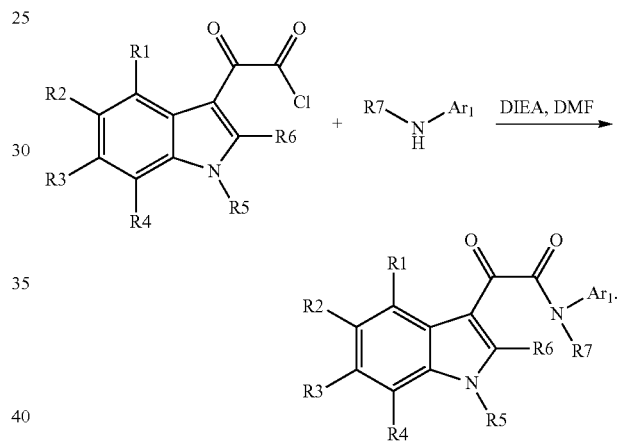

4. General Synthetic Schemes

Compounds of formula I can be prepared by well-known methods in the art. Illustrated below are exemplary methods for the preparation of compounds of formula I. Scheme I below illustrates an exemplary synthetic method for compounds of formula I, wherein $R^5$ is hydrogen.

Scheme I:

Exemplary compounds of the present invention prepared according to Scheme 1 are recited below in the Examples.

5. Uses, Formulation and Administration

Pharmaceutically Acceptable Compositions

As discussed above, the present invention provides compounds that are useful as modulators of ABC transporters and thus are useful in the treatment of disease, disorders or conditions such as cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease.

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need thereof is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, the present invention provides a method of treating a condition, disease, or disorder implicated by ABC transporter activity, e.g., CFTR. In certain embodiments, the present invention provides a method of treating a condition, disease, or disorder implicated by a deficiency of the ABC transporter activity, the method comprising administering a composition comprising a compound of formula Ito a subject, preferably a mammal, in need thereof.

In certain embodiments, the present invention provides a method of treating cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease, comprising the step of administering to said mammal an effective amount of a composition comprising a compound of the present invention.

According to an alternative preferred embodiment, the present invention provides a method of treating cystic fibrosis comprising the step of administering to said mammal a composition comprising the step of administering to said mammal an effective amount of a composition comprising a compound of the present invention.

According to the invention an "effective amount" of the compound or pharmaceutically acceptable composition is that amount effective for treating or lessening the severity of one or more of cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease.

The compounds and compositions, according to the method of the present invention, may be administered using any amount and any route of administration effective for treating or lessening the severity of one or more of cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease.

In one embodiment, the compounds and compositions of the present invention are useful for treating or lessening the severity of cystic fibrosis in a patient.

In certain embodiments, the compounds and compositions of the present invention are useful for treating or lessening the severity of cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl⁻ concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, ΔF508.

In another embodiment, the compounds and compositions of the present invention are useful for treating or lessening the severity of cystic fibrosis in patients who have residual CFTR activity induced or augmented using pharmacological methods or gene therapy. Such methods increase the amount of CFTR present at the cell surface, thereby inducing a hitherto absent CFTR activity in a patient or augmenting the existing level of residual CFTR activity in a patient.

In one embodiment, the compounds and compositions of the present invention are useful for treating or lessening the severity of cystic fibrosis in patients within certain genotypes exhibiting residual CFTR activity, e.g., class III mutations (impaired regulation or gating), class IV mutations (altered conductance), or class V mutations (reduced synthesis) (Lee R. Choo-Kang, Pamela L., Zeitlin, *Type I, II, III, IV, and V cystic fibrosis Tansmembrane Conductance Regulator Defects and Opportunities of Therapy*; Current Opinion in Pulmonary Medicine 6:521-529, 2000). Other patient genotypes that exhibit residual CFTR activity include patients homozygous for one of these classes or heterozygous with any other class of mutations, including class I mutations, class II mutations, or a mutation that lacks classification.

In one embodiment, the compounds and compositions of the present invention are useful for treating or lessening the severity of cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic sufficiency or patients diagnosed with idiopathic pancreatitis and congenital bilateral absence of the vas deferens, or mild lung disease.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as modulators of ABC transporters. Thus, without wishing to be bound by any particular theory, the compounds and compositions are particularly useful for treating or lessening the severity of a disease, condition, or disorder where hyperactivity or inactivity of ABC transporters is implicated in the disease, condition, or disorder. When hyperactivity or inactivity of an ABC transporter is implicated in a particular disease, condition, or disorder, the disease, condition, or disorder may also be referred to as a "ABC transporter-mediated disease, condition or disorder". Accordingly, in another aspect, the present invention provides a method for treating or lessening the severity of a disease, condition, or disorder where hyperactivity or inactivity of an ABC transporter is implicated in the disease state.

The activity of a compound utilized in this invention as a modulator of an ABC transporter may be assayed according to methods described generally in the art and in the Examples herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

In one embodiment, the additional agent is selected from a mucolytic agent, bronchodialator, an anti-biotic, an anti-infective agent, an anti-inflammatory agent, a CFTR modulator other than a compound of the present invention, or a nutritional agent.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to modulating ABC transporter activity in a biological sample or a patient (e.g., in vitro or in vivo), which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of ABC transporter activity, e.g., CFTR, in a biological sample is useful for a variety of purposes that are known to one of skill in the art. Examples of such purposes include, but are not limited to, the study of ABC transporters in biological and pathological phenomena; and the comparative evaluation of new modulators of ABC transporters.

In yet another embodiment, a method of modulating activity of an anion channel in vitro or in vivo, is provided comprising the step of contacting said channel with a compound of formula I. In preferred embodiments, the anion channel is a chloride channel or a bicarbonate channel. In other preferred embodiments, the anion channel is a chloride channel.

According to an alternative embodiment, the present invention provides a method of increasing the number of functional ABC transporters in a membrane of a cell, comprising the step of contacting said cell with a compound of formula I. The term "functional ABC transporter" as used herein means an ABC transporter that is capable of transport activity. In preferred embodiments, said functional ABC transporter is CFTR.

According to another preferred embodiment, the activity of the ABC transporter is measured by measuring the transmembrane voltage potential. Means for measuring the voltage potential across a membrane in the biological sample may employ any of the known methods in the art, such as optical membrane potential assay or other electrophysiological methods.

The optical membrane potential assay utilizes voltage-sensitive FRET sensors described by Gonzalez and Tsien (See Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential ($V_m$) cause the negatively charged DiSBAC$_2$(3) to redistribute across the plasma membrane and the amount of energy transfer from CC2-DMPE changes accordingly. The changes in fluorescence emission can be monitored using VIPR™ II, which is an integrated liquid handler and fluorescent detector designed to conduct cell-based screens in 96- or 384-well microtiter plates.

In another aspect the present invention provides a kit for use in measuring the activity of a ABC transporter or a fragment thereof in a biological sample in vitro or in vivo comprising (i) a composition comprising a compound of formula I or any of the above embodiments; and (ii) instructions for a) contacting the composition with the biological sample and b) measuring activity of said ABC transporter or a fragment thereof. In one embodiment, the kit further comprises instructions for a) contacting an additional composition with the biological sample; b) measuring the activity of said ABC transporter or a fragment thereof in the presence of said additional compound, and c) comparing the activity of the ABC transporter in the presence of the additional compound with the density of the ABC transporter in the presence of a composition of formula I. In preferred embodiments, the kit is used to measure the density of CFTR.

In order that the invention described herein may be more fully understood, the following examples are set forth. It should be understood that these examples are for illustrative purposes only and are not to be construed as limiting this invention in any manner.

EXAMPLES

Example 1

Preparation of N-(2-Ethyl-phenyl)-2-(1H-indol-3-yl)-2-oxo-acetamide

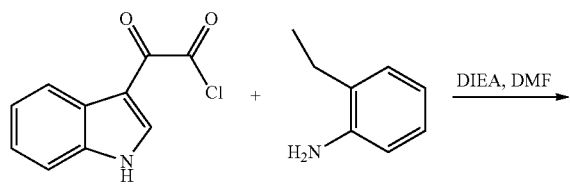

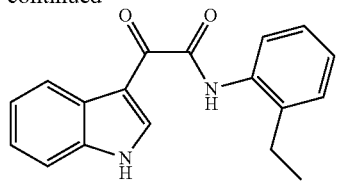

To a stirring solution of 2-ethyl-aniline (74 µL, 0.6 mmol) and DIEA (110 µL, 0.6 mmol) in DMF (1 mL) was added a solution of (1H-indol-3-yl)-oxo-acetyl chloride (62 mg, 0.3 mmol) in DMF (1 mL). The reaction was stirred at room temperature for 2 hours, then filtered and purified by HPLC (10-99% CH$_3$CN/H$_2$O) to yield the product N-(2-ethyl-phenyl)-2-(1H-indol-3-yl)-2-oxo-acetamide (34 mg, 39%). HPLC ret. time 3.50 min, 10-99% CH$_3$CN, 5 min run; $^1$H NMR (400 MHz, DMSO-d6) δ 12.33 (s, 1H), 10.14 (s, 1H), 8.79 (d, J=3.2 Hz, 1H), 8.30 (m, 1H), 7.57 (m, 2H), 7.33-7.21 (m, 5H), 2.67 (q, J=7.6 Hz, 2H), 1.17 (t, J=7.6 Hz, 3H); ESI-MS m/z 293.1 (MH$^+$).

Set forth below is the characterizing data for compounds of the present invention prepared according to the above Example.

TABLE 2

| Cmpd # | LC-MS m/z | LC-RT min |
| --- | --- | --- |
| 3 | 293.10 | 3.50 |
| 4 | 304.10 | 3.17 |
| 5 | 307.30 | 3.67 |
| 6 | 307.50 | 3.60 |
| 7 | 321.50 | 3.89 |
| 8 | 341.30 | 3.75 |
| 9 |  | 3.21 |
| 10 | 334.30 | 3.53 |
| 11 | 371.10 | 4.02 |
| 12 | 305.50 | 3.69 |
| 13 | 321.30 | 3.85 |
| 14 | 425.30 | 4.16 |
| 15 | 362.30 | 2.28 |
| 16 | 279.30 | 3.45 |
| 17 | 355.30 | 3.97 |
| 18 | 348.50 | 2.31 |
| 19 | 348.30 | 3.20 |
| 20 | 410.30 | 2.60 |
| 21 | 358.30 | 3.84 |
| 22 |  | 3.46 |
| 23 |  | 3.38 |
| 24 | 393.30 | 4.23 |
| 25 | 360.20 | 3.78 |
| 26 | 321.3 | 3.85 |

B) Assays for Detecting and Measuring ΔF508-CFTR Correction Properties of Compounds I) Membrane Potential Optical Methods for Assaying ΔF508-CFTR Modulation Properties of Compounds The optical membrane potential assay utilized voltage-sensitive FRET sensors described by Gonzalez and Tsien (See., Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential ($V_m$) cause the negatively charged DiSBAC$_2$(3) to redistribute across the plasma membrane and the amount of energy transfer from CC2-DMPE changes accordingly. The changes in fluorescence emission were monitored using VIPR which is an integrated liquid handler and fluorescent detector designed to conduct cell-based screens in 96- or 384-well microtiter plates.

Identification of Correction Compounds

To identify small molecules that correct the trafficking defect associated with ΔF508-CFTR; a single-addition HTS assay format was developed. The cells were incubated in serum-free medium for 16 hrs at 37° C. in the presence or absence (negative control) of test compound. As a positive control, cells plated in 384-well plates were incubated for 16 hrs at 27° C. to "temperature-correct" ΔF508-CFTR. The cells were subsequently rinsed 3× with Krebs Ringers solution and loaded with the voltage-sensitive dyes. To activate ΔF508-CFTR, 10 μM forskolin and the CFTR potentiator, genistein (20 μM), were added along with Cl⁻-free medium to each well. The addition of Cl⁻-free medium promoted Cl⁻ efflux in response to LF508-CFTR activation and the resulting membrane depolarization was optically monitored using the FRET-based voltage-sensor dyes.

Identification of Potentiator Compounds

To identify potentiators of ΔF508-CFTR, a double-addition HTS assay format was developed. During the first addition, a Cl⁻-free medium with or without test compound was added to each well. After 22 sec, a second addition of Cl⁻-free medium containing 2-10 μM forskolin was added to activate ΔF508-CFTR. The extracellular Cl⁻ concentration following both additions was 28 mM, which promoted Cl⁻ efflux in response to ΔF508-CFTR activation and the resulting membrane depolarization was optically monitored using the FRET-based voltage-sensor dyes.

Solutions

| | |
|---|---|
| Bath Solution #1: (in mM) | NaCl 160, KCl 4.5, CaCl$_2$ 2, MgCl$_2$ 1, HEPES 10, pH 7.4 with NaOH. |
| Chloride-free bath solution: | Chloride salts in Bath Solution #1 are substituted with gluconate salts. |
| CC2-DMPE: | Prepared as a 10 mM stock solution in DMSO and stored at −20° C. |
| DiSBAC$_2$(3): | Prepared as a 10 mM stock in DMSO and stored at −20° C. |

Cell Culture

NIH3T3 mouse fibroblasts stably expressing ΔF508-CFTR are used for optical measurements of membrane potential. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm$^2$ culture flasks. For all optical assays, the cells were seeded at 30,000/well in 384-well matrigel-coated plates and cultured for 2 hrs at 37° C. before culturing at 27° C. for 24 hrs. for the potentiator assay. For the correction assays, the cells are cultured at 27° C. or 37° C. with and without compounds for 16-24 hoursB) Electrophysiological Assays for assaying ΔF508-CFTR modulation properties of compounds 1. Using Chamber Assay Using chamber experiments were performed on polarized epithelial cells expressing ΔF508-CFTR to further characterize the ΔF508-CFTR modulators identified in the optical assays. FRT$^{ΔF508\text{-}CFTR}$ epithelial cells grown on Costar Snapwell cell culture inserts were mounted in an Using chamber (Physiologic Instruments, Inc., San Diego, Calif.), and the monolayers were continuously short-circuited using a Voltage-clamp System (Department of Bioengineering, University of Iowa, Iowa, and, Physiologic Instruments, Inc., San Diego, Calif.). Transepithelial resistance was measured by applying a 2-mV pulse. Under these conditions, the FRT epithelia demonstrated resistances of 4 KO/cm$^2$ or more. The solutions were maintained at 27° C. and bubbled with air. The electrode offset potential and fluid resistance were corrected using a cell-free insert. Under these conditions, the current reflects the flow of Cl⁻ through ΔF508-CFTR expressed in the apical membrane. The $I_{SC}$ was digitally acquired using an MP100A-CE interface and AcqKnowledge software (v3.2.6; BIOPAC Systems, Santa Barbara, Calif.).

Identification of Correction Compounds

Typical protocol utilized a basolateral to apical membrane Cl⁻ concentration gradient. To set up this gradient, normal ringer was used on the basolateral membrane, whereas apical NaCl was replaced by equimolar sodium gluconate (titrated to pH 7.4 with NaOH) to give a large Cl⁻ concentration gradient across the epithelium. All experiments were performed with intact monolayers. To fully activate ΔF508-CFTR, forskolin (10 μM) and the PDE inhibitor, IBMX (100 μM), were applied followed by the addition of the CFTR potentiator, genistein (50 μM).

As observed in other cell types, incubation at low temperatures of FRT cells stably expressing ΔF508-CFTR increases the functional density of CFTR in the plasma membrane. To determine the activity of correction compounds, the cells were incubated with 10 μM of the test compound for 24 hours at 37° C. and were subsequently washed 3× prior to recording. The cAMP- and genistein-mediated $I_{SC}$ in compound-treated cells was normalized to the 27° C. and 37° C. controls and expressed as percentage activity. Preincubation of the cells with the correction compound significantly increased the cAMP- and genistein-mediated $I_{SC}$ compared to the 37° C. controls.

Identification of Potentiator Compounds

Typical protocol utilized a basolateral to apical membrane Cl⁻ concentration gradient. To set up this gradient, normal ringers was used on the basolateral membrane and was permeabilized with nystatin (360 μg/ml), whereas apical NaCl was replaced by equimolar sodium gluconate (titrated to pH 7.4 with NaOH) to give a large Cl⁻ concentration gradient across the epithelium. All experiments were performed 30 min after nystatin permeabilization. Forskolin (10 μM) and all test compounds were added to both sides of the cell culture inserts. The efficacy of the putative ΔF508-CFTR potentiators was compared to that of the known potentiator, genistein.

Solutions

| | |
|---|---|
| Basolateral solution (in mM): | NaCl (135), CaCl$_2$ (1.2), MgCl$_2$ (1.2), K$_2$HPO$_4$ (2.4), KHPO$_4$ (0.6), N-2-hydroxyethylpiperazine-N'-2-ethanesulfonic acid (HEPES) (10), and dextrose (10). The solution was titrated to pH 7.4 with NaOH. |
| Apical solution (in mM): | Same as basolateral solution with NaCl replaced with Na Gluconate (135). |

Cell Culture

Fisher rat epithelial (FRT) cells expressing ΔF508-CFTR (FRT$^{ΔF508\text{-}CFTR}$) were used for Using chamber experiments for the putative ΔF508-CFTR modulators identified from our optical assays. The cells were cultured on Costar Snapwell cell culture inserts and cultured for five days at 37° C. and 5% CO$_2$ in Coon's modified Ham's F-12 medium supplemented with 5% fetal calf serum, 100 U/ml penicillin, and 100 μg/ml streptomycin. Prior to use for characterizing the potentiator activity of compounds, the cells were incubated at 27° C. for 16-48 hrs to correct for the ΔF508-CFTR. To determine the activity of corrections compounds, the cells were incubated at 27° C. or 37° C. with and without the compounds for 24 hours.

2. Whole-Cell Recordings

The macroscopic ΔF508-CFTR current ($I_{\Delta F508}$) in temperature- and test compound-corrected NIH3T3 cells stably expressing ΔF508-CFTR were monitored using the perforated-patch, whole-cell recording. Briefly, voltage-clamp recordings of $I_{\Delta F508}$ were performed at room temperature using an Axopatch 200B patch-clamp amplifier (Axon Instruments Inc., Foster City, Calif.). All recordings were acquired at a sampling frequency of 10 kHz and low-pass filtered at 1 kHz. Pipettes had a resistance of 5-6 MΩ when filled with the intracellular solution. Under these recording conditions, the calculated reversal potential for Cl⁻ ($E_{Cl}$) at room temperature was −28 mV. All recordings had a seal resistance >20 GΩ and a series resistance <15 MΩ. Pulse generation, data acquisition, and analysis were performed using a PC equipped with a Digidata 1320 A/D interface in conjunction with Clampex 8 (Axon Instruments Inc.). The bath contained <250 µl of saline and was continuously perifused at a rate of 2 ml/min using a gravity-driven perfusion system.

Identification of Correction Compounds

To determine the activity of correction compounds for increasing the density of functional ΔF508-CFTR in the plasma membrane, we used the above-described perforated-patch-recording techniques to measure the current density following 24-hr treatment with the correction compounds. To fully activate ΔF508-CFTR, 10 µM forskolin and 20 µM genistein were added to the cells. Under our recording conditions, the current density following 24-hr incubation at 27° C. was higher than that observed following 24-hr incubation at 37° C. These results are consistent with the known effects of low-temperature incubation on the density of ΔF508-CFTR in the plasma membrane. To determine the effects of correction compounds on CFTR current density, the cells were incubated with 10 µM of the test compound for 24 hours at 37° C. and the current density was compared to the 27° C. and 37° C. controls (% activity). Prior to recording, the cells were washed 3× with extracellular recording medium to remove any remaining test compound. Preincubation with 10 µM of correction compounds significantly increased the cAMP- and genistein-dependent current compared to the 37° C. controls.

Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I_{\Delta F508}$ with similar potency and efficacy observed in the optical assays. In all cells examined, the reversal potential before and during potentiator application was around −30 mV, which is the calculated $E_{Cl}$ (−28 mV).

Solutions

| | |
|---|---|
| Intracellular solution (in mM): | Cs-aspartate (90), CsCl (50), MgCl₂ (1), HEPES (10), and 240 µg/ml amphotericin-B (pH adjusted to 7.35 with CsOH). |
| Extracellular solution (in mM): | N-methyl-D-glucamine (NMDG)-Cl (150), MgCl₂ (2), CaCl₂ (2), HEPES (10) (pH adjusted to 7.35 with HCl). |

Cell Culture

NIH3T3 mouse fibroblasts stably expressing ΔF508-CFTR are used for whole-cell recordings. The cells are maintained at 37° C. in 5% CO₂ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

3. Single-Channel Recordings

The single-channel activities of temperature-corrected ΔF508-CFTR stably expressed in NIH3T3 cells and activities of potentiator compounds were observed using excised inside-out membrane patch. Briefly, voltage-clamp recordings of single-channel activity were performed at room temperature with an Axopatch 200B patch-clamp amplifier (Axon Instruments Inc.). All recordings were acquired at a sampling frequency of 10 kHz and low-pass filtered at 400 Hz. Patch pipettes were fabricated from Corning Kovar Sealing #7052 glass (World Precision Instruments, Inc., Sarasota, Fla.) and had a resistance of 5-8 MΩ when filled with the extracellular solution. The ΔF508-CFTR was activated after excision, by adding 1 mM Mg-ATP, and 75 nM of the cAMP-dependent protein kinase, catalytic subunit (PKA; Promega Corp. Madison, Wis.). After channel activity stabilized, the patch was perifused using a gravity-driven microperfusion system. The inflow was placed adjacent to the patch, resulting in complete solution exchange within 1-2 sec. To maintain ΔF508-CFTR activity during the rapid perifusion, the non-specific phosphatase inhibitor F⁻ (10 mM NaF) was added to the bath solution. Under these recording conditions, channel activity remained constant throughout the duration of the patch recording (up to 60 min). Currents produced by positive charge moving from the intra- to extracellular solutions (anions moving in the opposite direction) are shown as positive currents. The pipette potential ($V_p$) was maintained at 80 mV.

Channel activity was analyzed from membrane patches containing 2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o = I/i(N)$, where I=mean current, i=single-channel current amplitude, and N=number of active channels in patch.

Solutions

| | |
|---|---|
| Extracellular solution (in mM): | NMDG (150), aspartic acid (150), CaCl₂ (5), MgCl₂ (2), and HEPES (10) (pH adjusted to 7.35 with Tris base). |
| Intracellular solution (in mM): | NMDG-Cl (150), MgCl₂ (2), EGTA (5), TES (10), and Tris base (14) (pH adjusted to 7.35 with HCl). |

Cell Culture

NIH3T3 mouse fibroblasts stably expressing ΔF508-CFTR are used for excised-membrane patch-clamp recordings. The cells are maintained at 37° C. in 5% CO₂ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For single channel recordings, 2,500-5,000 cells were seeded on poly-L-lysine-coated glass coverslips and cultured for 24-48 hrs at 27° C. before use.

Compounds of the invention are useful as modulators of ATP binding cassette transporters. Table 3 below illustrates the EC50 and relative efficacy of certain embodiments in Table 1.

In Table 3 below, the following meanings apply:

TABLE 3

| Cmpd # | EC50 uM | % Activity |
|---|---|---|
| 1 | +++ | + |
| 2 | ++ | + |
| 3 | +++ | ++ |
| 4 | +++ | ++ |
| 5 | +++ | ++ |
| 6 | +++ | ++ |
| 7 | +++ | ++ |
| 8 | +++ | ++ |
| 9 | ++ | ++ |
| 10 | +++ | ++ |
| 11 | +++ | ++ |
| 12 | +++ | ++ |
| 13 | +++ | ++ |
| 14 | +++ | ++ |
| 15 | +++ | ++ |
| 16 | + | ++ |
| 17 | + | + |
| 18 | ++ | ++ |
| 19 | ++ | ++ |
| 20 | +++ | ++ |
| 21 | ++ | ++ |
| 22 | ++ | ++ |
| 23 | +++ | ++ |
| 24 | +++ | ++ |
| 25 | +++ | ++ |
| 26 | +++ | ++ |

EC50: "+++" means <1 uM; "++" means between 1 uM to 5 uM; "+" means greater than 5 uM.
% Efficacy: "+" means <25%; "++" means between 25% to 100%; "+++" means >100%.

What is claimed is:

1. A method of modulating ABC transporter activity comprising the step of contacting said ABC transporter with a compound of formula I:

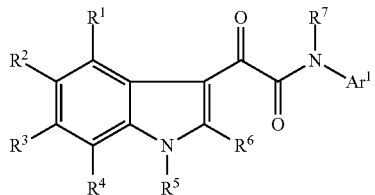

or a pharmaceutically acceptable salt thereof, wherein:
Ar$^1$ is a 5-6 membered aromatic monocyclic ring having 0-4 heteroatoms independently selected from nitrogen, oxygen, or sulfur, wherein said ring is optionally fused to a 5-12 membered monocyclic or bicyclic, aromatic, partially unsaturated, or saturated ring, wherein each ring contains 0-4 heteroatoms independently selected from nitrogen, oxygen, or sulfur, wherein Ar$^1$ has m substituents, each independently selected from —WR$^w$;
wherein each occurrence of WR$^W$ is selected from halo, cyano, CF$_3$, CHF$_2$, OCHF$_2$, Me, Et, CH(Me)$_2$, CHMeEt, n-propyl, t-butyl, OMe, OEt, OPh, O-fluorophenyl, O-difluorophenyl, O-methoxyphenyl, O-tolyl, O-benzyl, SMe, SCF$_3$, SCHF$_2$, SEt, CH$_2$CN, NH$_2$, NHMe, N(Me)$_2$, NHEt, N(Et)$_2$, C(O)CH$_3$, C(O)Ph, C(O)NH$_2$, SPh, SO$_2$-(amino-pyridyl), SO$_2$NH$_2$, SO$_2$Ph, SO$_2$NHPh, SO$_2$—N-morpholino, SO$_2$—N-pyrrolidyl, N-pyrrolyl, N-morpholino, 1-piperidyl, phenyl, benzyl, (cyclohexyl-methylamino)methyl, 4-Methyl-2, 4-dihydro-pyrazol-3-one-2-yl, benzimidazol-2yl, furan-2-yl, 4-methyl-4H-[1,2,4]triazol-3-yl, 3-(4'-chlorophenyl)-[1,2,4]oxadiazol-5-yl, NHC(O)Me, NHC(O)Et, NHC(O)Ph, 2-indolyl, 5-indolyl, —CH$_2$CH$_2$OH, —OCF$_3$, O-(2,3-dimethylphenyl), 5-methylfuryl, —SO$_2$-N-piperidyl, 2-tolyl, 3-tolyl, 4-tolyl, O-butyl, NHCO$_2$C(Me)$_3$, CO$_2$C(Me)$_3$, isopropenyl, n-butyl, O-(2,4-dichlorophenyl), NHSO$_2$PhMe, O-(3-chloro-5-trifluoromethyl-2-pyridyl), phenylhydroxymethyl, 2,5-dimethylpyrrolyl, NHCOCH$_2$C(Me)$_3$, O-(2-tert-butyl) phenyl, 2,3-dimethylphenyl, 3,4-dimethylphenyl, 4-hydroxymethyl phenyl, 4-dimethylaminophenyl, 2-trifluoromethylphenyl, 3- trifluoromethylphenyl, 4-trifluoromethylphenyl, 4-cyanomethylphenyl, 4-isobutylphenyl, 3-pyridyl, 4-pyridyl, 4-isopropylphenyl, 3-isopropylphenyl, 2-methoxyphenyl, 3-methoxyphenyl, 4-methoxyphenyl, 3,4-methylenedioxyphenyl, 2-ethoxyphenyl, 3-ethoxyphenyl, 4-ethoxyphenyl, 2-methylthiophenvl, 4-methylthiophenyl, 2,4-dimethoxyphenyl, 2,5-dimethoxyphenyl, 2,6-dimethoxyphenyl, 3,4-dimethoxyphenyl, 5-chloro-2-methoxyphenyl, 2-OCF$_3$-phenyl, 3-trifluoromethoxyphenyl, 4-trifluoromethoxyphenyl, 2-phenoxyphenyl, 4-phenoxyphenyl, 2-fluoro-3-methoxy-phenyl, 2,4-dimethoxy-5-pyrimidyl, 5-isopropyl-2-methoxyphenyl, 2-fluorophenyl, 3-fluorophenyl, 4-fluorophenyl, 3-cyanophenyl, 3-chlorophenyl, 4-chlorophenyl, 2,3-difluorophenyl, 2,4-difluorophenyl, 2,5-difluorophenyl, 3,4-difluorophenyl, 3,5-difluorophenyl, 3-chloro-4-fluorophenyl, 3,5-dichlorophenyl, 2,5-dichlorophenvl, 2,3-dichlorophenyl, 3,4-dichlorophenyl, 2,4-dichlorophenyl, 3-methoxycarbonylphenyl, 4-methoxycarbonyl phenyl, 3-isopropyloxycarbonylphenyl, 3-acetamidophenyl, 4-fluoro-3-methylphenyl, 4-methanesulfinyl-phenyl, 4-methanesulfonyl-phenyl, 4-N-(2-N,N-dimethylaminoethyl) carbamoylphenyl, 5-acetyl-2-thienyl, 2-benzothienyl, 3-benzothienyl, furan-3-yl, 4-methyl-2-thienyl, 5-cyano-2-thienyl, N'-phenylcarbonyl-N-piperazinyl, —NHCO$_2$Et, —NHCO$_2$Me, N-pyrrolidinyl, —NHSO$_2$(CH$_2$)$_2$N-piperidine, —NHSO$_2$(CH$_2$)$_2$ N-morpholine, —NHSO$_2$(CH$_2$)$_2$N(Me)$_2$, COCH$_2$N(Me)COCH$_2$NHMe, —CO$_2$Et, O-propyl, —CH$_2$CH$_2$NHCO$_2$C(Me)$_3$, hydroxy, aminomethyl, pentyl, adamantly, cyclopentyl, ethoxyethyl, C(Me)$_2$CH$_2$OH, C(Me)$_2$CO$_2$Et, —CHOHMe, CH$_2$CO$_2$Et, —C(Me)$_2$CH$_2$NHCO$_2$C(Me)$_3$, O(CH$_2$)$_2$OEt, O(CH$_2$)$_2$OH CO$_2$Me, hydroxymethyl, 1-methyl-1-cyclohexyl, 1-methyl-1-cyclooctyl, 1-methyl-1-cycloheptyl, C(Et)$_2$C(Me)$_3$, C(Et)$_3$, CONHCH$_2$CH(Me)$_2$, 2-aminomethylphenyl, ethenyl, 1-piperidinylcarbonyl, ethynyl, cyclohexyl, 4-methylpiperidinyl, —OCO$_2$Me, —C(Me)$_2$CH$_2$NHCO$_2$CH$_2$CH(Me)$_2$, —C(Me)$_2$CH$_2$NHCO$_2$CH$_2$CH$_2$CH$_3$, —C(Me)$_2$CH$_2$NHCO$_2$Et, —C(Me)$_2$CH$_2$NHCO$_2$Me, —C(Me)$_2$CH$_2$NHCO$_2$CH$_2$C(Me)$_3$, —CH$_2$NHCOCF$_3$, —CH$_2$NHCO$_2$C(Me)$_3$, —C(Me)$_2$CH$_2$NHCO$_2$(CH$_2$)$_3$, C(Me)$_2$CH$_2$NHCO$_2$(CH$_2$)$_2$OMe, C(OH) (CF$_3$)$_2$, —C(Me)$_2$CH$_2$NHCO$_2$CH$_2$-tetrahydrofuran-3-yl, C(Me)$_2$CH$_2$O (CH$_2$)$_2$OMe, or 3-ethyl-2,6-dioxopiperidin-3-yl;
m is 0-5;
each of R$^1$, R$^2$, R$^3$, and R$^4$ is independently —X—R$^x$;
X is a bond or is an optionally substituted C$_1$-C$_6$ alkylidene chain wherein up to two methylene units of X are optionally and independently replaced by —CO—, —CS—, —COCO—, —CONR'—, —CONR'NR'—, —CO$_2$—, —OCO—, —NR'CO$_2$—, —O—, —NR'CONR'—, —OCONR'—, —NR'NR', —NR'NR'CO—, —NR'CO—, —S—, —SO, —SO$_2$—, —NR'—, —SO$_2$NR'—, NR'SO$_2$—, or —NR'SO$_2$NR'—;

R$^x$ is independently R', halo, NO$_2$, CN, CF$_3$, or OCF$_3$; R$^5$ is hydrogen;

R$^6$ is hydrogen, CF$_3$, —OR', —SR', or an optionally substituted C$_{1-6}$ aliphatic group;

R$^7$ is hydrogen;

R' is independently selected from hydrogen or an optionally substituted group selected from a C$_1$-C$_8$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur; and provided that the following compounds of FIG. 1 are excluded:

4)
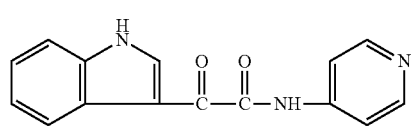
1H-Indole-3-acetamide, α-oxo-N-4-pyridinyl-

5)
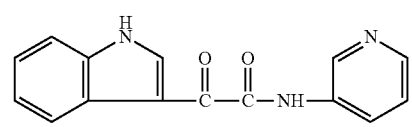
1H-Indole-3-acetamide, α-oxo-N-3-pyridinyl-

6)
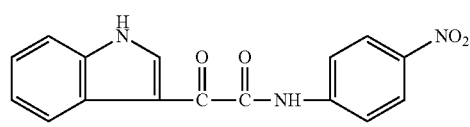
1H-Indole-3-acetamide, N-(4-nitrophenyl)-α-oxo-

7)
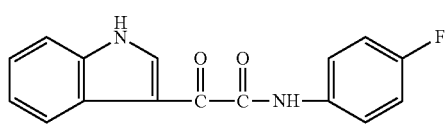
1H-Indole-3-acetamide, N-(4-fluorophenyl)-α-oxo-

8)
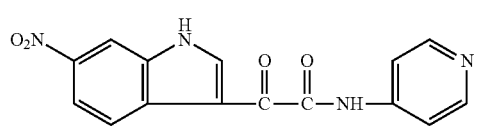
1H-Indole-3-acetamide, 6-nitro-α-oxo-N-4-pyridinyl-

9)
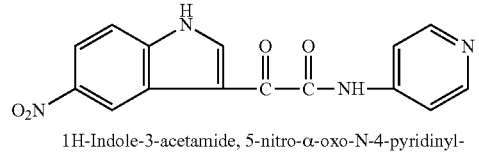
1H-Indole-3-acetamide, 5-nitro-α-oxo-N-4-pyridinyl-

10)
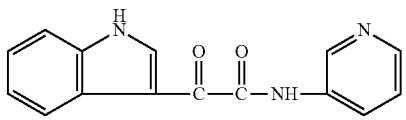
1H-Indole-3-acetamide, α-oxo-N-3-pyridinyl-

11)
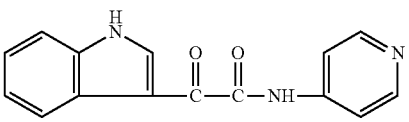
1H-Indole-3-acetamide, α-oxo-N-3-pyridinyl-

13)
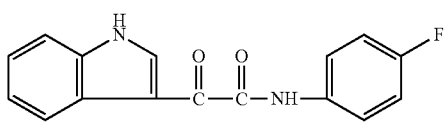
1H-Indole-3-acetamide, N-(4-fluorophenyl)-α-oxo-

22)
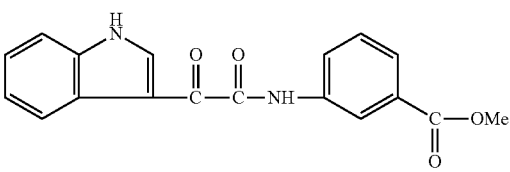
Benzoic acid, 3-[(1H-indol-3-yloxoacetyl)amino]-, methyl ester

23)
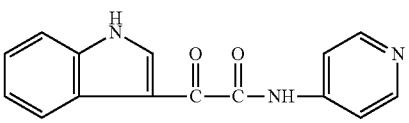
1H-Indole-3-acetamide, α-oxo-N-4-pyridinyl-

26)
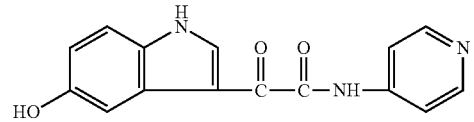
1H-Indole-3-acetamide, 5-hydroxy-α-oxo-N-4-pyridinyl-

27)
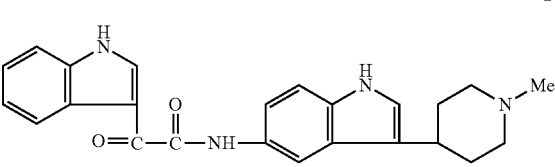
1H-Indole-3-acetamide, N-[3-(1-methyl-4-piperidinyl)-1H-indol-5-yl]-α-oxo- 29) 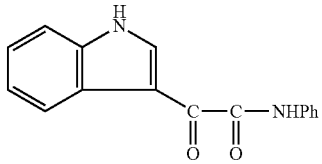
1H-Indole-3-acetamide, α-oxo-N-phenyl- 30) 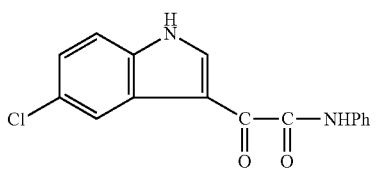
1H-Indole-3-acetamide, 5-chloro-α-oxo-N-phenyl- 31) 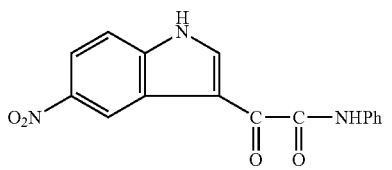
1H-Indole-3-acetamide, 5-nitro-α-oxo-N-phenyl- 32) 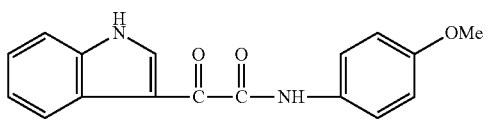
1H-Indole-3-acetamide, N-(4-methoxyphenyl)-α-oxo- 33) 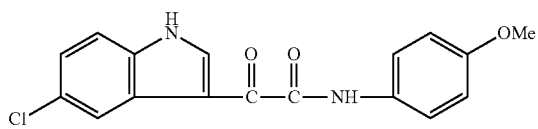
1H-Indole-3-acetamide, 5-chloro-N-(4-methoxyphenyl)-α-oxo- 34) 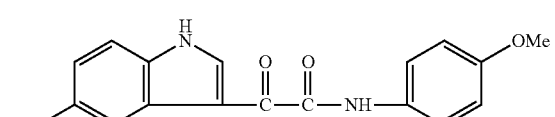
1H-Indole-3-acetamide, N-(4-methoxyphenyl)-5-nitro-α-oxo- 35) 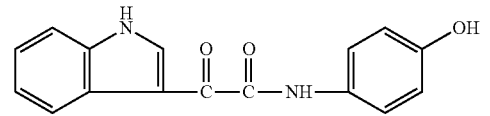
1H-Indole-3-acetamide, N-(4-hydroxyphenyl)-α-oxo- (9CI)

36) 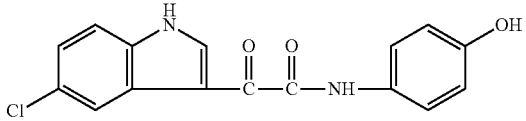
1H-Indole-3-acetamide, 5-chloro-N-(4-hydroxyphenyl)-α-oxo-

37) 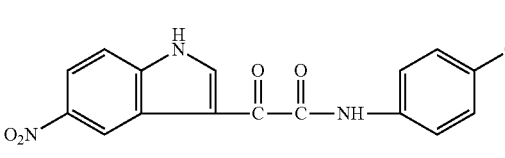
1H-Indole-3-acetamide, N-(4-hydroxyphenyl)-5-nitro-α-oxo-

38) 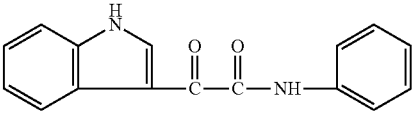
1H-Indole-3-acetamide, α-oxo-N-3-pyridinyl-

39) 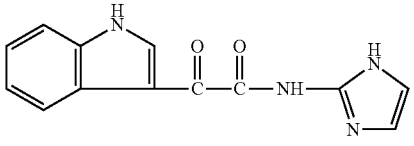
1H-Indole-3-acetamide, N-1H-imidazol-2-yl-α-oxo-

40) 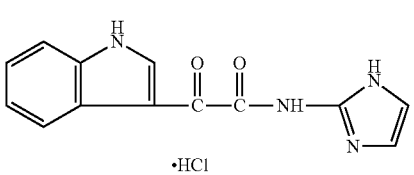
1H-Indole-3-acetamide, N-1H-imidazol-2-yl-α-oxo-, monohydrochloride 41) 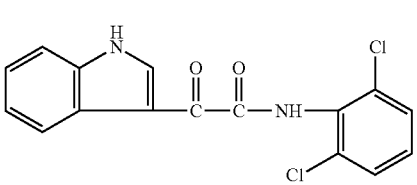
1H-Indole-3-acetamide, N-(2,6-dichlorophenyl)-α-oxo- 42) 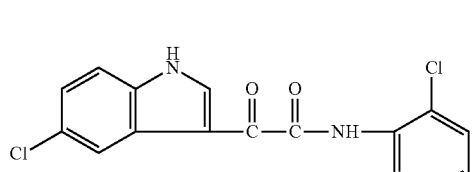
1H-Indole-3-acetamide, 5-chloro-N-(2,6-dichlorophenyl)-α-oxo- 43) 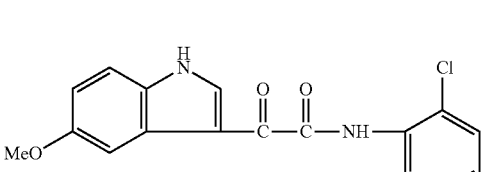
1H-Indole-3-acetamide, N-(2,6-dichlorophenyl)-5-methoxy-α-oxo- 44)
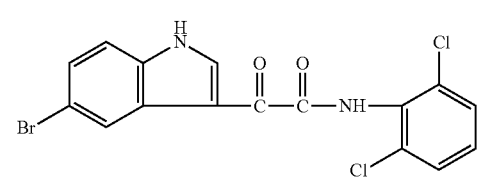

1H-Indole-3-acetamide, 5-bromo-N-(2,6-dichlorophenyl)-α-oxo-

45)
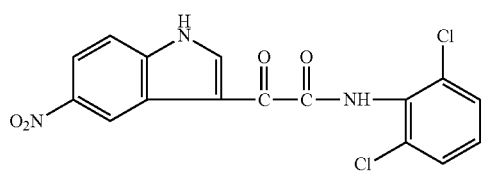

1H-Indole-3-acetamide, N-(2,6-dichlorophenyl)-5-nitro-α-oxo-

46)
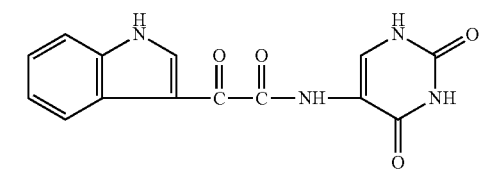

1H-Indole-3-acetamide,
α-oxo-N-(1,2,3,4-tetrahydro-2,4-dioxo-5-pyrimidinyl)-

47)
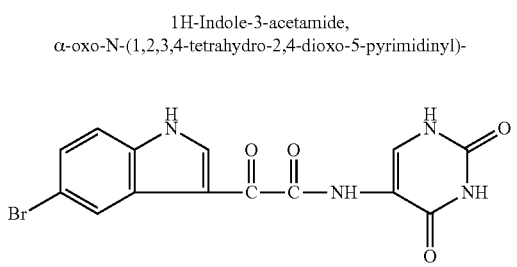

1H-Indole-3-acetamide,
5-bromo-α-oxo-N-(1,2,3,4-tetrahydro-2,4-dioxo-5-pyrimidinyl)-

48)
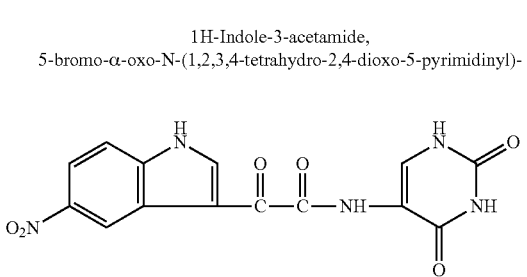

1H-Indole-3-acetamide,
5-nitro-α-oxo-N-(1,2,3,4-tetrahydro-2,4-dioxo-5-pyrimidinyl)-

50)
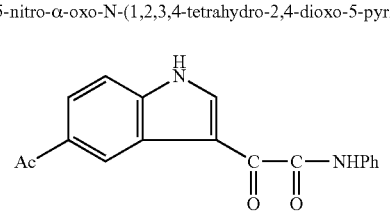

1H-Indole-3-acetamide, 5-acetyl-α-oxo-N-phenyl-

51)
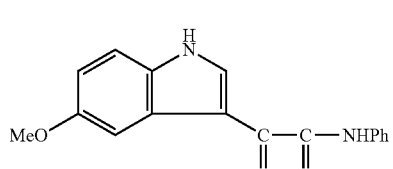

Indole-3-glyoxylanilide, 5-methoxy-

52)
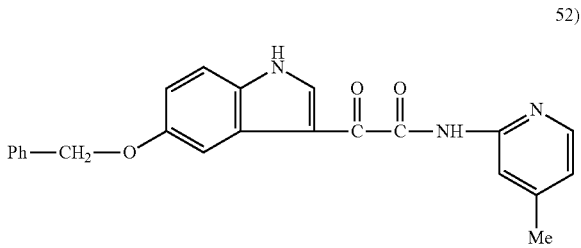

Indole-3-glyoxylamide, 5-(benzyloxy)-N-(4-methyl-2-pyridyl)-

53)
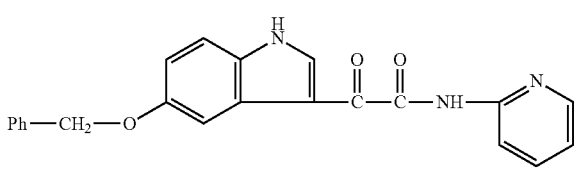

Indole-3-glyoxylamide, 5-(benzyloxy)-N-2-pyridyl-

54)
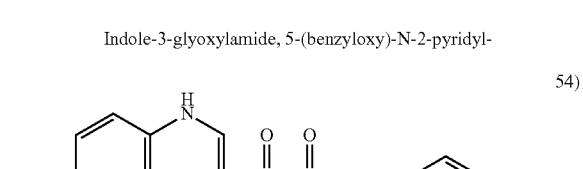

Anthranilic acid, N-(indol-3-ylglyoxyloyl)-

55)
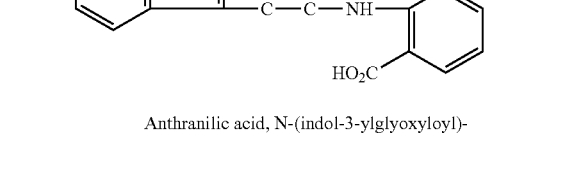

Benzoic acid, p-(2-indol-3-ylglyoxylamido)-

56)
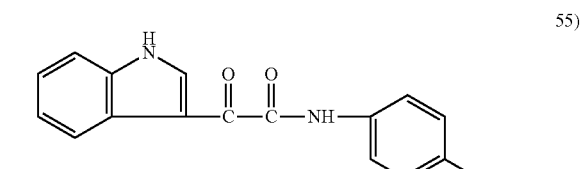

Indole-3-glyoxylanilide, 4′-acetyl-

57)
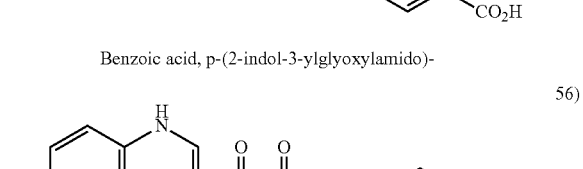

Benzoic acid, m-(2-indol-3-ylglyoxylamido)-

58)
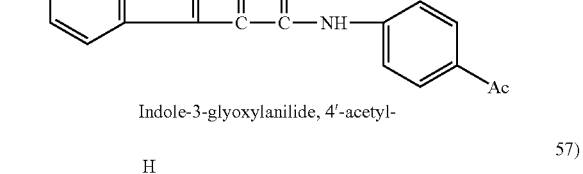

1H-Indole-3-acetamide, α-oxo-N-phenyl-

59)

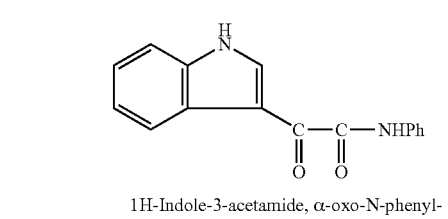

1H-Indole-3-acetamide, α-oxo-N-phenyl-

60)

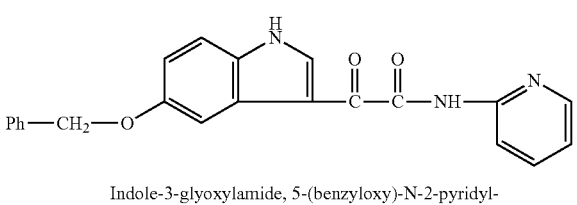

Indole-3-glyoxylamide, 5-(benzyloxy)-N-2-pyridyl-

61)

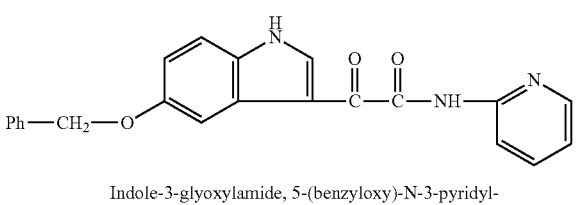

Indole-3-glyoxylamide, 5-(benzyloxy)-N-3-pyridyl-

62)

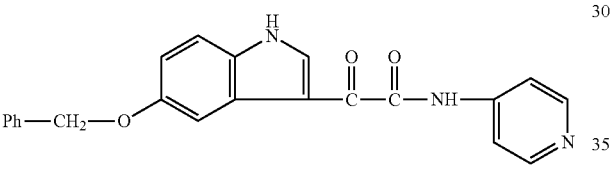

Indole-3-glyoxylamide, 5-(benzyloxy)-N-4-pyridyl-

63)

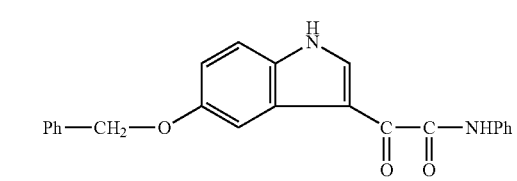

Indole-3-glyoxylanilide, 5-(benzyloxy)-

65)

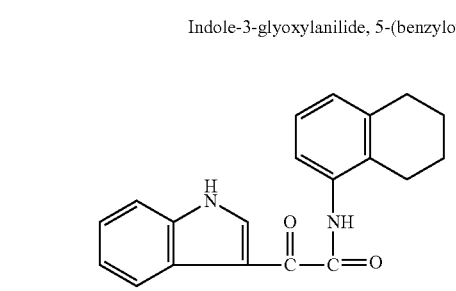

1H-Indole-3-acetamide, α-oxo-N-(5,6,7,8-tetrahydro-1-naphthalenyl)-
(9CI) (CA INDEX NAME)

67)

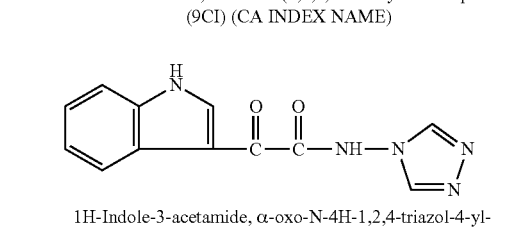

1H-Indole-3-acetamide, α-oxo-N-4H-1,2,4-triazol-4-yl-

69)

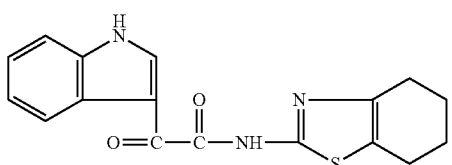

1H-Indole-3-acetamide, α-oxo-N-(4,5,6,7-tetrahydro-2-benzothiazolyl)-

71)

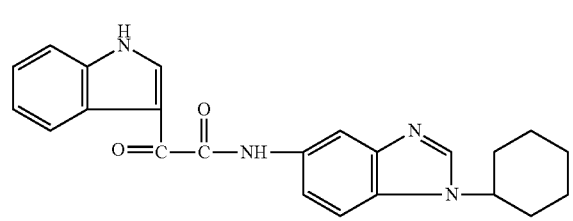

1H-Indole-3-acetamide, N-(1-cyclohexyl-1H-benzimidazol-5-yl)-α-oxo-

72)

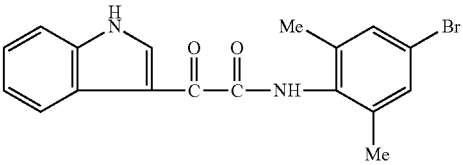

1H-Indole-3-acetamide, N-(4-bromo-2,5-dimethylphenyl)-α-oxo-

74)

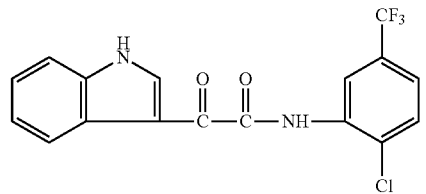

1H-Indole-3-acetamide, N-[2-chloro-5-(trifluromethyl)phenyl]-α-oxo-

75)

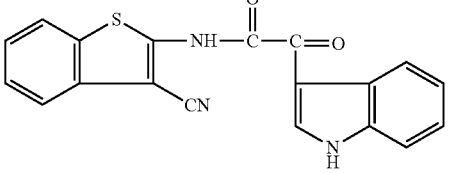

1H-Indole-3-acetamide, N-[3-cyanobenzo[b]thien-2-yl]-α-oxo-

76)

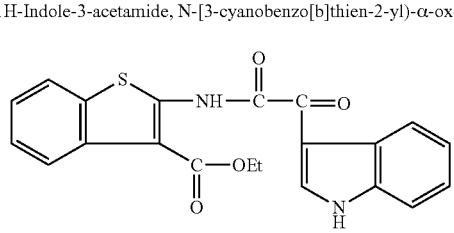

Benzo(b)thiophene-3-carboxylic acid,
2-((1H-indol-3-yloxoacetyl)amino-, ethyl ester

77)

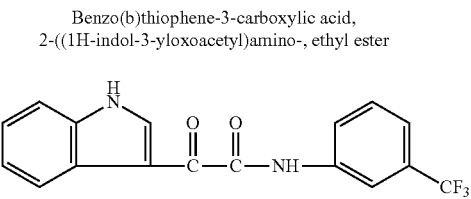

1H-Indole-3-acetamide, α-oxo-N-[3-(trifluoromethyl)phenyl]-

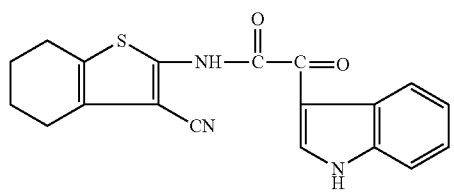

78) 1H-Indole-3-acetamide, N-(3-cyano-4,5,6,7-tetrahydrobenzo[b]thien-2-yl)-α-oxo-

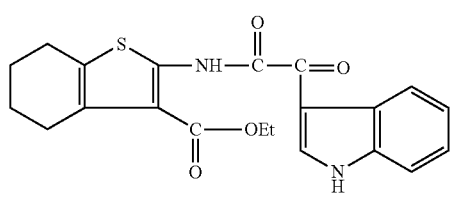

79) Benzo[b]thiophene-3-carboxylic acid, 4,5,6,7-tetrahydro-2-[(1H-indol-3-yloxoacetyl)amino]-, ethyl ester

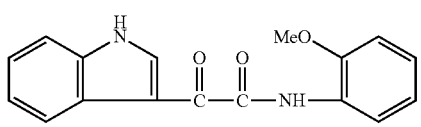

80) 1H-Indole-3-acetamide, N-(2-methoxyphenyl)-α-oxo-

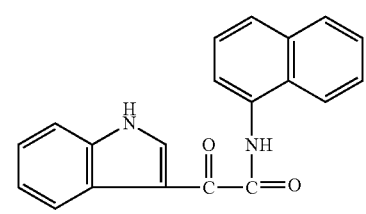

81) 1H-Indole-3-acetamide, N-1-naphthalenyl-α-oxo-

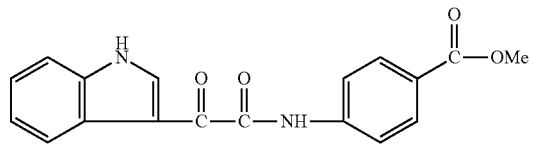

82) Benzoic acid, 4-[(1H-indol-3-yloxoacetyl)amino]-, methyl ester

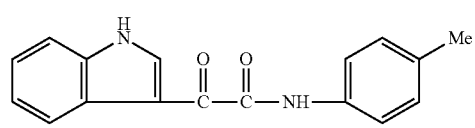

83) 1H-Indole-3-acetamide, N-(4-methylphenyl)-α-oxo-

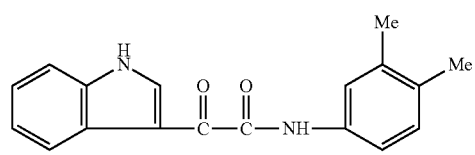

84) 1H-Indole-3-acetamide, N-(3,4-dimethylphenyl)-α-oxo-

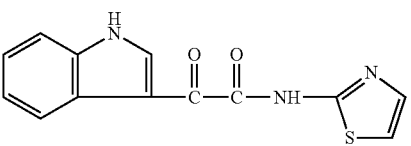

85) 1H-Indole-3-acetamide, α-oxo-N-2-thioxolyl-

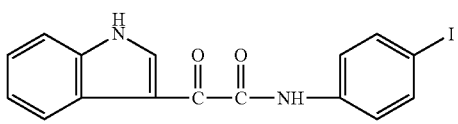

87) 1H-Indole-3-acetamide, N-(4-iodophenyl)-α-oxo-

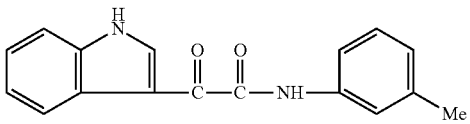

88) 1H-Indole-3-acetamide, N-(3-methylphenyl)-α-oxo-

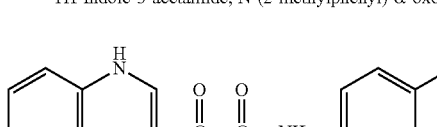

89) 1H-Indole-3-acetamide, N-(2-methylphenyl)-α-oxo-

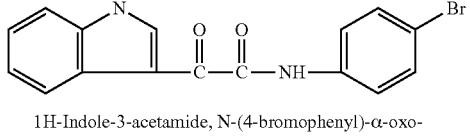

90) 1H-Indole-3-acetamide, N-(4-bromophenyl)-α-oxo-

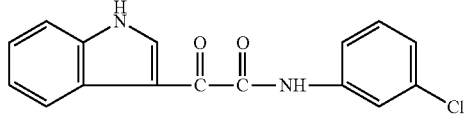

91) 1H-Indole-3-acetamide, N-(3-chlorophenyl)-α-oxo- 92) 1H-Indole-3-acetamide, N-(4-ethoxyphenyl)-α-oxo-

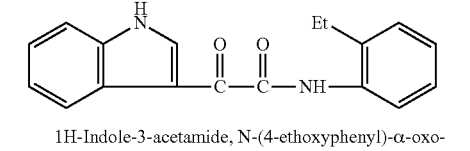

93) 1H-Indole-3-acetamide, N-(4-ethoxyphenyl)-α-oxo-

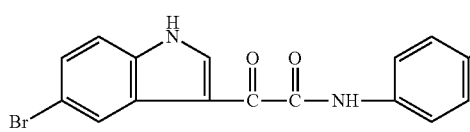

94) 1H-Indole-3-acetamide, 5-bromo-N-(4-fluorophenyl)-α-oxo-

-continued

96)

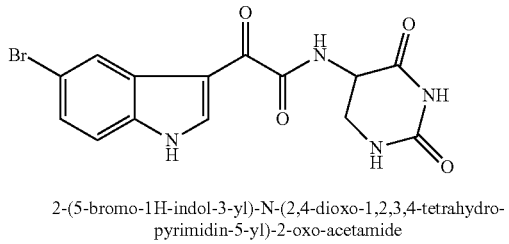

2-(5-bromo-1H-indol-3-yl)-N-(2,4-dioxo-1,2,3,4-tetrahydro-pyrimidin-5-yl)-2-oxo-acetamide

97)

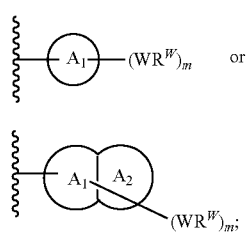

N-(2,4-dioxo-1,2,3,4-tetrahydro-pyrimidin-5-yl)-2-(5-nitro-1H-indol-3-yl)-2-oxo-acetamide.

2. The method according to claim 1, wherein $Ar^1$ is selected from:

a-i

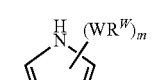

a-ii

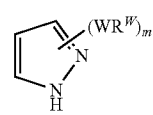

wherein ring $A_1$ 5-6 membered aromatic monocyclic ring having 0-4 heteroatoms independently selected from nitrogen, oxygen, or sulfur; or $A_1$ and $A_2$, together, is an 8-14 membered aromatic, bicyclic or tricyclic ring, wherein each ring contains 0-4 heteroatoms independently selected from nitrogen, oxygen, or sulfur.

3. The method according to claim 2, wherein $A_1$ is an optionally substituted 6membered aromatic ring having 0-4 heteroatoms, wherein said heteroatom is nitrogen.

4. The method according to claim 3, wherein $A_1$ is an optionally substituted phenyl, pyridyl, pyrimidinyl, pyrazinyl or triazinyl.

5. The method according to claim 2, wherein $A_1$ is an optionally substituted 5-membered aromatic ring having 0-3 heteroatoms independently selected from nitrogen, oxygen, or sulfur.

6. The method according to claim 2, wherein $A_2$ is an optionally substituted 5-6 membered aromatic ring having 0-4 heteroatoms independently selected from nitrogen, oxygen, or sulfur.

7. The method according to claim 6, wherein $A_2$ is an optionally substituted 5-membered aromatic ring having 0-3 heteroatoms independently selected from nitrogen, oxygen, or sulfur.

8. The method according to claim 2, wherein $A_2$ is selected from:

i

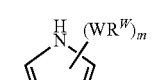

ii

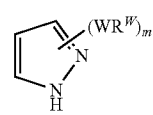

iii

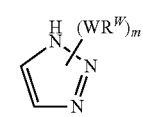

iv

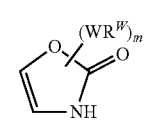

v

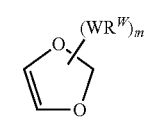

vi

vii

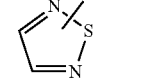

viii

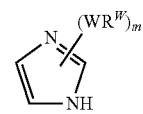

ix

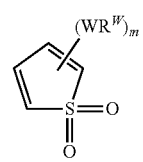

x

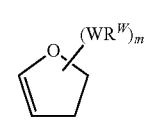

xi

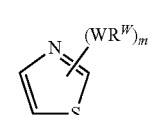

xii

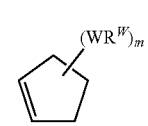

wherein ring $A_2$ is fused to ring $A_1$ through two adjacent carbon ring atoms.

9. The method according to claim 1, wherein m is 0-4.

10. The method according to claim 1, wherein $R^5$ is hydrogen or optionally substituted $C_{1-4}$ aliphatic group.

11. The method according to claim 1, wherein $R^6$ is hydrogen, optionally substituted $C_{1-4}$ aliphatic group, —(O—$C_{1-4}$ aliphatic), or —(S—$C_{1-4}$ aliphatic).

12. The method according to claim 1, wherein X is a bond or an optionally substituted $C_{1-6}$ alkylidene chain wherein one or two non-adjacent methylene units are optionally and independently replaced by O, NR', S, $SO_2$, or COO, or CO.

13. The method according to claim 1, wherein $R^X$ is R' or halo.

14. The method according to claim 1, wherein each occurrence of $XR^X$ is selected from —$C_{1-3}$alkyl, —O($C_{1-3}$alkyl), —$CF_3$, —$OCF_3$, —$SCF_3$, —F, —Cl, —Br, $SO_2NH_2$, —COOR', —COR', —O(CH$_2$)$_2$N(R')(R'), —O(CH$_2$)N(R')(R'), —CON(R')(R'), —(CH$_2$)$_2$OR', —(CH$_2$)OR', optionally substituted phenyl, —N(R')(R'), —(CH$_2$)$_2$N(R')(R'), or —(CH$_2$)N(R')(R').

15. The method according to claim 1, wherein said compounds have formula IIA or formula IIB:

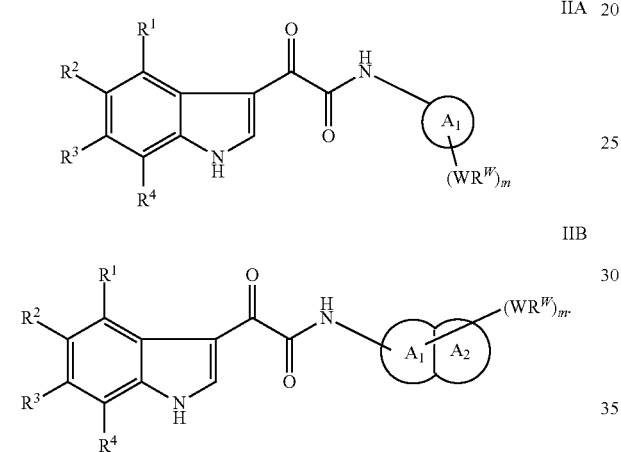

16. The method according to claim 1, wherein said compound has formula IIIA, formula IIIB, formula IIIC, formula IIID, or formula IIIE:

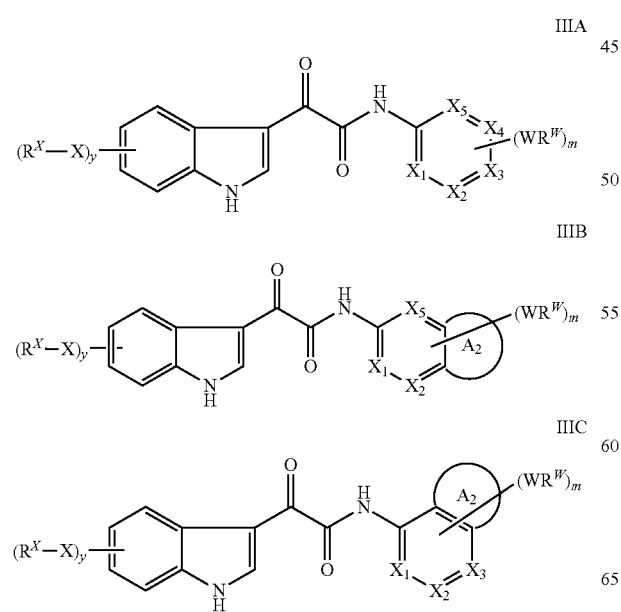

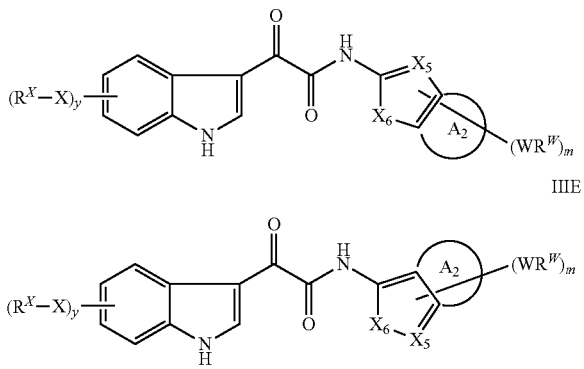

Wherein:
each of $X_1$, $X_2$, $X_3$, $X_4$, and $X_5$ is independently selected from CH or N;
$X_6$ is O, S, or NH; and
y is 0-4.

17. The method according to claim 16, wherein $X_1$, $X_2$, $X_3$, $X_4$, and $X_5$ taken together with $WR^W$ and m in formula IIIA, is optionally substituted phenyl.

18. The method according to claim 16, wherein $X_1$, $X_2$, $X_3$, $X_4$, and $X_5$ taken together in formula IIIA is an optionally substituted ring selected from:

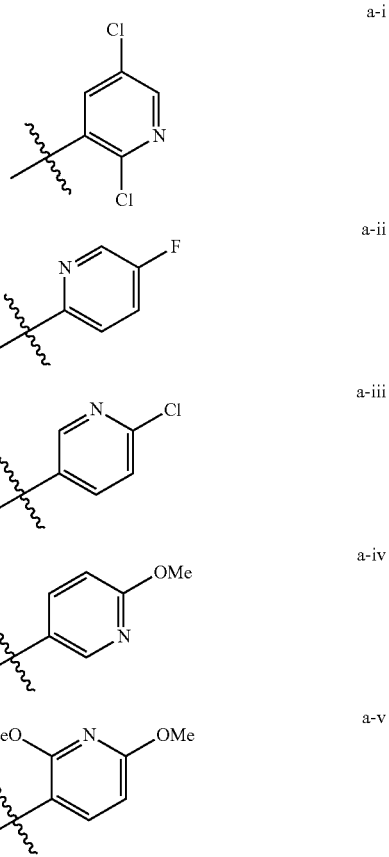

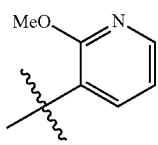 a-vi
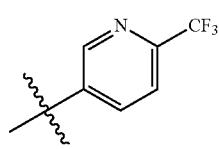 a-vii
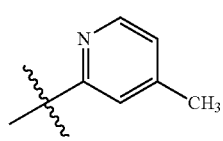 a-viii
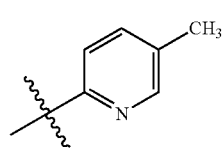 a-ix
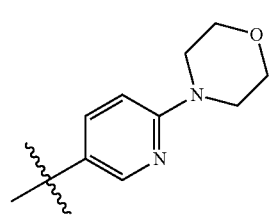 a-x
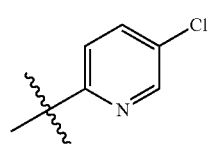 a-xi
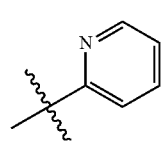 a-xii
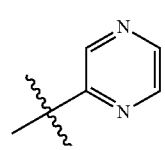 a-xiii
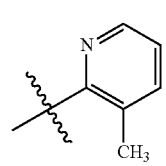 a-xiv
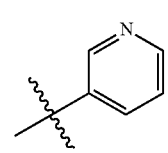 a-xv
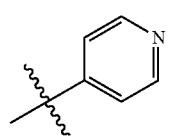 a-xvi
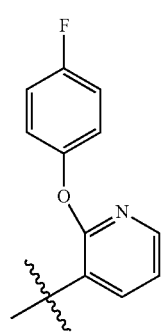 a-xvii
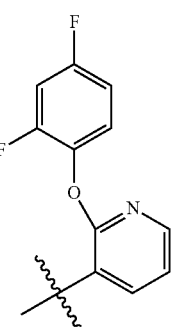 a-xviii
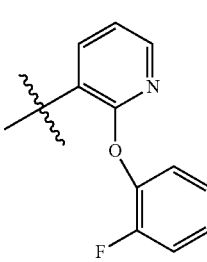 a-xix
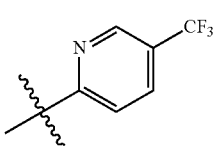 a-xx
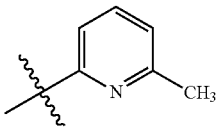 a-xxi
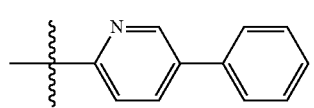 a-xxii -continued
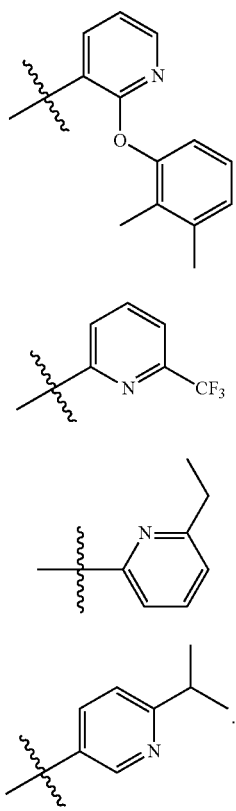
a-xxiii
a-xxiv
a-xxv
a-xxvi
19. The method according to claim 16, wherein $X_1$, $X_2$, $X_3$, $X_4$, $X_5$, or $X_6$, taken together with ring $A_2$ in formula IIIB, formula IIIC, formula IIID, or formula IIIE, is an optionally substituted ring selected from:
b-i
b-ii
b-iii
b-iv
-continued
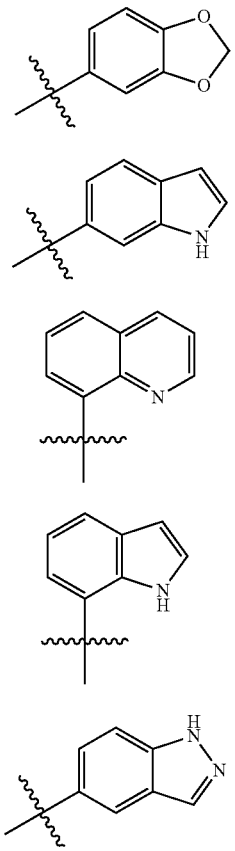
b-v
b-vi
b-vii
b-viii
b-vix
b-x
b-xi
b-xii
b-xiii

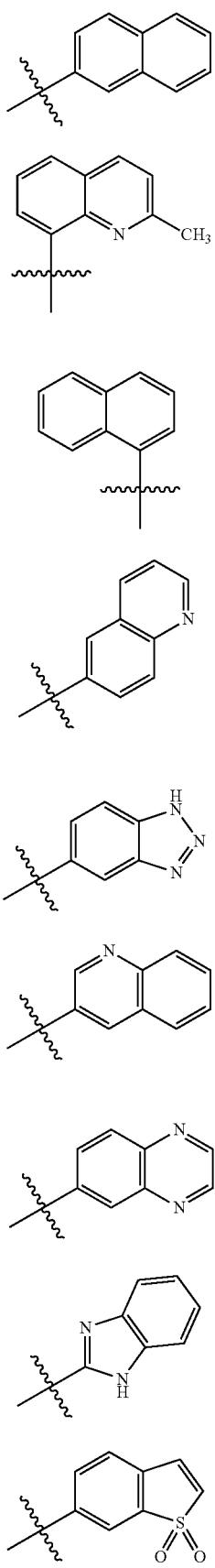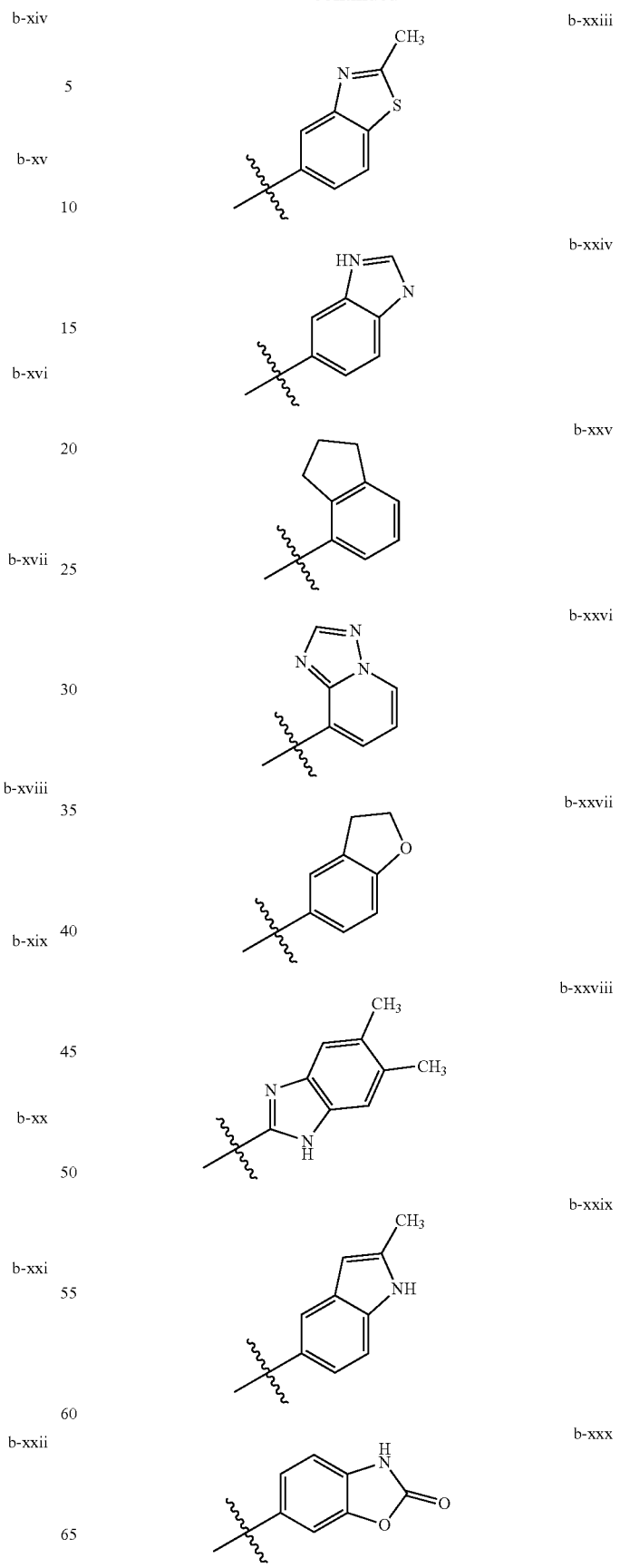

-continued b-xxxi b-xxxii b-xxxiii b-xxxiv b-xxxv b-xxxvi b-xxxvii

-continued b-xxxviii b-xxxix b-xL b-xLi b-xLii b-xLiii b-xLiv b-xLv b-xLvi

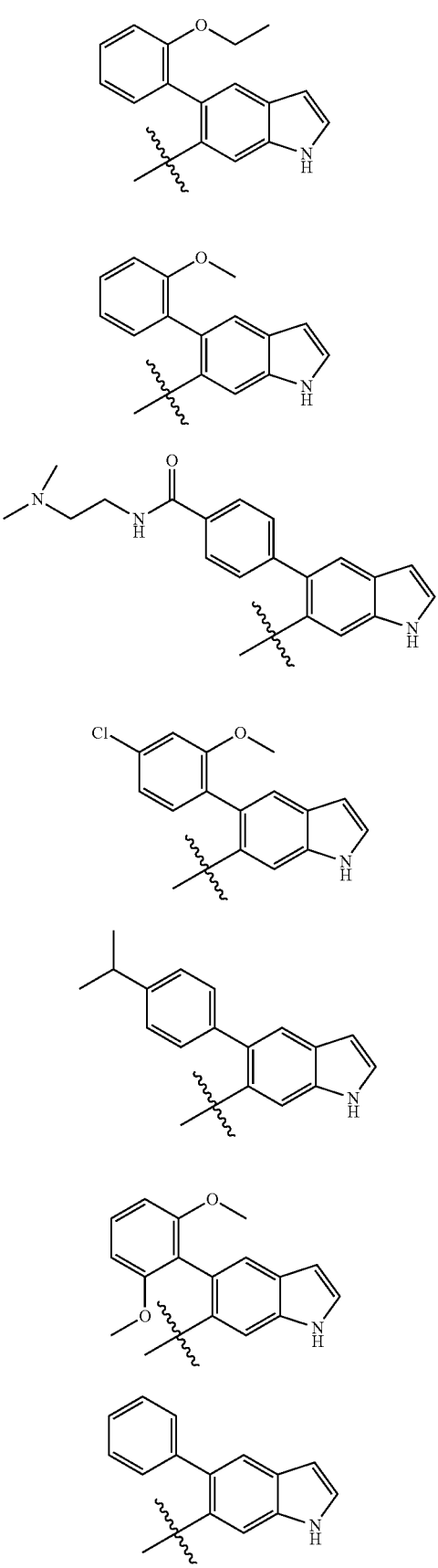

| b-Lxii | 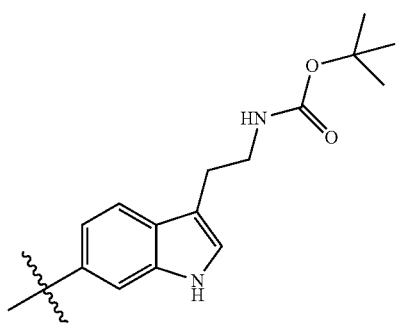 |
| --- | --- |
| b-Lxiii | 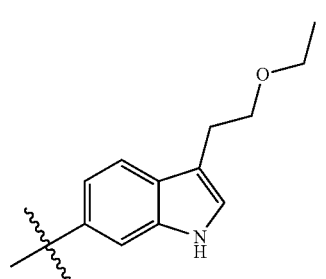 |
| b-Lxiv | 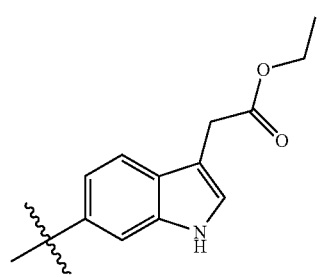 |
| b-Lxv | 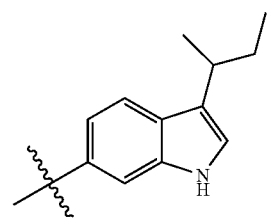 |
| b-Lxvi | 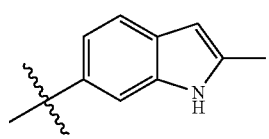 |
| b-Lxvii | 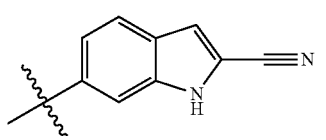 |
| b-Lxviii | 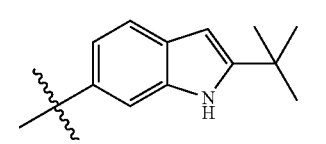 |
| b-Lxix | 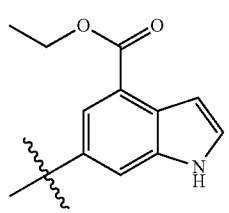 |
| b-Lxx | 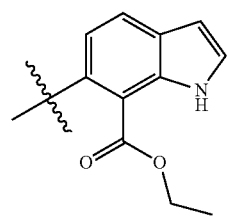 |
| b-Lxxi | 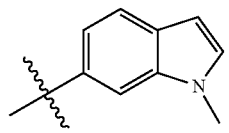 |
| b-Lxxii | 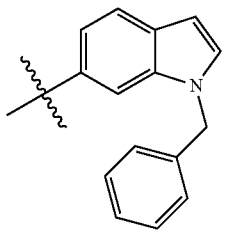 |
| b-Lxxiii | 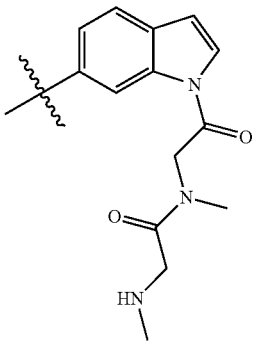 |
| b-Lxxiv | 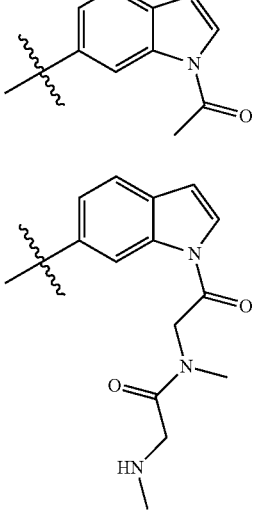 |
| b-Lxxv | 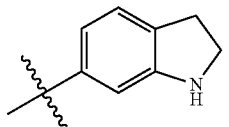 | b-Lxxvi 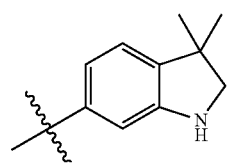
b-Lxxvii 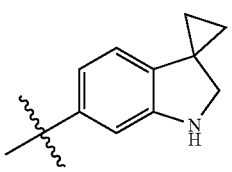
b-Lxxviii 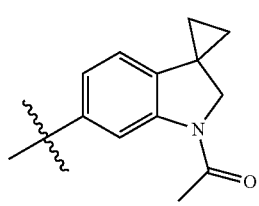
b-Lxxix 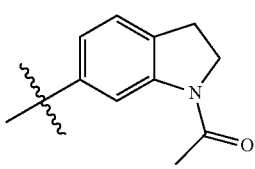
b-Lxxx 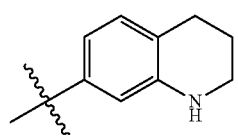
b-Lxxxi 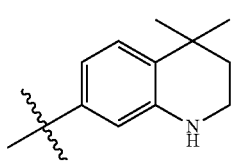
b-Lxxxii 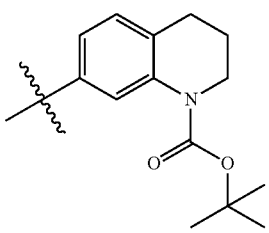
b-Lxxxiii 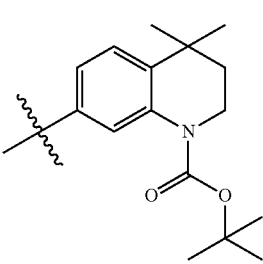
b-Lxxxiv 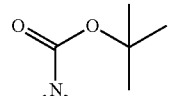
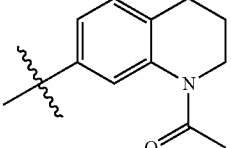
b-Lxxxv 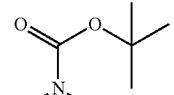
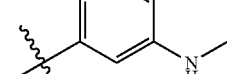
b-Lxxxvi 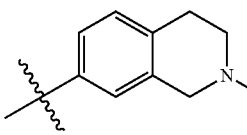
b-Lxxxvii 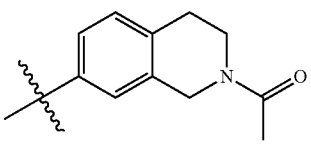
b-Lxxxix 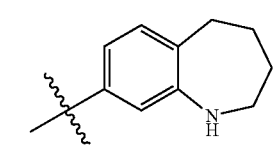
b-xC 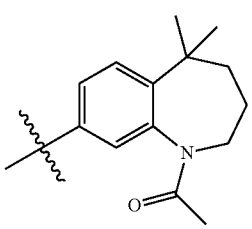
b-xCi 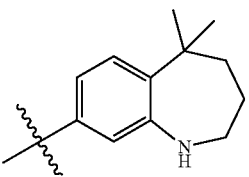

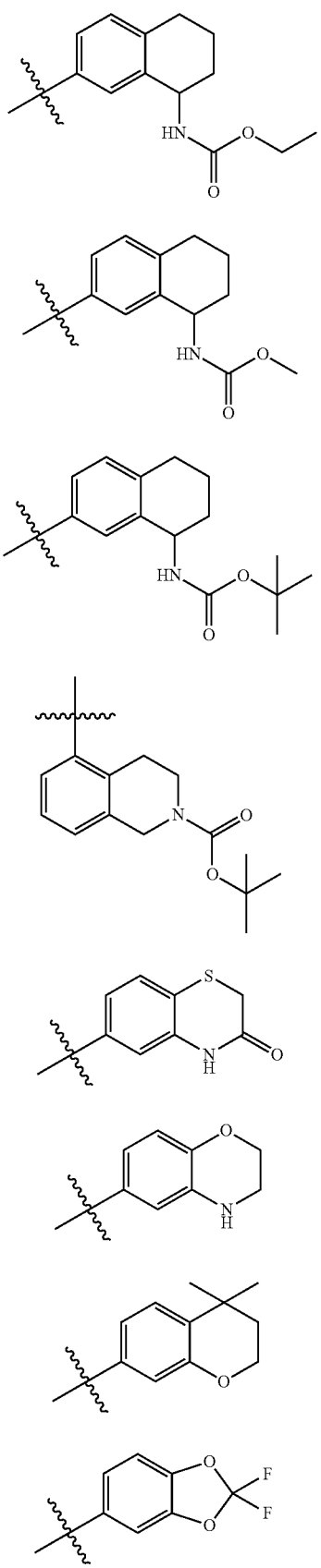
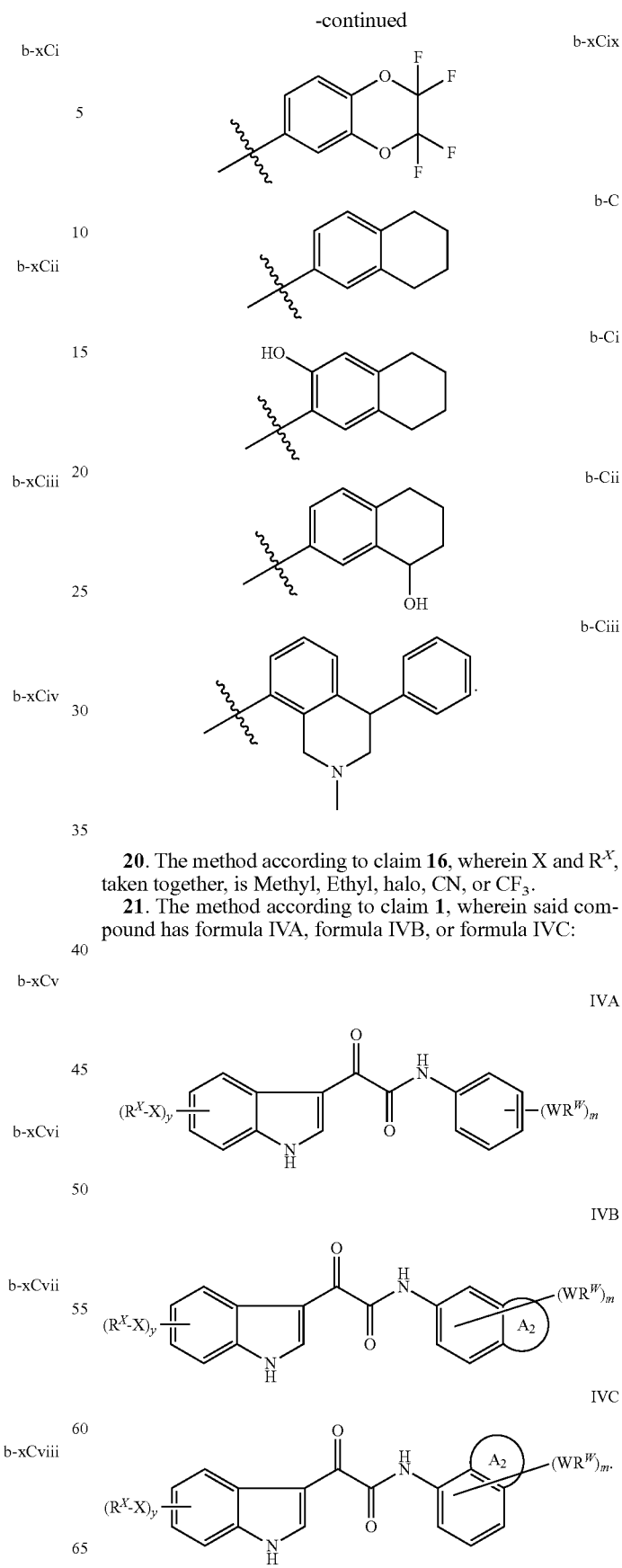
20. The method according to claim 16, wherein X and $R^X$, taken together, is Methyl, Ethyl, halo, CN, or $CF_3$.
21. The method according to claim 1, wherein said compound has formula IVA, formula IVB, or formula IVC:

22. The method according to claim 21, wherein ring $A_2$ is an optionally substituted, saturated, unsaturated, or aromatic 5-7 membered ring with 0-3 heteroatoms selected from nitrogen, oxygen and sulfur.

23. A method of increasing the number of functional ABC transporters in a membrane of a cell, comprising the step of contacting said cell with a compound of formula I according to claim 1.

24. The method of claim 23, wherein the ABC transporter is CFTR.

25. A method of modulating CFTR activity comprising the step of contacting said CFTR with a compound of formula I according to claim 1.

26. A method of treating or lessening the severity of a disease in a patient in need thereof, wherein said disease is selected from cystic fibrosis, hereditary emphysema, COPD, or dry-eye disease, said method comprising the step of administering to said patient an effective amount of a compound of formula I according to claim 1.

* * * * *